US007384738B2

(12) United States Patent
Bremel et al.

(10) Patent No.: US 7,384,738 B2
(45) Date of Patent: Jun. 10, 2008

(54) RETROVIRUS-BASED GENOMIC SCREENING

(76) Inventors: Robert D. Bremel, E3352 Chapel Rd., Hillpoint, WI (US) 53937; Gregory T. Bleck, 1111 Silver Dr., Apt. 8, Baraboo, WI (US) 53913; Michael Imboden, 564 Park La., Madison, WI (US) 53711; Kurt Eakle, 339 Water St., Prairie du Sac, WI (US) 53578

( * ) Notice: Subject to any disclaimer, the term of this patent is extended or adjusted under 35 U.S.C. 154(b) by 492 days.

(21) Appl. No.: 10/397,569

(22) Filed: Mar. 26, 2003

(65) Prior Publication Data
US 2004/0002062 A1    Jan. 1, 2004

Related U.S. Application Data

(60) Provisional application No. 60/368,396, filed on Mar. 28, 2002.

(51) Int. Cl.
    *C12Q 1/68* (2006.01)
(52) U.S. Cl. ........................................................ 435/6
(58) Field of Classification Search ................ None
    See application file for complete search history.

(56) References Cited

U.S. PATENT DOCUMENTS

| | | | |
|---|---|---|---|
| 4,560,655 A | 12/1985 | Baker | |
| 4,657,866 A | 4/1987 | Kumar | |
| 4,677,066 A | 6/1987 | Takahashi et al. | 435/172.2 |
| 4,767,704 A | 8/1988 | Cleveland et al. | |
| 4,816,567 A | 3/1989 | Cabilly et al. | 530/387 |
| 4,927,762 A | 5/1990 | Darfler | |
| 4,937,190 A | 6/1990 | Palmenberg et al. | 435/69.1 |
| 4,946,778 A | 8/1990 | Ladner et al. | 435/69.6 |
| 5,122,469 A | 6/1992 | Mather et al. | |
| 5,139,941 A | 8/1992 | Myzyczka et al. | |
| 5,149,645 A | 9/1992 | Hoekema et al. | 435/172.3 |
| 5,168,062 A | 12/1992 | Stinski | 435/240.2 |
| 5,173,414 A | 12/1992 | Lebkowski et al. | 435/172.3 |
| 5,215,904 A | 6/1993 | Gould et al. | 435/172.3 |
| 5,225,347 A | 7/1993 | Goldberg et al. | 435/320.1 |
| 5,252,479 A * | 10/1993 | Srivastava | 435/235.1 |
| 5,385,839 A | 1/1995 | Stinski | 435/240.2 |
| 5,508,184 A | 4/1996 | Negrutiu et al. | 435/172.3 |
| 5,512,421 A | 4/1996 | Burns et al. | 435/320.1 |
| 5,512,443 A | 4/1996 | Schlom et al. | |
| 5,591,624 A | 1/1997 | Barber et al. | 435/240.2 |
| 5,618,682 A | 4/1997 | Scheirer | 435/8 |
| 5,627,058 A | 5/1997 | Ruley et al. | 435/172.3 |
| 5,670,113 A | 9/1997 | Akong et al. | |
| 5,674,713 A | 10/1997 | McElroy et al. | 435/69.7 |
| 5,686,120 A | 11/1997 | Mertz et al. | |
| 5,686,279 A | 11/1997 | Finer et al. | 435/172.3 |
| 5,716,832 A | 2/1998 | Barber et al. | 435/172.3 |
| 5,719,055 A | 2/1998 | Cooper | 435/320.1 |
| 5,721,121 A | 2/1998 | Etcheverry et al. | 435/69.7 |
| 5,807,689 A | 9/1998 | Daggett et al. | |
| 5,817,491 A | 10/1998 | Yee et al. | 435/172.3 |
| 5,834,256 A | 11/1998 | Finer et al. | 435/91.33 |
| 5,843,742 A | 12/1998 | Natsoulis et al. | |
| 5,850,000 A | 12/1998 | Bleck et al. | |
| 5,858,740 A | 1/1999 | Finer et al. | 435/172.3 |
| 5,866,400 A | 2/1999 | Palsson et al. | |
| 5,874,540 A | 2/1999 | Hansen et al. | |
| 5,876,946 A | 3/1999 | Burbaum et al. | |
| 5,892,019 A | 4/1999 | Schlom et al. | |
| 5,914,267 A | 6/1999 | Mertz et al. | 435/320.1 |
| 5,922,601 A | 7/1999 | Baetscher et al. | 435/456 |
| 5,948,675 A | 9/1999 | Klatzmann et al. | 435/320.1 |
| 5,952,212 A | 9/1999 | Moller et al. | 435/194 |
| 5,955,592 A | 9/1999 | Ullrich et al. | 536/23.2 |
| 5,958,719 A | 9/1999 | Ullrich et al. | 435/21 |
| 5,958,775 A | 9/1999 | Wickstrom et al. | 435/455 |
| 5,965,443 A | 10/1999 | Reznikoff et al. | 435/473 |
| 5,968,785 A | 10/1999 | Devine et al. | 435/91.41 |
| 5,976,796 A | 11/1999 | Szalay et al. | 435/6 |
| 5,976,852 A | 11/1999 | Cheng et al. | 435/196 |
| 5,976,853 A | 11/1999 | Guthridge et al. | 435/196 |
| 5,981,251 A | 11/1999 | Ullrich et al. | 435/196 |
| 5,993,813 A | 11/1999 | Mezes et al. | |

(Continued)

FOREIGN PATENT DOCUMENTS

| | | |
|---|---|---|
| EP | 117058 | 8/1984 |
| WO | WO 87/00195 | 1/1987 |
| WO | WO 90/03430 | 4/1990 |
| WO | WO 92/01070 | 1/1992 |
| WO | WO 93/02108 | 2/1993 |
| WO | WO 93/03143 | 2/1993 |
| WO | WO 93/03769 | 3/1993 |
| WO | WO 94/05786 | 3/1994 |
| WO | WO 94/24870 | 11/1994 |
| WO | WO 96/11013 | 4/1996 |
| WO | WO99/14310 | 3/1999 |
| WO | WO 99/43795 | 9/1999 |

OTHER PUBLICATIONS

Korman et al., "Expression of human class II major histocompatibilty complex antigens using retrovirus vectors," PNAS, USA, 1987, vol. 84, pp. 2150-2154.*

(Continued)

*Primary Examiner*—Young J. Kim

(57) ABSTRACT

The present invention relates to the expression and screening of genomic DNA sequences encoding uncharacterized genes and proteins. The present invention provides systems utilizing unique features of retroviral replication to analyze uncharacterized genes derived from genomic DNA samples. In preferred embodiments, a segment of genomic DNA is inserted between 5' and 3' viral long terminal repeats (LTRs) in a vector (e.g., a plasmid, cosmid, or artificial chromosome vector). The resulting vector (or library of vectors containing a plurality of independent genomic sequences) is then introduced into a retroviral packaging cell. The resulting provirus or proteins expression from the provirus are then analyzed.

10 Claims, 27 Drawing Sheets

U.S. PATENT DOCUMENTS

| | | | | |
|---|---|---|---|---|
| 5,994,074 | A | 11/1999 | Beach et al. | 435/6 |
| 5,994,136 | A | 11/1999 | Naldini et al. | 435/455 |
| 6,004,791 | A | 12/1999 | Aoki et al. | 435/194 |
| 6,013,455 | A | 1/2000 | Bandman et al. | 435/6 |
| 6,013,464 | A | 1/2000 | Abo et al. | 435/15 |
| 6,013,516 | A | 1/2000 | Verma et al. | 435/325 |
| 6,015,807 | A | 1/2000 | Engel et al. | 514/183 |
| 6,020,306 | A | 2/2000 | Boyd et al. | 514/2 |
| 6,025,192 | A | 2/2000 | Beach et al. | 435/320.1 |
| 6,027,722 | A | 2/2000 | Hodgson | 424/93.21 |
| 6,027,875 | A | 2/2000 | Weinberger | |
| 6,030,788 | A | 2/2000 | Gerhold | 435/6 |
| 6,030,822 | A | 2/2000 | Lechner et al. | 435/194 |
| 6,034,228 | A | 3/2000 | Norris et al. | 536/23.1 |
| 6,051,427 | A | 4/2000 | Finer et al. | 435/369 |
| 6,061,427 | A | 5/2000 | Ryoo | 379/1 |
| 6,074,859 | A | 6/2000 | Hirokawa et al. | 435/189 |
| 6,080,912 | A | 6/2000 | Bremel et al. | 800/23 |
| 6,136,597 | A | 10/2000 | Hope et al. | 435/325 |
| 6,187,287 | B1 | 2/2001 | Leung et al. | |
| 6,255,071 | B1 | 7/2001 | Beach et al. | 435/69.1 |
| 6,291,740 | B1 | 9/2001 | Bremel et al. | 800/23 |
| 6,319,707 | B1 | 11/2001 | Adam et al. | 435/320.1 |
| 6,331,415 | B1 | 12/2001 | Cabilly et al. | 435/69.6 |
| 6,333,195 | B1 | 12/2001 | Respess et al. | 435/456 |
| 6,368,862 | B1 | 4/2002 | Palmer et al. | 435/455 |
| 6,410,316 | B1 | 6/2002 | Sheridan et al. | 435/320.1 |
| 6,852,510 | B2 | 2/2005 | Bremel et al. | |
| 2001/0018203 | A1 | 8/2001 | Iba et al. | |
| 2001/0043921 | A1 | 11/2001 | Grunzburg et al. | |
| 2002/0034393 | A1 | 3/2002 | Mitrophanous et al. | |
| 2002/0104109 | A1 | 8/2002 | Bremel et al. | |
| 2002/0106729 | A1 | 8/2002 | Bleck | |
| 2003/0224415 | A1 | 12/2003 | Bremel et al. | |
| 2004/0002062 | A1 | 1/2004 | Bremel et al. | |
| 2004/0019920 | A1 | 1/2004 | Bremel et al. | |
| 2004/0038304 | A1 | 2/2004 | Bremel et al. | |
| 2004/0235173 | A1 | 11/2004 | Bleck et al. | |
| 2004/0253581 | A1 | 12/2004 | Eakle et al. | |
| 2005/0060762 | A1 | 3/2005 | Bleck | |
| 2005/0069552 | A1 | 3/2005 | Bleck et al. | |
| 2005/0100952 | A1 | 5/2005 | Bremel et al. | |

OTHER PUBLICATIONS

Dostatni et al., "Use of Retroviral Vectors for Mapping of Splice Sites in Cottontail Rabbit Papillomavirus," Journal of General Virology, 1988, vol. 69, pp. 3093-3100.*
Cepko et al. Current Protocols in Molecular Biology, supplement 36, Chapter 9.9.1., 1996.*
Kuno et al., "Constitutive kinase activation of the TEL-Syk fusion gene in myelodysplastic syndrome with t(9;12)(q22;p12)," Blood, Feb. 2001, vol. 97, No. 4, pp. 1050-1055.*
Mielke et al., Biochem. 35:2239-52 [1996].
Schroder and Friedl, Biotech. Bioeng. 53(6):547-59 [1997].
Weidle et al., Gene 66:193-203 [1988].
McBurney et al., Somatic Cell Molec. Genet. 20:529-40 [1994].
Allen et al., Plant Cell 5:603-13 [1993].
Mehtali et al., Gene 91:179-84 [1990].
Kricker et al., Proc. Natl. Acad. Sci. 89:1075-79 [1992].
Dorer and Henikoff, Cell 77:993-1002 [1994].
Anderson and Young, Quantitative Filter Hybridization, in *Nucleic Acid Hybridization* [1985].
Sambrook, J. et al., *Molecular Cloning: A Laboratory Manual*, 2nd ed., Cold Spring Harbor Laboratory Press, New York (1989) pp. 16.9-16.15.
Maniatis et al., Science 236:1237 [1987].
Voss et al., Trends Biochem. Sci., 11:287 [1986].
Dijkema et al., EMBO J. 4:761 [1985].
Uetsuki et al., J. Biol. Chem., 264:5791 [1989].
Kim et al., Gene 91:217 [1990].
Mizushima and Nagata Nuc. Acids. Res., 18:5322 [1990].
Gorman et al., Proc. Natl. Acad. Sci. USA 79:6777 [1982].
Boshart et al., Cell 41:521 [1985].
Sambrook et al., *Molecular Cloning: A Laboratory Manual*, 2nd ed., Cold Spring Harbor Laboratory Press, New York [1989], pp. 16.7-16.8.
Zwizinski et al., J. Biol. Chem. 255(16): 7973-77 [1980].
Gray et al., Gene 39(2): 247-54 [1985].
Martial et al., Science 205: 602-607 [1979].
Shelling and Smith, Gene Therapy 1:165-169 [1994].
Zhou et al., J. Exp. Med. 179:1867-1875 [1994].
Han et al., Proc. Natl. Acad. Sci. USA 88:4313-4317 [1991].
Uhlmann et al., Chem. Rev. 90:543-584 [1990].
Helene et al., Biochim. Biophys. Acta. 1049:99-125 [1990].
Agarwal et al., Proc. Natl. Acad. Sci. USA 85:7079-7083 [1989].
Heikkila et al., Nature 328:445-449 [1987].
Cech et al. (1992) J. Biol. Chem. 267:17479-17482.
Kotin, Human Gene Therapy 5:793-801 [1994].
Bems, K.I. "Parvoviridae and their Replication" in Fundamental Virology, 2nd Edition, (B.N. Fields and D.M. Knipe. eds.), 1991.
Ullrich and Schlessinger, Cell 61:203-212 [1990].
Neer, 1995, Cell 80:249-257 [1995].
Sternweis and Smrcka, Trends in Biochem. Sci. 17:502-506 [1992].
Carbonneau, H. and Tonks, Annu. Rev. Cell Biol. 8:463-93 [1992].
Saito et al., Cell Growth and Diff. 2:59-65 [1991].
Krueger et al., Proc. Natl. Acad. Sci. USA 89:7417-7421 [1992].
Köhler and Milstein, Nature 256:495-497 [1975].
Kozbor et al. Immunol. Today 4:72 [1983].
Cole et al., in *Monoclonal Antibodies and Cancer Therapy*, Alan R. Liss. Inc., pp. 77-96 [1985].
Huse et al., Science 246:1275-1281 [1989].
deWet et al., Mol. Cell. Biol. 7:725 [1987].
Graham et al., J. Gen Virol., 36:59 [1977].
Mather, Biol. Reprod. 23:243-251 [1980].
Mather et al., Annals N.Y. Acad. Sci., 383:44-68 [1982].
Evans et al., *Handbook of Plant Cell Culture*, 1: 124-176, MacMillan Publishing Co., New York [1983].
Binding, *Plant Protoplasts*, p. 21-37, CRC Press, Boca Raton [1985].
Potrykus and Shillito, *Methods in Enzymology*, vol. 118, Plant Molecular Biology, A. and H. Weissbach eds., Academic Press, Orlando [1986].
Hoess et al., Nucleic Acids Res. 14:2287-2300 [1986].
O'Gorman et al., Science 251:1351-55 [1991].
van Deursen et al., Proc. Natl. Acad. Sci. USA 92:7376-80 1995.
Miller and Baltimore Mol. Cell. Biol. 6:2895 [1986].
Markowitz et al., J. Virol. 62:1120 [1988].
Miller et al., Mol. Cell. Biol. 10:4239 [1990].
Miller and Rosman, BioTechniques 7:980 [1980].
Miller, Nature 357: 455 [1990].
Adams et al., Proc. Natl. Acad. Sci. USA 89:8981 [1992].
Mastromarino et al., J. Gen. Virol. 68:2359 [1977].
Burns et al. Proc. Natl. Acad. Sci. USA 90:8033 [1993].
Roe et al., EMBO J. 12:2099 [1993].
Naldini et al., Science 272:263 [1996].
Carter, B.J., Current Opinion in Biotechnology 3:533-539 [1992].
de la Cruz et al., J. Bact. 175: 6932-38 [1993].
Craig, Curr. Topics Microbiol. Immunol. 204: 27-48 [1996].
Morisato and Kleckner, Cell 51:101-111 [1987].
Cleveland et al., J. Immunol. Methods (1983)56:221-234 [1983], *Animal Cell Culture: A Practical Approach 2nd Ed.*, Rickwood, D. and Hames, B. D., eds. Oxford University Press, New York [1992].
Wilson et al., Cell, 37:767 [1984].
Schroeder and Neagle, J. Biomol. Screening 1:75-80 [1996].
Denyer et al., Drug Discov. Today 3:323-32 [1998].
Gonzales et al., Drug. Discov. Today 4:431-39 [1999].
Graham and Van der Eb, Virol. 52:456 [1973].
Goff et al., J. Virol. 38:239 [1981].
Quade, Virol. 98:461 [1979].
Yee et al., Meth. Cell Biol. 43:99 [1994].
Chen and Okayama (Mol. Cell. Biol., 7:2745, 1987.
Shillito, et al., Plant Cell Reports, 2, 244-247 (1983).

Harlow and Lane, *Antibodies: A Laboratory Manual*, Cold Spring Harbor Laboratory Press, Cold Spring Harbor, NY, 1988.
Brun et al., Intervirol, 38:274 (1995).
Masters et al., Virol. 171:285 (1990).
Mebatsion et al., J. Virol. 69:1444 (1995).
Scheper et al., Biochem. 76: 801-809 [1994].
Meyer et al., J. Virol. 69: 2819-2824 [1995].
Jang et al., 1988, J. Virol. 62: 2636-2643 [1998].
Haller et al., J. Virol. 66: 5075-5086 [1995].
Lebkowski et al., Molec. Cell. Biol. 8:3988-3996 [1988].
Vincent et al., Vaccines 90 [1990].
Carter, Current Opinion in Biotechnology 3:533-539 [1992].
Muzyczka, Current Topics in Microbiol. and Immunol. 158:97-129 [1992].
Rogers et al., Strategies 13:97-99 (2000).
Felts et al., Strategies 13:15-18 (2000).
Felts et al., Strategies 12:74-77 (1999).
Poul et al., Immunotechnology, Elsevier Science Publishers BV, NL 1:189-196 (1995).
Zufferey et al., J. of Virology 73:2886-2892 (1999).
Wang et al., Gene 182:145-150 (1996).
Vaillancourt et al., Strategies 13:50-53 (2000).
Han et al., PNAS 88:4313-4317 (1991).
Teysset et al., J. of Virology 72:853 (1998).
Perkins et al., DNA 8:59-68 (1989).
Stuhlmann et al., J. Virology 66:2378 (1991).

* cited by examiner

Figure 1

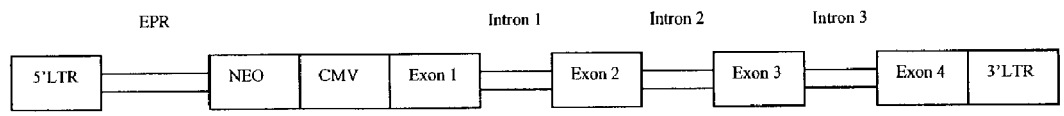

| | |
|---|---|
| 5' LTR= | Moloney murine sarcoma virus 5' long terminal repeat. |
| EPR= | Moloney murine leukemia virus extended packaging region. |
| NEO= | Neomycin phosphotransferase gene. |
| CMV= | Human cytomegalovirus immediate early promoter. |
| Exon 1= | Bovine α-lactalbumin exon 1. |
| Intron 1= | Bovine α-lactalbumin intron 1. |
| Exon 2= | Bovine α-lactalbumin exon 2. |
| Intron 2= | Bovine α-lactalbumin intron 2. |
| Exon 3= | Bovine α-lactalbumin exon 3. |
| Intron 3= | Bovine α-lactalbumin intron 3. |
| Exon 4= | Bovine α-lactalbumin exon 4. |
| 3' LTR= | Moloney murine leukemia virus 3' LTR. |

Figure 2A

SEQ ID NO:1

```
   1  GAATTAATTCATACCAGATCACCGAAAACTGTCCTCCAAATGTGTCCCCC
  51  TCACACTCCCAAATTCGCGGGCTTCTGCCTCTTAGACCACTCTACCCTAT
 101  TCCCCACACTCACCGGAGCCAAAGCCGCGGCCCTTCCGTTTCTTTGCTTT
 151  TGAAAGACCCCACCCGTAGGTGGCAAGCTAGCTTAAGTAACGCCACTTTG
 201  CAAGGCATGGAAAAATACATAACTGAGAATAGAAAAGTTCAGATCAAGGT
 251  CAGGAACAAAGAAACAGCTGAATACCAAACAGGATATCTGTGGTAAGCGG
 301  TTCCTGCCCCGGCTCAGGGCCAAGAACAGATGAGACAGCTGAGTGATGGG
 351  CCAAACAGGATATCTGTGGTAAGCAGTTCCTGCCCCGGCTCGGGGCCAAG
 401  AACAGATGGTCCCCAGATGCGGTCCAGCCCTCAGCAGTTTCTAGTGAATC
 451  ATCAGATGTTTCCAGGGTGCCCCAAGGACCTGAAAATGACCCTGTACCTT
 501  ATTTGAACTAACCAATCAGTTCGCTTCTCGCTTCTGTTCGCGCGCTTCCG
 551  CTCTCCGAGCTCAATAAAAGAGCCCACAACCCCTCACTCGGCGCGCCAGT
 601  CTTCCGATAGACTGCGTCGCCCGGGTACCCGTATTCCCAATAAAGCCTCT
 651  TGCTGTTTGCATCCGAATCGTGGTCTCGCTGTTCCTTGGGAGGGTCTCCT
 701  CTGAGTGATTGACTACCCACGACGGGGGTCTTTCATTTGGGGGCTCGTCC
 751  GGGATTTGGAGACCCCTGCCCAGGGACCACCGACCCACCACCGGGAGGTA
 801  AGCTGGCCAGCAACTTATCTGTGTCTGTCCGATTGTCTAGTGTCTATGTT
 851  TGATGTTATGCGCCTGCGTCTGTACTAGTTAGCTAACTAGCTCTGTATCT
 901  GGCGGACCCGTGGTGGAACTGACGAGTTCTGAACACCCGGCCGCAACCCT
 951  GGGAGACGTCCCAGGGACTTTGGGGGCCGTTTTTGTGGCCCGACCTGAGG
1001  AAGGGAGTCGATGTGGAATCCGACCCCGTCAGGATATGTGGTTCTGGTAG
1051  GAGACGAGAACCTAAAACAGTTCCCGCCTCCGTCTGAATTTTTGCTTTCG
1101  GTTTGGAACCGAAGCCGCGCGTCTTGTCTGCTGCAGCGCTGCAGCATCGT
1151  TCTGTGTTGTCTCTGTCTGACTGTGTTTCTGTATTTGTCTGAAAATTAGG
1201  GCCAGACTGTTACCACTCCCTTAAGTTTGACCTTAGGTCACTGGAAAGAT
1251  GTCGAGCGGATCGCTCACAACCAGTCGGTAGATGTCAAGAAGAGACGTTG
```

Figure 2B

```
1301  GGTTACCTTCTGCTCTGCAGAATGGCCAACCTTTAACGTCGGATGGCCGC
1351  GAGACGGCACCTTTAACCGAGACCTCATCACCCAGGTTAAGATCAAGGTC
1401  TTTTCACCTGGCCCGCATGGACACCCAGACCAGGTCCCCTACATCGTGAC
1451  CTGGGAAGCCTTGGCTTTTGACCCCCTCCCTGGGTCAAGCCCTTTGTAC
1501  ACCCTAAGCCTCCGCCTCCTCTTCCTCCATCCGCCCCGTCTCTCCCCCTT
1551  GAACCTCCTCGTTCGACCCCGCCTCGATCCTCCCTTTATCCAGCCCTCAC
1601  TCCTTCTCTAGGCGCCGGAATTCCGATCTGATCAAGAGACAGGATGAGGA
1651  TCGTTTCGCATGATTGAACAAGATGGATTGCACGCAGGTTCTCCGGCCGC
1701  TTGGGTGGAGAGGCTATTCGGCTATGACTGGGCACAACAGACAATCGGCT
1751  GCTCTGATGCCGCCGTGTTCCGGCTGTCAGCGCAGGGGCGCCCGGTTCTT
1801  TTTGTCAAGACCGACCTGTCCGGTGCCCTGAATGAACTGCAGGACGAGGC
1851  AGCGCGGCTATCGTGGCTGGCCACGACGGGCGTTCCTTGCGCAGCTGTGC
1901  TCGACGTTGTCACTGAAGCGGGAAGGGACTGGCTGCTATTGGGCGAAGTG
1951  CCGGGGCAGGATCTCCTGTCATCTCACCTTGCTCCTGCCGAGAAAGTATC
2001  CATCATGGCTGATGCAATGCGGCGGCTGCATACGCTTGATCCGGCTACCT
2051  GCCCATTCGACCACCAAGCGAAACATCGCATCGAGCGAGCACGTACTCGG
2101  ATGGAAGCCGGTCTTGTCGATCAGGATGATCTGGACGAAGAGCATCAGGG
2151  GCTCGCGCCAGCCGAACTGTTCGCCAGGCTCAAGGCGCGCATGCCCGACG
2201  GCGAGGATCTCGTCGTGACCCATGGCGATGCCTGCTTGCCGAATATCATG
2251  GTGGAAAATGGCCGCTTTTCTGGATTCATCGACTGTGGCCGGCTGGGTGT
2301  GGCGGACCGCTATCAGGACATAGCGTTGGCTACCCGTGATATTGCTGAAG
2351  AGCTTGGCGGCGAATGGGCTGACCGCTTCCTCGTGCTTTACGGTATCGCC
2401  GCTCCCGATTCGCAGCGCATCGCCTTCTATCGCCTTCTTGACGAGTTCTT
2451  CTGAGCGGGACTCTGGGGTTCGAAATGACCGACCAAGCGACGCCCAACCT
2501  GCCATCACGAGATTTCGATTCCACCGCCGCCTTCTATGAAAGGTTGGGCT
2551  TCGGAATCGTTTTCCGGGACGCCGGCTGGATGATCCTCCAGCGCGGGAT
2601  CTCATGCTGGAGTTCTTCGCCCACCCCGGGCTCGATCCCCTCGCGAGTTG
2651  GTTCAGCTGCTGCCTGAGGCTGGACGACCTCGCGGAGTTCTACCGGCAGT
2701  GCAAATCCGTCGGCATCCAGGAAACCAGCAGCGGCTATCCGCGCATCCAT
2751  GCCCCCGAACTGCAGGAGTGGGGAGGCACGATGGCCGCTTTGGTCGAGGC
```

Figure 2C

```
2801  GGATCCGGCCATTAGCCATATTATTCATTGGTTATATAGCATAAATCAAT
2851  ATTGGCTATTGGCCATTGCATACGTTGTATCCATATCATAATATGTACAT
2901  TTATATTGGCTCATGTCCAACATTACCGCCATGTTGACATTGATTATTGA
2951  CTAGTTATTAATAGTAATCAATTACGGGGTCATTAGTTCATAGCCCATAT
3001  ATGGAGTTCCGCGTTACATAACTTACGGTAAATGGCCCGCCTGGCTGACC
3051  GCCCAACGACCCCCGCCCATTGACGTCAATAATGACGTATGTTCCCATAG
3101  TAACGCCAATAGGGACTTTCCATTGACGTCAATGGGTGGAGTATTTACGG
3151  TAAACTGCCCACTTGGCAGTACATCAAGTGTATCATATGCCAAGTACGCC
3201  CCCTATTGACGTCAATGACGGTAAATGGCCCGCCTGGCATTATGCCCAGT
3251  ACATGACCTTATGGGACTTTCCTACTTGGCAGTACATCTACGTATTAGTC
3301  ATCGCTATTACCATGGTGATGCGGTTTTGGCAGTACATCAATGGGCGTGG
3351  ATAGCGGTTTGACTCACGGGGATTTCCAAGTCTCCACCCCATTGACGTCA
3401  ATGGGAGTTTGTTTTGGCACCAAAATCAACGGGACTTTCCAAAATGTCGT
3451  AACAACTCCGCCCCATTGACGCAAATGGGCGGTAGGCATGTACGGTGGGA
3501  GGTCTATATAAGCAGAGCTCGTTTAGTGAACCGTCAGATCGCCTGGAGAC
3551  GCCATCCACGCTGTTTTGACCTCCATAGAAGACACCGGGACCGATCCAGC
3601  CTCCGCGGCCCCAAGCTTCTCGAGTTAACAGATCTCGACCTGCACCCCCT
3651  AACCAAAATGATGTCCTTTGTCTCTCTGCTCCTGGTAGGCATCCTATTCC
3701  ATGCCACCCAGGCTGAACAGTTAACAAAATGTGAGGTGTTCCGGGAGCTG
3751  AAAGACTTGAAGGGCTACGGAGGTGTCAGTTTGCCTGAATGTGAGTTCCC
3801  TGCTATTTTGCTTTGTCCCATAATTCATCCTCTTCACTCTTTCCCTCCAT
3851  TCTCTTCATCCTCTTTTCCCCCTCTACTTTTAATTATCAAACAATTCTCT
3901  TATTTGTTTACTCTTTTATTACATTTATTTATCTGCCTCTCCTTTTTCCC
3951  ATTGTCTGATCCTTTGGAACTCTTTTCACCTTAACAAGATACTCTGTGGT
4001  CTGCCATATTTGGAGATTGGTTGGAGAGCCTTTTTCGGTCTGGGAATACA
4051  GGTCCTCATTTATGCTATACATGAACATCCTTGTGAAATCTCTTTTTCGT
4101  CTTTCTTTCAGGGGTCTGTACCGCGTTTCATACCAGTGGTTATGACACAC
4151  AAGCCATAGTACAAAACAATGACAGCACAGAATATGGACTCTTCCAGATA
4201  AATAATAAAATTTGGTGCAAAGACGACCAGAACCCTCACTCAAGCAACAT
4251  CTGTAACATCTCCTGTGACAGTGAGTAACTTCTTTTTACTCTGTTCCTGT
```

Figure 2D

```
4301  GTTTTTCTGAAACCTACTCCTGGGATAACCTCCTTTTTTTTGGTGTGAAG
4351  CACACCTCTGGCTTCACTGCCTTGGACTCCAAATTAACTGTGGGACTTGA
4401  TAATACCGAGTAAGAGGCTCTTAGAATTTTTCATTAACACTAAATCCCCA
4451  GACAGTTTCTTAAAGTTCCTGGGTAGGTGACCTGAGCTGTTTGGGGATCT
4501  TGATGTATAATACCCTGTATTTTCAGACTAAGTTGGTTGATGAAGTTGAT
4551  AATTCCTAAGGAGCTGCCCCAGAGAAGAGAAGGGAGTCCTTACCTAGGGA
4601  TAGGCATTACTGTATTAAATTTCTCACCCAGAAGGCAACAGGCATAAGCC
4651  TCTAGTTCAGAGAAAACCAGAGAAGAGGGAAATTCATTATCCTTCTGGGT
4701  AATACTTAGCTCTCTCATTTTTTCCACCAGAGGCTCCTGCCAGAGTTCCT
4751  GGATGATGATCTTACTGATGACATTATGTGTGTCAAGAAGATTCTGGATA
4801  AAGTAGGAATTAACTACTGGTGAGTCACCTCTCTATTTTTCACTTAATCT
4851  TTCCTCTCTTTCTTCTCAGTCCTTTCGTCCCAGCACTATACTCCTTTCTC
4901  TCTATTTCTTGGTCTTTTAAGCTAGAATGTAATCTTAAAAACAAAAATCA
4951  TCAAGCAGACTCCGGTTTCCAATTTTGAAGCTTCACTTACTTCACTCCCG
5001  TTAGCAATTTTCCTACCTAAGGGTCCCTAATAGAGGGCTGAGATCCAGGA
5051  TTTCCTTCACCAGGACTTGAACATCTAATTCTACTTGTTCAGTCCTACAT
5101  CCTAAGGCACGCCCTTTGACCACTGCCCCGCAATTTTCTTGGAGTTTTAA
5151  AAAATGGACCTTACTCCACTAAGTGGCTCAGTGTCTCTAGCCATGTGGCT
5201  AGGAAAGTCTGTCTGTAATTTTAACCCACAGTCTTCCACCTCAGCCTTCC
5251  TGGGGATAAAGCTAGATGTAAATCTAACCAAGATCCTGTCAGTAATTTGC
5301  CTTGTCTCCTTCTTCATGATCAGGTTGGCCCATAAAGCACTCTGTTCTGA
5351  GAAGCTGGATCAGTGGCTCTGTGAGAAGTTGTGAACACCTGCTGTCTTTG
5401  CTGCTTCTGTCCTCTTTCTGTTCCTGGAACTCCTCTGCCCCGTGGCTACC
5451  TCGTTTTGCTTCTTTGTACCCCCTTGAAGCTAACTCGTCTCTGAGCCCTG
5501  GGCCCTGTAGTGACAATGGACATGTAAGGACTAATCTCCAGGTGTGCATG
5551  AATGGCGCTCTGGACTTTTGACCCTTGCTCGATGTCCCTGATGGCGCTTT
5601  TAATGCAACAGTACATATTCCACTTTTGTCCCGAATAAAAGCCTGATTT
5651  TGAGTGGCTGGCTGTATTTTCTTCCTGGTGGGAGAGGGAGGAAATAGGGT
5701  GAGTAGGTAGACCTGGCCATGGGTCACAGACCCCTTCATCTCTACTAAAG
5751  AGGATAGAGAGGCTGAACTTATAACAACTCAAAGATGGAGATTACTTTCT
```

Figure 2E

```
5801  GTATTAATTCAATTCAACAGAGTTTTATTGATCACCTAGCATAATTTAAA
5851  GAGCTATGGAGGGGATCTAAAGTTGACTAAAAGCATCTCTTACCTAAACT
5901  GCTGCTAAGTCACTTCAGTTGTGTCCGACTCTGTGTGACCCCATAGACGG
5951  TAGCCCACAAGGCTCCCATGTCCCTGGAATTCGATATCAAGCTTATCGAT
6001  ACCGTCGACATCGATAAATAAAAGATTTTATTTAGTCTCCAGAAAAAGG
6051  GGGGAATGAAAGACCCCACCTGTAGGTTTGGCAAGCTAGCTTAAGTAACG
6101  CCATTTTGCAAGGCATGGAAAATACATAACTGAGAATAGAGAAGTTCAG
6151  ATCAAGGTCAGGAACAGATGGAACAGCTGAATATGGGCCAAACAGGATAT
6201  CTGTGGTAAGCAGTTCCTGCCCCGGCTCAGGGCCAAGAACAGATGGAACA
6251  GCTGAATATGGGCCAAACAGGATATCTGTGGTAAGCAGTTCCTGCCCCGG
6301  CTCAGGGCCAAGAACAGATGGTCCCCAGATGCGGTCCAGCCCTCAGCAGT
6351  TTCTAGAGAACCATCAGATGTTTCCAGGGTGCCCCAAGGACCTGAAATGA
6401  CCCTGTGCCTTATTTGAACTAACCAATCAGTTCGCTTCTCGCTTCTGTTC
6451  GCGCGCTTCTGCTCCCCGAGCTCAATAAAAGAGCCCACAACCCCTCACTC
6501  GGGGCGCCAGTCCTCCGATTGACTGAGTCGCCCGGGTACCCGTGTATCCA
6551  ATAAACCCTCTTGCAGTTGCATCCGACTTGTGGTCTCGCTGTTCCTTGGG
6601  AGGGTCTCCTCTGAGTGATTGACTACCCGTCAGCGGGGGTCTTTCATTTG
6651  GGGGCTCGTCCGGGATCGGGAGACCCCTGCCCAGGGACCACCGACCCACC
6701  ACCGGGAGGTAAGCTGGCTGCCTCGCGCGTTTCGGTGATGACGGTGAAAA
6751  CCTCTGACACATGCAGCTCCCGGAGACGGTCACAGCTTGTCTGTAAGCGG
6801  ATGCCGGGAGCAGACAAGCCCGTCAGGGCGCGTCAGCGGGTGTTGGCGGG
6851  TGTCGGGGCGCAGCCATGACCCAGTCACGTAGCGATAGCGGAGTGTATAC
6901  TGGCTTAACTATGCGGCATCAGAGCAGATTGTACTGAGAGTGCACCATAT
6951  GCGGTGTGAAATACCGCACAGATGCGTAAGGAGAAAATACCGCATCAGGC
7001  GCTCTTCCGCTTCCTCGCTCACTGACTCGCTGCGCTCGGTCGTTCGGCTG
7051  CGGCGAGCGGTATCAGCTCACTCAAAGGCGGTAATACGGTTATCCACAGA
7101  ATCAGGGGATAACGCAGGAAAGAACATGTGAGCAAAAGGCCAGCAAAAGG
7151  CCAGGAACCGTAAAAAGGCCGCGTTGCTGGCGTTTTTCCATAGGCTCCGC
7201  CCCCCTGACGAGCATCACAAAAATCGACGCTCAAGTCAGAGGTGGCGAAA
7251  CCCGACAGGACTATAAAGATACCAGGCGTTTCCCCCTGGAAGCTCCCTCG
```

Figure 2F

```
7301  TGCGCTCTCCTGTTCCGACCCTGCCGCTTACCGGATACCTGTCCGCCTTT
7351  CTCCCTTCGGGAAGCGTGGCGCTTTCTCATAGCTCACGCTGTAGGTATCT
7401  CAGTTCGGTGTAGGTCGTTCGCTCCAAGCTGGGCTGTGTGCACGAACCCC
7451  CCGTTCAGCCCGACCGCTGCGCCTTATCCGGTAACTATCGTCTTGAGTCC
7501  AACCCGGTAAGACACGACTTATCGCCACTGGCAGCAGCCACTGGTAACAG
7551  GATTAGCAGAGCGAGGTATGTAGGCGGTGCTACAGAGTTCTTGAAGTGGT
7601  GGCCTAACTACGGCTACACTAGAAGGACAGTATTTGGTATCTGCGCTCTG
7651  CTGAAGCCAGTTACCTTCGGAAAAAGAGTTGGTAGCTCTTGATCCGGCAA
7701  ACAAACCACCGCTGGTAGCGGTGGTTTTTTGTTTGCAAGCAGCAGATTA
7751  CGCGCAGAAAAAAAGGATCTCAAGAAGATCCTTTGATCTTTTCTACGGGG
7801  TCTGACGCTCAGTGGAACGAAAACTCACGTTAAGGGATTTTGGTCATGAG
7851  ATTATCAAAAGGATCTTCACCTAGATCCTTTTAAATTAAAAATGAAGTT
7901  TTAAATCAATCTAAAGTATATATGAGTAAACTTGGTCTGACAGTTACCAA
7951  TGCTTAATCAGTGAGGCACCTATCTCAGCGATCTGTCTATTTCGTTCATC
8001  CATAGTTGCCTGACTCCCCGTCGTGTAGATAACTACGATACGGGAGGGCT
8051  TACCATCTGGCCCCAGTGCTGCAATGATACCGCGAGACCCACGCTCACCG
8101  GCTCCAGATTTATCAGCAATAAACCAGCCAGCCGGAAGGGCCGAGCGCAG
8151  AAGTGGTCCTGCAACTTTATCCGCCTCCATCCAGTCTATTAATTGTTGCC
8201  GGGAAGCTAGAGTAAGTAGTTCGCCAGTTAATAGTTTGCGCAACGTTGTT
8251  GCCATTGCTGCAGGCATCGTGGTGTCACGCTCGTCGTTTGGTATGGCTTC
8301  ATTCAGCTCCGGTTCCCAACGATCAAGGCGAGTTACATGATCCCCCATGT
8351  TGTGCAAAAAAGCGGTTAGCTCCTTCGGTCCTCCGATCGTTGTCAGAAGT
8401  AAGTTGGCCGCAGTGTTATCACTCATGGTTATGGCAGCACTGCATAATTC
8451  TCTTACTGTCATGCCATCCGTAAGATGCTTTTCTGTGACTGGTGAGTACT
8501  CAACCAAGTCATTCTGAGAATAGTGTATGCGGCGACCGAGTTGCTCTTGC
8551  CCGGCGTCAACACGGGATAATACCGCGCCACATAGCAGAACTTTAAAAGT
8601  GCTCATCATTGGAAAACGTTCTTCGGGGCGAAAACTCTCAAGGATCTTAC
8651  CGCTGTTGAGATCCAGTTCGATGTAACCCACTCGTGCACCCAACTGATCT
8701  TCAGCATCTTTTACTTTCACCAGCGTTTCTGGGTGAGCAAAAACAGGAAG
8751  GCAAAATGCCGCAAAAAGGGAATAAGGGCGACACGGAAATGTTGAATAC
```

Figure 2G

```
8801  TCATACTCTTCCTTTTTCAATATTATTGAAGCATTTATCAGGGTTATTGT
8851  CTCATGAGCGGATACATATTTGAATGTATTTAGAAAAATAAACAAATAGG
8901  GGTTCCGCGCACATTTCCCCGAAAAGTGCCACCTGACGTCTAAGAAACCA
8951  TTATTATCATGACATTAACCTATAAAAATAGGCGTATCACGAGGCCCTTT
9001  CGTCTTCAA
```

| | |
|---|---|
| 1-148 | LNC plasmid backbone |
| 149-737 | Moloney murine sarcoma virus 5' LTR |
| 807-1616 | Moloney murine leukemia virus extended packaging signal |
| 1660-2454 | Neomycin phosphotransferase gene |
| 2804-3617 | Human cytomegalovirus immediate early promoter |
| 3652-3790 | Bovine α-lactalbumin exon 1 |
| 3658-3714 | Bovine α-lactalbumin signal peptide coding region |
| 3791-4111 | Bovine α-lactalbumin intron 1 |
| 4112-4270 | Bovine α-lactalbumin exon 2 |
| 4271-4743 | Bovine α-lactalbumin intron 2 |
| 4744-4819 | Bovine α-lactalbumin exon 3 |
| 4820-5323 | Bovine α-lactalbumin intron 3 |
| 5324-5653 | Bovine α-lactalbumin exon 4 |
| 5382-5384 | Bovine α-lactalbumin stop codon |
| 5654-5982 | 3' flanking region of the bovine α-lactalbumin gene |
| 6054-6648 | Moloney murine leukemia virus 3' LTR |
| 6649-9009 | LNC plasmid backbone |

Primer 3: (P3) was created in the 3' end of Exon 1 (Exn 1)

Primer 4: (P4) was created in the 5' end of Exon 4 (Exn 4)

Schematic diagram of β-casein construct

EPR = MLV extended packaging region
Exn = Exon
Int = Intron

Figure 5A

SEQ ID NO:4

```
   1  TTTGAAAGACCCCACCCGTAGGTGGCAAGCTAGCTTAAGTAACGCCACTT
  51  TGCAAGGCATGGAAAAATACATAACTGAGAATAGAAAAGTTCAGATCAAG
 101  GTCAGGAACAAAGAAACAGCTGAATACCAAACAGGATATCTGTGGTAAGC
 151  GGTTCCTGCCCCGGCTCAGGGCCAAGAACAGATGAGACAGCTGAGTGATG
 201  GGCCAAACAGGATATCTGTGGTAAGCAGTTCCTGCCCCGGCTCGGGGCCA
 251  AGAACAGATGGTCCCCAGATGCGGTCCAGCCCTCAGCAGTTTCTAGTGAA
 301  TCATCAGATGTTTCCAGGGTGCCCCAAGGACCTGAAAATGACCCTGTACC
 351  TTATTTGAACTAACCAATCAGTTCGCTTCTCGCTTCTGTTCGCGCGCTTC
 401  CGCTCTCCGAGCTCAATAAAAGAGCCCACAACCCCTCACTCGGCGCGCCA
 451  GTCTTCCGATAGACTGCGTCGCCCGGGTACCCGTATTCCCAATAAAGCCT
 501  CTTGCTGTTTGCATCCGAATCGTGGTCTCGCTGTTCCTTGGGAGGGTCTC
 551  CTCTGAGTGATTGACTACCCACGACGGGGGTCTTTCATTTGGGGGCTCGT
 601  CCGGGATTTGGAGACCCCTGCCCAGGGACCACCGACCCACCACCGGGAGG
 651  TAAGCTGGCCAGCAACTTATCTGTGTCTGTCCGATTGTCTAGTGTCTATG
 701  TTTGATGTTATGCGCCTGCGTCTGTACTAGTTAGCTAACTAGCTCTGTAT
 751  CTGGCGGACCCGTGGTGGAACTGACGAGTTCTGAACACCCGGCCGCAACC
 801  CTGGGAGACGTCCCAGGGACTTTGGGGGCCGTTTTTGTGGCCCGACCTGA
 851  GGAAGGGAGTCGATGTGGAATCCGACCCCGTCAGGATATGTGGTTCTGGT
 901  AGGAGACGAGAACCTAAAACAGTTCCCGCCTCCGTCTGAATTTTTGCTTT
 951  CGGTTTGGAACCGAAGCCGCGCGTCTTGTCTGCTGCAGCGCTGCAGCATC
1001  GTTCTGTGTTGTCTCTGTCTGACTGTGTTTCTGTATTTGTCTGAAAATTA
1051  GGGCCAGACTGTTACCACTCCCTTAAGTTTGACCTTAGGTCACTGGAAAG
1101  ATGTCGAGCGGATCGCTCACAACCAGTCGGTAGATGTCAAGAAGAGACGT
1151  TGGGTTACCTTCTGCTCTGCAGAATGGCCAACCTTTAACGTCGGATGGCC
1201  GCGAGACGGCACCTTTAACCGAGACCTCATCACCCAGGTTAAGATCAAGG
1251  TCTTTTCACCTGGCCCGCATGGACACCCAGACCAGGTCCCCTACATCGTG
1301  ACCTGGGAAGCCTTGGCTTTTGACCCCCCTCCCTGGGTCAAGCCCTTTGT
1351  ACACCCTAAGCCTCCGCCTCCTCTTCCTCCATCCGCCCCGTCTCTCCCCC
1401  TTGAACCTCCTCGTTCGACCCCGCCTCGATCCTCCCTTTATCCAGCCCTC
1451  ACTCCTTCTCTAGGCGCCGGAATTCCGATCTGATCAAGAGACAGGATGAG
1501  GATCGTTTCGCATGATTGAACAAGATGGATTGCACGCAGGTTCTCCGGCC
1551  GCTTGGGTGGAGAGGCTATTCGGCTATGACTGGGCACAACAGACAATCGG
1601  CTGCTCTGATGCCGCCGTGTTCCGGCTGTCAGCGCAGGGGCGCCCGGTTC
1651  TTTTTGTCAAGACCGACCTGTCCGGTGCCCTGAATGAACTGCAGGACGAG
1701  GCAGCGCGGCTATCGTGGCTGGCCACGACGGGCGTTCCTTGCGCAGCTGT
1751  GCTCGACGTTGTCACTGAAGCGGGAAGGGACTGGCTGCTATTGGGCGAAG
1801  TGCCGGGGCAGGATCTCCTGTCATCTCACCTTGCTCCTGCCGAGAAAGTA
1851  TCCATCATGGCTGATGCAATGCGGCGGCTGCATACGCTTGATCCGGCTAC
1901  CTGCCCATTCGACCACCAAGCGAAACATCGCATCGAGCGAGCACGTACTC
1951  GGATGGAAGCCGGTCTTGTCGATCAGGATGATCTGGACGAAGAGCATCAG
2001  GGGCTCGCGCCAGCCGAACTGTTCGCCAGGCTCAAGGCGCGCATGCCCGA
2051  CGGCGAGGATCTCGTCGTGACCCATGGCGATGCCTGCTTGCCGAATATCA
2101  TGGTGGAAAATGGCCGCTTTTCTGGATTCATCGACTGTGGCCGGCTGGGT
2151  GTGGCGGACCGCTATCAGGACATAGCGTTGGCTACCCGTGATATTGCTGA
2201  AGAGCTTGGCGGCGAATGGGCTGACCGCTTCCTCGTGCTTTACGGTATCG
2251  CCGCTCCCGATTCGCAGCGCATCGCCTTCTATCGCCTTCTTGACGAGTTC
2301  TTCTGAGCGGGACTCTGGGGTTCGAAATGACCGACCAAGCGACGCCCAAC
2351  CTGCCATCACGAGATTTCGATTCCACCGCCGCCTTCTATGAAAGGTTGGG
2401  CTTCGGAATCGTTTTCCGGGACGCCGGCTGGATGATCCTCCAGCGCGGGG
```

Figure 5B

```
2451 ATCTCATGCTGGAGTTCTTCGCCCACCCCGGGCTCGATCCCCTCGCGAGT
2501 TGGTTCAGCTGCTGCCTGAGGCTGGACGACCTCGCGGAGTTCTACCGGCA
2551 GTGCAAATCCGTCGGCATCCAGGAAACCAGCAGCGGCTATCCGCGCATCC
2601 ATGCCCCCGAACTGCAGGAGTGGGGAGGCACGATGGCCGCTTTGGTCGAG
2651 GCGGATCCGGCCATTAGCCATATTATTCATTGGTTATATAGCATAAATCA
2701 ATATTGGCTATTGGCCATTGCATACGTTGTATCCATATCATAATATGTAC
2751 ATTTATATTGGCTCATGTCCAACATTACCGCCATGTTGACATTGATTATT
2801 GACTAGTTATTAATAGTAATCAATTACGGGGTCATTAGTTCATAGCCCAT
2851 ATATGGAGTTCCGCGTTACATAACTTACGGTAAATGGCCCGCCTGGCTGA
2901 CCGCCCAACGACCCCCGCCCATTGACGTCAATAATGACGTATGTTCCCAT
2951 AGTAACGCCAATAGGGACTTTCCATTGACGTCAATGGGTGGAGTATTTAC
3001 GGTAAACTGCCCACTTGGCAGTACATCAAGTGTATCATATGCCAAGTACG
3051 CCCCCTATTGACGTCAATGACGGTAAATGGCCCGCCTGGCATTATGCCCA
3101 GTACATGACCTTATGGGACTTTCCTACTTGGCAGTACATCTACGTATTAG
3151 TCATCGCTATTACCATGGTGATGCGGTTTTGGCAGTACATCAATGGGCGT
3201 GGATAGCGGTTTGACTCACGGGGATTTCCAAGTCTCCACCCCATTGACGT
3251 CAATGGGAGTTTGTTTTGGCACCAAAATCAACGGGACTTTCCAAAATGTC
3301 GTAACAACTCCGCCCCATTGACGCAAATGGGCGGTAGGCATGTACGGTGG
3351 GAGGTCTATATAAGCAGAGCTCGTTTAGTGAACCGTCAGATCGCCTGGAG
3401 ACGCCATCCACGCTGTTTTGACCTCCATAGAAGACACCGGGACCGATCCA
3451 GCCTCCGCGGCCCCAAGCTTCTCGAGTTAACAGATCCCCGATCACATTCA
3501 GCTCCTCCTTCACTTCTTGTCCTCTACTTTGGAAAAAAGGTAAGAATCTC
3551 AGATATAATTTCATTGTATCTGCTACTCATCTTTATTTCAGACTAGGTTA
3601 AAATGTAGAAAGAACATAATTGCTTAAAATAGATCTTAAAAATAAGGATG
3651 TTTAAGATAAAGTTTACAGTATTTTCAGCAAATTTGTTAAAAAATAGAAG
3701 CAACTATAAAGATTTGTAACAGTGGTTGCTATTTTCTTTACCACGAGACT
3751 AGTTAACAGGCTGTATTAAAAGATCTTTTCTTGAATTAAATATTTTCAAT
3801 TTGATTAAACATACCTCAGCCATAAAGGCAAGCACATTTAATTTATACTA
3851 TGGGAATTTGAATAATTGTTACTGAAGAAGCTCTACCAACAAAAAGTTTA
3901 TAGAGCTAGCATATTTAGTCAAGAGATAAAGAGGGTTGTTAGGATACATG
3951 TGCTATTTGAAAGGTATTTATAAAGAAGAGTATATTTATTAAAATTGCT
4001 CAGAACATCCAAATTTCAAGTTTATCATTTATCTTACAATATTTCAAAAA
4051 TATTAAAATAGATACATGAAATACAGAAGTAAATTAAAGAGAAAGTATTT
4101 TATTTTGTAAAAAAAAATTCTAGGTTGGACAGGGAGTACCAGGAAACAAA
4151 AAACAATGAAAAATGTGATCTGACAGAAATTATAGCTCAAAGTATAGTAG
4201 TCAGTAATGAAATGGCTTAAAAATTGGCATATAAAATGCTAATTATAAAA
4251 TAAACAAAATGTAATAATACCCTCCCTACATGTAATGAACTCTGAGTATT
4301 ATACTCTTTTTTGAAGTCTTGACAATGAAAATTTATTTAGACTTTTATAG
4351 ACATCTTGGATAAAGTAAAACAAATTACGAATTAGCATCCATGAGAAAAA
4401 TATAGAAAAATTTCTTAATGTAGTTTGCAAATCTGGGGATTGAAGATGTG
4451 TGTCAAGAGATTGTGATGGCAGACATTTTTTTTCAGACTATAAAATGCAC
4501 AAACAACCATTTAATACATTTTGGTCAAAAATAGTATGTATTTTATTTTA
4551 TGCTACAGGAGAGTAGTCTAAAGTAGGACTGGGCAGAGATCTGACACCCT
4601 GGTAATCACCGAGAGATAGTACACAGTCTCTGTAGAGAAAATAAGCATAG
4651 TGTATGATCTCTAAAATTATGTGGACAAAGGGGAGATAACATTAGGCATG
4701 TGGGGATGAAGACTGAGTACAGAAGAACAATCTAGTCAGTCCAAGAAAAC
4751 ATGTGGATCAATGGAACAAATAGAAGAAATGCTAAAATGAAACAGAAGTC
4801 TTACTGGAAATAAAAGATATGAGGAAGACAAACATTCATGAAAATCACTT
4851 AGTTTAGTAGAGAAAAGATAAAAATAAAGTATTACCTTCTTCTTCATATA
4901 CATTGTTTGATCAGATGCCCCTCAATAAAACTGAGTCTCCAACAGAACTG
4951 AAACTTTAATATTTTGTTCACTGCTCTAATCCCAGAATCTAAGACATATC
5001 TGGCAATAAAAATTAATAAATAAATATTTTAATAAGTAAATCAATCACTT
5051 TAATTTTTCTGTAAGTATCTGTAACTTCTCTTCTGTCTTTCCAAAAAACA
5101 CTCATAAGTACTGTGAATAAGATGAAAAGAGTGAAATAAGATATAGGCTG
5151 TTAGCTGAAAACATCTGGATGGCTGGCAGTGAAACATTAACTTGAAATGT
```

Figure 5C

```
5201  AAGATTAATGAGTAATAGTAAATTTTAACCTTGGCCGTATGATAAAATGT
5251  CTATTAATATTTTTCTAAAATACAGGGCTTTTTGTTTTTGCCATGAGGTT
5301  TGCAGGATCTTGGTTCCCTGATGAGGGATCAAACCTGGGCTCCCCTGGAA
5351  GCACGGAGTCTTAGATATTTGTATTATACACTATCTTTGGTTTCTTTTAA
5401  AGGGAAGTAATTCTACTTAAATAAGAAAATAGATTGACAAGTAATACACT
5451  ATTTCCTCATCTTCCCATTCCCAGGAATTGAGAGCCATGAAGGTCCTCAT
5501  CCTTGCCTGCCTGGTGGCTCTGGCCCTTGCAAGAGAGGTAAATACAGAAA
5551  AAATGTTGAAATAAATAAGACTAGTACTATCTGCTATGTGTAGAAAATTC
5601  ATTACCAACATTGTAAATGTATAAATAATGCACAATCTCAGATTTTTTTT
5651  GAATGCTAAGAAAGTCATTTACGTTCATCCACTATCTCAGTAGTATCCTA
5701  TGGGACCACAAGTCTGAGTCTAGTGCTTTCTATAGTATTGTACCATCTGT
5751  ACCATCAATCCCTAAAGAAAAAGAAAATAAACCAATAAGCAACAGACTA
5801  ACAAGAAGGAACACAGATAAGAACAAAAAGTGAGTAATATTGCATAAATA
5851  CAATTGCATGCATATACAATCTAGATAAATATATCTTATTCCAGTGATGA
5901  AATATTTGTATCCCTTACTGTAGAGTGCTAGGTTTAGCTGTGTCTATTCA
5951  ACACAGGATGATACTCCAGAGGATGGTATATCAGACAACAATAATAAATA
6001  TGTTCATAATTATAATAAAAAGTGTTCAGTAAAAATTAAAATAACTCCTT
6051  TTCTGTTACCCATAAAAACTCTTCATTAAAGTAAAACAAAAATATACTAA
6101  TGAAAGTTACTAAATTTAAAAGACTCTCAAAAGACATATAACATTTTTAT
6151  TTTTCAGATTTGTGAAATAGATAGCTCTGAATAAAGCAAGTAAAAATTAG
6201  GTAGGAAATATTTAATAATGAGTTGACTGTGGGAACTAAAGTGTTTTTT
6251  TTTCTCTTTAGCTGGAAGAACTCAATGTACCTGGTGAGGTAAGATATTTT
6301  TATACAAAGAAAAAAATTAATTTAACTGTAAAATAGTAACAGTCTCTAAT
6351  GATCTGGCAGAAGACTCAGCTAATTGTCAATTTTTATTTTTCCTTTATAG
6401  ATTGTGGAAAGCCTTTCAAGCAGTGAGGTAAGATAGTGTTCATTCAGAGG
6451  CAATTCCCAAATTTAGAGCAATAAAATGCTGTATTATCTTTTTGTGTTA
6501  CATTAATGGCAACCCACTCCAGTATTCTTGCCTGGAAAATCCCATAGAGG
6551  AGGAGCCTGGTAGGCTGCAGTCCACGGGGTCGCTAAGAGTCGGACAGGAC
6601  TGAGCGACTTCCCTTTCACTTTTCACTTTCATGCCTTGGAGAAGGAAATG
6651  GCAACCCACTCCAGTTTTCTTGCCGGGAGAATCCCAGGGACGGGGGAGCC
6701  TGGTGGGCTGCCGTCTATGGGGGTCGCACAGAGTTGGACACGACTGAAGC
6751  GACTTAGCAGTAGCAGCAGCAGGACAGTTAAGGTTTCTCTAATAGCTCAG
6801  TTGGTAAAGAATCTGCCTGCAGTGCAGGAGGACCCTGGGTTCGATTCCTC
6851  AAGATCTGCAGGAGAAGGGATAGGCTACCCATTCCAGTGTTCTTTAAGCC
6901  AATGTGGCTATGTACTGACGGGTAACTATTGTCAATTTCCACTCTGTATA
6951  TTTAAAGGAATAAATGTGTAGAAGGTTTAATATTCTAGTAATTTCTAAAT
7001  GGGTTTGTTATTTGAAATTGTGTCATTGTGCCCTGCTTTTTTTCCTTAAT
7051  GAACTGTACAGTCCTCTTTTCTGTCTTGAACTTTCTATGTTAACCTCCTT
7101  CCATGCTTTGGCATTTATTGAGCACTTTCTGTTTCAGACTTTGACTAGGA
7151  ACTGCAGTACAAACTAGAAAGAGGGATGCCCTTTGTAAAGTGTGAGCAGA
7201  CATGCAAATGGACATATTTTATTATTATACAAGCAATCCAGTACACAAGA
7251  GGCAGTGAGAATGAGTGTAGTCCTAAATCTGCCTGGTGGAATGAGGTAGA
7301  TAATAACCCTATGCCACTCTTTTTGGCTCTGTCATCAGCTGTTGGTTAAA
7351  TAGTGCATCAATATACTTTGTCTCTTCACAAAGGTCAAAAGATGCTGCTG
7401  CTGCTGCTAAGTCGCTTCAGTCATGTCCGACTCTGTGCGACCTCATAGAT
7451  GGCAGCCTGCCAGGCTCCCCCATCCCTGGGATTCTCCAGGCAAGAATACT
7501  GGAGTGGGTTGCCATTTCCTATTCCAATGCATAAAAGTGAAAAGTGAAAG
7551  TGAAGTCGCTCAGTCGTGTCCGACTCCTAGTGACCCCGTGGACTGCAGCC
7601  TACCAGGCTCCTCCATCCATGGATTTTCCAGGCAAGAGTACTGGAGTGG
7651  GTTGCCATTGCCATCTCCAAAGATCCTTATAGGAGGGTATGTATTTCTTA
7701  TAATTCATTAGAAGCCTAAACATAACCAGGGAACTAAGAATGATTAACAA
7751  GTTCATGCGTGGTTATTATTATATATTTTCAATGACTATTATTCTTTTAG
7801  AACCAGATGAAATATTAGAGATCATTTGTTGTCCTAAGGAGAGAACAGG
7851  ATGATTGAGAGACATGTATGCATGCAAAGTTACTTCAGCCCTTTCCAACT
7901  CTGTATGACCCTATGGACTGTAACCTGCCAGGTTCCTCTGTCTATGGGAT
```

Figure 5D

```
7951   TCTCCAGGCAAGAATACAGGAGTGGGTTGTCATCTCCTCCAGGGCCTAGG
8001   AATTGACCTGCATCTCTTACGTCTCCTGCATTGGCAGGCAGGTTCTTTAC
8051   CACTAGCACCACCTGGAAGCCCGATTAGTATCTGTTAAATGCCTCTTTGA
8101   GTACTATGCTCTCTAATCCTCTTTTTCTTGATTGCATCATCTTTCTTTTT
8151   ATACAACAGCCTTATTCAGAAGAGTGGAACATAAACTTTCAGCCATAAAA
8201   TAATGATATTATCAAATGAGCTGTCCATATTAATCTATTAAATTTCTTCA
8251   TTTTCTGATTTATGTTGACAAATAAGAATTTTTTTAAAGCTAGACCTGA
8301   TTTTATTTTTATTTTTCCAAAGGAATCTATTACACGCATCAATAAGGTAA
8351   AACCCCTCATATTTAAATGTACATTTTTTAAATTTCATGTTTGATTTTT
8401   ATAAACAGCATTTCTTTATGTATTTTTTTTTAACCAGAAAATTGAGAAG
8451   TTTCAGAGTGAGGAACAGCAGCAAACAGAGGTAATTTGTTCACTATGAGT
8501   ATATTTTGAGAAGTATTATGAAACATAACACATAAAAAGATTTATAATAA
8551   TTATGTTCAGTCTAAGAATGGTAATATAAATGTCAGTGCAAGAAATAAAA
8601   ACTTTGACAAAATGAAAATATTTAAAAATATAAACGCATTTTAAAACAC
8651   ATAATCAAATTTCACAGTATAGAATAAATAGCTAAGAATAATTATTGATG
8701   TATTCATTTTACTAATGGTATACCTGGTTTTAATAACTGCATATTAGTAG
8751   GAACATTTCCAGACTAGGGACTGTGATCCCCTTATTCTAATGATGGATAT
8801   GCTGATGAAAGACAGTAGGGTGACAGTGTGGCACTAATCCTCATCTGATC
8851   ATTTATCAGCTGTATAACCTTGGCTCCATGTTTCTCTGTACATCATTTTC
8901   TTCACCTGTAAATTGAGAATATTCATAATTACCCAGAGTTGATGAACTGA
8951   CACACAATGAATATTCAGTGGTTTTATATTATATTTGATAGCTTTTATAC
9001   TCACATTTATGGATGTGTGGAGTTCTAAAAAGTATTTCCATTGCCCAGAT
9051   GAGAGAAGTGAGGTACAGGACAATTGAGTATGCAAATGTGTGACCATACC
9101   ACATAGTTATTAAATAGCAGAACTTGCTTAAAAACAAGGATTTGCGGACA
9151   ATGTAAAATTCTTTCATTATATTACTCTTGTGGTAACATATTTATCTAAT
9201   TATGATATTTAAGCTTTCCTCTTTTATAATTGAAGTTTGATTGTTTGGCA
9251   CTTAGGCCAAATTCTAAATCAAAATGAATTTACAACTTGATGCCTTTGAA
9301   GACTCAAGATTACCACCTTCTACCAAGAGAAGTAGTGCTAGAAGTTGGCC
9351   ATTGTTAAGGAACTCCTTGAATTAAAAAAACACATATTAAGACTTAGTTT
9401   TCATTAAAACAAACAAAAATAAACCTCAGAGTAACTTTTAAAGTCTTTTT
9451   AAAATGGATCTTTCTTTGTTATATGAAACCAGTTTGGACTATTATCCAAA
9501   GTATGTAGCTACCACTCTGCAGGAACTCAGGAAGAGGTGGAATAAGTGTT
9551   GAAATCTCCAAACCCTGATTTCACTTGACTCTCTGATTTCACCTGTGAAG
9601   AAAGTGGGTTAATGAGAAATCCTTCAGTGAGCATTTTACTCATTAGTCTT
9651   CATATGACCCCAATTTCTTAACCAAACCAAATGGAAGATTTCTTTCTCT
9701   CTCTTCACTGAATTATGTTTTAAAAGAGGAGGATAATTCATCATGAATA
9751   ACAATTATAACTGGATTATGGACTCAAAGATTTGTTTTCCTTCTTTCCAG
9801   GATGAACTCCAGGATAAAATCCACCCCTTTGCCCAGACACAGTCTCTAGT
9851   CTATCCCTTCCCTGGACCCATCCATAACAGCCTCCCACAAAACATCCCTC
9901   CTCTTACTCAAACCCCTGTGGTGGTGCCGCCTTTCCTTCAGCCTGAAGTA
9951   ATGGGAGTCTCCAAAGTGAAGGAGGCTATGGCTCCTAAGCACAAAGAAAT
10001  GCCCTTCCCTAAATATCCAGTTGAGCCCTTTACTGAAAGCCAGAGCCTGA
10051  CTCTCACTGATGTTGAAAATCTGCACCTTCCTCTGCCTCTGCTCCAGTCT
10101  TGGATGCACCAGCCTCACCAGCCTCTTCCTCCAACTGTCATGTTTCCTCC
10151  TCAGTCCGTGCTGTCCCTTTCTCAGTCCAAAGTCCTGCCTGTTCCCAGA
10201  AAGCAGTGCCCTATCCCCAGAGAGATATGCCCATTCAGGCCTTTCTGCTG
10251  TACCAGGAGCCTGTACTCGGTCCTGTCCGGGGACCCTTCCCTATTATTGT
10301  AAGTCTAAATTTACTAACTGTGCCTGTTTAACTTCTGATGTTTGTATGAT
10351  ATTCGAGTAATTAAGAGTCCTATAAAAAAATGAATAATGAATGGTTCCAA
10401  AATAAGCATAGCTGAGATTAATGATTGTCAGCATTAGTTATAAATAGAAT
10451  AAGCTGGAGAACCTTCACCTCCCCTCCACCACCAGATCTCAATGTCTAGG
10501  CTTACCCGTGGAGATTCTGATGTAATTGTTCTTTCTATGTAGAAGAAACT
10551  TATTGGGAAGAAATAATATAATGGACTATGATTTAATTGGTCTGTTGAGA
10601  ACCAATTAAATTAGATGAAAGCGATTAAGTACAATAAAGCCAAAATTGAA
10651  TTTGATAATCTCATTTGGCTAAGAATAACAAACCTAAGAAGGTTTGCTAT
```

Figure 5E

```
10701   TTTCTACAATTTTGAAGTTCTCCTTATGCACAATTATTTCACCACATGAC
10751   TCATTTCACATCGTGTTTTTGATATATGAGCATATGAGGGAAAAATACTG
10801   AGATGCTTATTTCAATACTCAGGGAAAATTTATTGCCAAAAGGCAAGAAA
10851   TGTATAATTCATTCACTTATTTTATTTTATTATTTTTTTATTTTTAAGG
10901   TCTAAGAGGATTTCAAAGTGAATGCCCCCTCCTCACTTTTGGTAAGCTTT
10951   AGGATATTGGAGGCAGACTGATCATTTTTATAGTTAATATCTTTTACATT
11001   TCATTTTCCTGGATAAGCCCCAATAGTAGCAATTTCCATCAGTGTACCAG
11051   CTTAAAGATTAATTATAAATTTATTTTCAATGATTGACTGTTATTTACTG
11101   GCCTGAAATTATGTATCTGTTATATTTCAAATAATGCAAAACTGTATATA
11151   TATGGTGTTTACAGATTTGATTGGTTTTCTTTCAATAGCCTATATCCTTA
11201   TTATTGATTGTCATCATTTATAGAAAAAACTGAAAATAATTTCTTATACT
11251   TTTATGTAAACCTGTTAGAGCTTATTTTAAAGATCAACTGCATTCACATT
11301   TCTAATCTAGTCATTATGAGCTTCAATAGTTTTATCTCACTTAAAATATA
11351   TATATTGTCTTTTAATTCATGAGTCAAAATACAATCTCACAGTCCAGATA
11401   TGGGACTTAAAAGGGGGATAGAATATAGTTTTGATATTCTTAACAATACA
11451   CATCCTTTTGTGATCATGATTCAGCAGACATTTAATAAAATGATTCCAAG
11501   TAAGCCGATGTTTGGTCCTAGAGGAATTTTTATAACCTTTAAGAGAAGGC
11551   ATAGCATGGTGTTTTTGTAATAAGATTTCTTTTATGAAAAAGTCACACCA
11601   AAATTGCAAATGGGGGTGAGATGAAGAGTTATAACATATAACTAAATCTA
11651   TGTTTGTTCTCTATTCCACAGAATTGACTGCGACTGGAAATATGGCAACT
11701   TTTCAATCCTTGCATCATGTTACTAAGATAATTTTTAAATGAGTATACAT
11751   GGAACAAAAAATGAAACTTTATTCCTTTATTTATTTTATGCTTTTTCATC
11801   TTAATTTGAATTTGAGTCATAAACTATATATTTCAAAATTTTAATTCAAC
11851   ATTAGCATAAAAGTTCAATTTTAACTTGGAAATATCATGAACATATCAAA
11901   ATATGTATAAAAATAATTTCTGGAATTGTGATTATTATTTCTTTAAGAAT
11951   CTATTTCCTAACCAGTCATTTCAATAAATTAATCCTTAGGCATATTTAAG
12001   TTTTCTTGTCTTTATTATATTTTTTTAATGAAATTGGTCTCTTTATTGT
12051   TAACTTAAATTTATCTTTGATGTTAAAAAGAGCTGTGGAAAATTAAAATT
12101   GGATAGAATTCATCGATATCTAGATCTCGACATCGATAAAATAAAAGATT
12151   TTATTTAGTCTCCAGAAAAAGGGGGAATGAAAGACCCCACCTGTAGGTT
12201   TGGCAAGCTAGCTTAAGTAACGCCATTTTGCAAGGCATGGAAAAATACAT
12251   AACTGAGAATAGAGAAGTTCAGATCAAGGTCAGGAACAGATGGAACAGCT
12301   GAATATGGGCCAAACAGGATATCTGTGGTAAGCAGTTCCTGCCCCGGCTC
12351   AGGGCCAAGAACAGATGGAACAGCTGAATATGGGCCAAACAGGATATCTG
12401   TGGTAAGCAGTTCCTGCCCCGGCTCAGGGCCAAGAACAGATGGTCCCCAG
12451   ATGCGGTCCAGCCCTCAGCAGTTTCTAGAGAACCATCAGATGTTTCCAGG
12501   GTGCCCCAAGGACCTGAAATGACCCTGTGCCTTATTTGAACTAACCAATC
12551   AGTTCGCTTCTCGCTTCTGTTCGCGCGCTTCTGCTCCCCGAGCTCAATAA
12601   AAGAGCCCACAACCCCTCACTCGGGGCGCCAGTCCTCCGATTGACTGAGT
12651   CGCCCGGGTACCCGTGTATCCAATAAACCCTCTTGCAGTTGCATCCGACT
12701   TGTGGTCTCGCTGTTCCTTGGGAGGGTCTCCTCTGAGTGATTGACTACCC
12751   GTCAGCGGGGTCTTTCATT
```

| | |
|---|---|
| 1 – 589 | Moloney Murine Sarcoma Virus 5' LTR |
| 659 – 1468 | Moloney Murine Leukemia Virus Extended Packaging Region |
| 1512 – 2306 | Neomycin Resistance Gene |
| 2656 – 3473 | CMV Immediate/Early Enhancer/Promoter |
| 3495 – 3539 | Bovine β-Casein Exon 1 |
| 3540 – 5474 | Bovine β-Casein Intron 1 |
| 5475 – 5537 | Bovine β-Casein Exon 2 |
| 5538 – 6261 | Bovine β-Casein Intron 2 |

Figure 5F

| | |
|---|---|
| 6262 – 6287 | Bovine β-Casein Exon 3 |
| 6288 – 6400 | Bovine β-Casein Intron 3 |
| 6401 – 6427 | Bovine β-Casein Exon 4 |
| 6428 – 8322 | Bovine β-Casein Intron 4 |
| 8323 – 8346 | Bovine β-Casein Exon 5 |
| 8347 – 8439 | Bovine β-Casein Intron 5 |
| 8440 – 8480 | Bovine β-Casein Exon 6 |
| 8481 – 9800 | Bovine β-Casein Intron 6 |
| 9801 – 10298 | Bovine β-Casein Exon 7 |
| 10299 – 10899 | Bovine β-Casein Intron 7 |
| 10900 – 10941 | Bovine β-Casein Exon 8 |
| 10942 – 11671 | Bovine β-Casein Intron 8 |
| 11672 – 11994 | Bovine β-Casein Exon 9 |
| 11995 – 12111 | Bovine β-Casein 3' Flanking Region |
| 12177 – 12770 | Moloney Murine Leukemia Virus 3' LTR |

Figure 6A
PSMA Construct

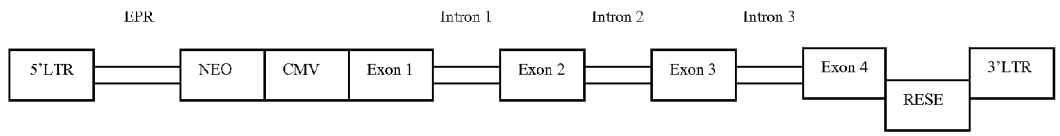

5' LTR=      Moloney murine sarcoma virus 5' long terminal repeat.
EPR=         Moloney murine leukemia virus extended packaging region.
NEO=         Neomycin phosphotransferase gene.
CMV=         Human cytomegalovirus immediate early promoter.
Exon 1=      PSMA antibody exon 1.
Intron 1=    PSMA antibody intron 1.
Exon 2=      PSMA antibody exon 2.
Intron 2=    PSMA antibody intron 2.
Exon 3=      PSMA antibody exon 3.
Intron 3=    PSMA antibody intron 3.
Exon 4=      PSMA antibody exon 4.
RESE=        RNA export and stability element.
3' LTR=      Moloney murine leukemia virus 3' LTR.

SEQ ID NO:5:

```
1GAATT
AATTCATACCAGATCACCGAAAACTGTCCTCCAAATGTGTCCCCCTCACACTCCCAAATTCGCGGGCTTCT
GCCTCTTAGACCACTCTACCCTATTCCCCACACTCACCGGAGCCAAAGCCGCGGCCCTTCCGTTTCTTTGC
TTTTGAAAGACCCCACCCGTAGGTGGCAAGCTAGCTTAAGTAACGCCACTTTGCAAGGCATGGAAAAATAC
ATAACTGAGAATAGAAAAGTTCAGATCAAGGTCAGGAACAAAGAAACAGCTGAATACCAAACAGGATATCT
GTGGTAAGCGGTTCCTGCCCCGGCTCAGGGCCAAGAACAGATGAGACAGCTGAGTGATGGGCCAAACAGGA
TATCTGTGGTAAGCAGTTCCTGCCCCGGCTCGGGGCCAAGAACAGATGGTCCCCAGATGCGGTCCAGCCCT
CAGCAGTTTCTAGTGAATCATCAGATGTTTCCAGGGTGCCCCAAGGACCTGAAAATGACCCTGTACCTTAT
TTGAACTAACCAATCAGTTCGCTTCTCGCTTCTGTTCGCGCGCTTCCGCTCTCCGAGCTCAATAAAAGAGC
CCACAACCCCTCACTCGGCGCGCCAGTCTTCCGATAGACTGCGTCGCCCGGGTACCCGTATTCCCAATAAA
GCCTCTTGCTGTTTGCATCCGAATCGTGGTCTCGCTGTTCCTTGGGAGGGTCTCCTCTGAGTGATTGACTA
CCCACGACGGGGGTCTTTCATTTGGGGGCTCGTCCGGGATTTGGAGACCCCTGCCCAGGGACCACCGACCC
ACCACCGGGAGGTAAGCTGGCCAGCAACTTATCTGTGTCTGTCCGATTGTCTAGTGTCTATGTTTGATGTT
ATGCGCCTGCGTCTGTACTAGTTAGCTAACTAGCTCTGTATCTGGCGGACCCGTGGTGGAACTGACGAGTT
CTGAACACCCGGCCGCAACCCTGGGAGACGTCCCAGGGACTTTGGGGGCCGTTTTTGTGGCCCGACCTGAG
```

Figure 6B

```
GAAGGGAGTCGATGTGGAATCCGACCCCGTCAGGATATGTGGTTCTGGTAGGAGACGAGAACCTAAAACAG
TTCCCGCCTCCGTCTGAATTTTTGCTTTCGGTTTGGAACCGAAGCCGCGCGTCTTGTCTGCTGCAGCGCTG
CAGCATCGTTCTGTGTTGTCTCTGTCTGACTGTGTTTCTGTATTTGTCTGAAAATTAGGGCCAGACTGTTA
CCACTCCCTTAAGTTTGACCTTAGGTCACTGGAAAGATGTCGAGCGGATCGCTCACAACCAGTCGGTAGAT
GTCAAGAAGAGACGTTGGGTTACCTTCTGCTCTGCAGAATGGCCAACCTTTAACGTCGGATGGCCGCGAGA
CGGCACCTTTAACCGAGACCTCATCACCCAGGTTAAGATCAAGGTCTTTTCACCTGGCCCGCATGGACACC
CAGACCAGGTCCCCTACATCGTGACCTGGGAAGCCTTGGCTTTTGACCCCCCTCCCTGGGTCAAGCCCTTT
GTACACCCTAAGCCTCCGCCTCCTCTTCCTCCATCCGCCCCGTCTCTCCCCCTTGAACCTCCTCGTTCGAC
CCCGCCTCGATCCTCCCTTTATCCAGCCCTCACTCCTTCTCTAGGCGCCGGAATTCCGATCTGATCAAGAG
ACAGGATGAGGATCGTTTCGCATGATTGAACAAGATGGATTGCACGCAGGTTCTCCGGCCGCTTGGGTGGA
GAGGCTATTCGGCTATGACTGGGCACAACAGACAATCGGCTGCTCTGATGCCGCCGTGTTCCGGCTGTCAG
CGCAGGGGCGCCCGGTTCTTTTTGTCAAGACCGACCTGTCCGGTGCCCTGAATGAACTGCAGGACGAGGCA
GCGCGGCTATCGTGGCTGGCCACGACGGGCGTTCCTTGCGCAGCTGTGCTCGACGTTGTCACTGAAGCGGG
AAGGGACTGGCTGCTATTGGGCGAAGTGCCGGGGCAGGATCTCCTGTCATCTCACCTTGCTCCTGCCGAGA
AAGTATCCATCATGGCTGATGCAATGCGGCGGCTGCATACGCTTGATCCGGCTACCTGCCCATTCGACCAC
CAAGCGAAACATCGCATCGAGCGAGCACGTACTCGGATGGAAGCCGGTCTTGTCGATCAGGATGATCTGGA
CGAAGAGCATCAGGGGCTCGCGCCAGCCGAACTGTTCGCCAGGCTCAAGGCGCGCATGCCCGACGGCGAGG
ATCTCGTCGTGACCCATGGCGATGCCTGCTTGCCGAATATCATGGTGGAAAATGGCCGCTTTTCTGGATTC
ATCGACTGTGGCCGGCTGGGTGTGGCGGACCGCTATCAGGACATAGCGTTGGCTACCCGTGATATTGCTGA
AGAGCTTGGCGGCGAATGGGCTGACCGCTTCCTCGTGCTTTACGGTATCGCCGCTCCCGATTCGCAGCGCA
TCGCCTTCTATCGCCTTCTTGACGAGTTCTTCTGAGCGGGACTCTGGGGTTCGAAATGACCGACCAAGCGA
CGCCCAACCTGCCATCACGAGATTTCGATTCCACCGCCGCCTTCTATGAAAGGTTGGGCTTCGGAATCGTT
TTCCGGGACGCCGGCTGGATGATCCTCCAGCGCGGGGATCTCATGCTGGAGTTCTTCGCCCACCCCGGGCT
CGATCCCCTCGCGAGTTGGTTCAGCTGCTGCCTGAGGCTGGACGACCTCGCGGAGTTCTACCGGCAGTGCA
AATCCGTCGGCATCCAGGAAACCAGCAGCGGCTATCCGCGCATCCATGCCCCGAACTGCAGGAGTGGGGA
GGCACGATGGCCGCTTTGGTCGAGGCGGATCCGGCCATTAGCCATATTATTCATTGGTTATATAGCATAAA
TCAATATTGGCTATTGGCCATTGCATACGTTGTATCCATATCATAATATGTACATTTATATTGGCTCATGT
CCAACATTACCGCCATGTTGACATTGATTATTGACTAGTTATTAATAGTAATCAATTACGGGTCATTAGT
TCATAGCCCATATATGGAGTTCCGCGTTACATAACTTACGGTAAATGGCCCGCCTGGCTGACCGCCCAACG
ACCCCCGCCCATTGACGTCAATAATGACGTATGTTCCCATAGTAACGCCAATAGGGACTTTCCATTGACGT
CAATGGGTGGAGTATTTACGGTAAACTGCCCACTTGGCAGTACATCAAGTGTATCATATGCCAAGTACGCC
CCCTATTGACGTCAATGACGGTAAATGGCCCGCCTGGCATTATGCCCAGTACATGACCTTATGGGACTTTC
CTACTTGGCAGTACATCTACGTATTAGTCATCGCTATTACCATGGTGATGCGGTTTTGGCAGTACATCAAT
GGGCGTGGATAGCGGTTTGACTCACGGGGATTTCCAAGTCTCCACCCCATTGACGTCAATGGGAGTTTGTT
TTGGCACCAAAATCAACGGGACTTTCCAAAATGTCGTAACAACTCCGCCCCATTGACGCAAATGGGCGGTA
GGCATGTACGGTGGGAGGTCTATATAAGCAGAGCTCGTTTAGTGAACCGTCAGATCGCCTGGAGACGCCAT
CCACGCTGTTTTGACCTCCATAGAAGACACCGGGACCGATCCAGCCTCCGCGGCCCCAAGCTTGGATCTCA
CCATGGAGTTGGGACTGCGCTGGGGCTTCCTCGTTGCTCTTTTAAGAGGTGTCCAGTGTCAGGTGCAATTG
GTGGAGTCTGGGGGAGGCGTGGTCCAGCCTGGGAGGTCCCTGAGACTCTCCTGTGCAGCGTCTGGATTCGC
CTTCAGTAGATATGGCATGCACTGGGTCCGCCAGGCTCCAGGCAAGGGGCTGGAGTGGGTGGCAGTTATAT
GGTATGATGGAAGTAATAAATACTATGCAGACTCCGTGAAGGGCCGATTCACCATCTCCAGAGACAATTCC
AAGAACACGCAGTATCTGCAAATGAACAGCCTGAGAGCCGAGGACACGGCTGTGTATTACTGTGCGAGAGG
CGGTGACTTCCTCTACTACTACTATTACGGTATGGACGTCTGGGGCCAAGGGACCACGGTCACCGTCTCCT
CAGCCTCCACCAAGGGCCCATCGGTCTTCCCCCTGGCACCCTCTAGCAAGAGCACCTCTGGGGGCACAGCG
GCCCTGGGCTGCCTGGTCAAGGACTACTTCCCCGAACCGGTGACGGTGTCGTGGAACTCAGGCGCCCTGAC
CAGCGGCGTGCACACCTTCCCGGCTGTCCTACAGTCCTCAGGACTCTACTCCCTCAGCAGCGTGGTGACCG
TGCCCTCCAGCAGCTTGGGCACCCAGACCTACATCTGCAACGTGAATCACAAGCCCAGCAACACCAAGGTG
GACAAGAGAGTTGGTGAGAGGCCAGCACAGGGAGGGAGGGTGTCTGCTGGAAGCCAGGCTCAGCGCTCCTG
CCTGGACGCATCCCGGCTATGCAGTCCCAGTCCAGGGCAGCAAGGCAGGCCCCGTCTGCCTCTTCACCCGG
AGGCCTCTGCCCGCCCCACTCATGCTCAGGGAGAGGGTCTTCTGGCTTTTTCCCCAGGCTCTGGGCAGGCA
CAGGCTAGGTGCCCCTAACCCAGGCCCTGCACACAAAGGGGCAGGTGCTGGGCTCAGACCTGCCAAGAGCC
ATATCCGGGAGGACCCTGCCCCTGACCTAAGCCCACCCCAAAGGCCAAACTCTCCACTCCCTCAGCTCGGA
CACCTTCTCTCCTCCCAGATTCCAGTAACTCCCAATCTTCTCTCTGCAGAGCCCAAATCTTGTGACAAAAC
TCACACATGCCCACCGTGCCCAGGTAAGCCAGCCCAGGCCTCGCCCTCCAGCTCAAGGCGGGACAGGTGCC
CTAGAGTAGCCTGCATCCAGGGACAGGCCCCAGCCGGGTGCTGACACGTCCACCTCCATCTCTTCCTCAGC
```

Figure 6C

```
ACCTGAACTCCTGGGGGGACCGTCAGTCTTCCTCTTCCCCCAAAACCCAAGGACACCCTCATGATCTCCC
GGACCCCTGAGGTCACATGCGTGGTGGTGGACGTGAGCCACGAAGACCCTGAGGTCAAGTTCAACTGGTAC
GTGGACGGCGTGGAGGTGCATAATGCCAAGACAAAGCCGCGGGAGGAGCAGTACAACAGCACGTACCGTGT
GGTCAGCGTCCTCACCGTCCTGCACCAGGACTGGCTGAATGGCAAGGAGTACAAGTGCAAGGTCTCCAACA
AAGCCCTCCCAGCCCCCATCGAGAAAACCATCTCCAAAGCCAAAGGTGGGACCCGTGGGGTGCGAGGGCCA
CATGGACAGAGGCCGGCTCGGCCCACCCTCTGCCCTGAGAGTGACCGCTGTACCAACCTCTGTCCCTACAG
GGCAGCCCCGAGAACCACAGGTGTACACCCTGCCCCCATCCCGGGAGGAGATGACCAAGAACCAGGTCAGC
CTGACCTGCCTGGTCAAAGGCTTCTATCCCAGCGACATCGCCGTGGAGTGGGAGAGCAATGGGCAGCCGGA
GAACAACTACAAGACCACGCCTCCCGTGCTGGACTCCGACGGCTCCTTCTTCCTCTATAGCAAGCTCACCG
TGGACAAGAGCAGGTGGCAGCAGGGGAACGTCTTCTCATGCTCCGTGATGCATGAGGCTCTGCACAACCAC
TACACGCAGAAGAGCCTCTCCCTGTCTCCGGGTAAATGAGAATTCCTCGAGTTAACAGATCTAGGCCTCCT
AGGTCGACATCGATAATCAACCTCTGGATTACAAAATTTGTGAAAGATTGACTGGTATTCTTAACTATGTT
GCTCCTTTTACGCTATGTGGATACGCTGCTTTAATGCCTTTGTATCATGCTATTGCTTCCCGTATGGCTTT
CATTTTCTCCTCCTTGTATAAATCCTGGTTGCTGTCTCTTTATGAGGAGTTGTGGCCCGTTGTCAGGCAAC
GTGGCGTGGTGTGCACTGTGTTTGCTGACGCAACCCCCACTGGTTGGGGCATTGCCACCACCTGTCAGCTC
CTTTCCGGGACTTTCGCTTTCCCCCTCCCTATTGCCACGGCGGAACTCATCGCCGCCTGCCTTGCCCGCTG
CTGGACAGGGGCTCGGCTGTTGGGCACTGACAATTCCGTGGTGTTGTCGGGGAAATCATCGTCCTTTCCTT
GGCTGCTCGCCTGTGTTGCCACCTGGATTCTGCGCGGGACGTCCTTCTGCTACGTCCCTTCGGCCCTCAAT
CCAGCGGACCTTCCTTCCCGCGGCCTGCTGCCGGCTCTGCGGCCTCTTCCGCGTCTTCGCCTTCGCCCTCA
GACGAGTCGGATCTCCCTTTGGGCCGCCTCCCCGCCTGATCGATAAAATAAAAGATTTTATTTAGTCTCCA
GAAAAGGGGGGAATGAAAGACCCCACCTGTAGGTTTGGCAAGCTAGCTTAAGTAACGCCATTTTGCAAGG
CATGGAAAAATACATAACTGAGAATAGAGAAGTTCAGATCAAGGTCAGGAACAGATGGAACAGCTGAATAT
GGGCCAAACAGGATATCTGTGGTAAGCAGTTCCTGCCCCGGCTCAGGGCCAAGAACAGATGGAACAGCTGA
ATATGGGCCAAACAGGATATCTGTGGTAAGCAGTTCCTGCCCCGGCTCAGGGCCAAGAACAGATGGTCCCC
AGATGCGGTCCAGCCCTCAGCAGTTTCTAGAGAACCATCAGATGTTTCCAGGGTGCCCCAAGGACCTGAAA
TGACCCTGTGCCTTATTTGAACTAACCAATCAGTTCGCTTCTCGCTTCTGTTCGCGCGCTTCTGCTCCCCG
AGCTCAATAAAAGAGCCCACAACCCCTCACTCGGGGCGCCAGTCCTCCGATTGACTGAGTCGCCCGGGTAC
CCGTGTATCCAATAAACCCTCTTGCAGTTGCATCCGACTTGTGGTCTCGCTGTTCCTTGGGAGGGTCTCCT
CTGAGTGATTGACTACCCGTCAGCGGGGGTCTTTCATTTGGGGGCTCGTCCGGGATCGGGAGACCCCTGCC
CAGGGACCACCGACCCACCACCGGGAGGTAAGCTGGCTGCCTCGCGCGTTTCGGTGATGACGGTGAAAACC
TCTGACACATGCAGCTCCCGGAGACGGTCACAGCTTGTCTGTAAGCGGATGCCGGGAGCAGACAAGCCCGT
CAGGGCGCGTCAGCGGGTGTTGGCGGGTGTCGGGGCGCAGCCATGACCCAGTCACGTAGCGATAGCGGAGT
GTATACTGGCTTAACTATGCGGCATCAGAGCAGATTGTACTGAGAGTGCACCATATGCGGTGTGAAATACC
GCACAGATGCGTAAGGAGAAAATACCGCATCAGGCGCTCTTCCGCTTCCTCGCTCACTGACTCGCTGCGCT
CGGTCGTTCGGCTGCGGCGAGCGGTATCAGCTCACTCAAAGGCGGTAATACGGTTATCCACAGAATCAGGG
GATAACGCAGGAAAGAACATGTGAGCAAAAGGCCAGCAAAAGGCCAGGAACCGTAAAAAGGCCGCGTTGCT
GGCGTTTTTCCATAGGCTCCGCCCCCCTGACGAGCATCACAAAAATCGACGCTCAAGTCAGAGGTGGCGAA
ACCCGACAGGACTATAAAGATACCAGGCGTTTCCCCCTGGAAGCTCCCTCGTGCGCTCTCCTGTTCCGACC
CTGCCGCTTACCGGATACCTGTCCGCCTTTCTCCCTTCGGGAAGCGTGGCGCTTTCTCATAGCTCACGCTG
TAGGTATCTCAGTTCGGTGTAGGTCGTTCGCTCCAAGCTGGGCTGTGTGCACGAACCCCCCGTTCAGCCCG
ACCGCTGCGCCTTATCCGGTAACTATCGTCTTGAGTCCAACCCGGTAAGACACGACTTATCGCCACTGGCA
GCAGCCACTGGTAACAGGATTAGCAGAGCGAGGTATGTAGGCGGTGCTACAGAGTTCTTGAAGTGGTGGCC
TAACTACGGCTACACTAGAAGGACAGTATTTGGTATCTGCGCTCTGCTGAAGCCAGTTACCTTCGGAAAAA
GAGTTGGTAGCTCTTGATCCGGCAAACAAACCACCGCTGGTAGCGGTGGTTTTTTTGTTTGCAAGCAGCAG
ATTACGCGCAGAAAAAAAGGATCTCAAGAAGATCCTTTGATCTTTTCTACGGGGTCTGACGCTCAGTGGAA
CGAAAACTCACGTTAAGGGATTTTGGTCATGAGATTATCAAAAAGGATCTTCACCTAGATCCTTTTAAATT
AAAAATGAAGTTTTAAATCAATCTAAAGTATATATGAGTAAACTTGGTCTGACAGTTACCAATGCTTAATC
AGTGAGGCACCTATCTCAGCGATCTGTCTATTTCGTTCATCCATAGTTGCCTGACTCCCCGTCGTGTAGAT
AACTACGATACGGGAGGGCTTACCATCTGGCCCCAGTGCTGCAATGATACCGCGAGACCCACGCTCACCGG
CTCCAGATTTATCAGCAATAAACCAGCCAGCCGGAAGGGCCGAGCGCAGAAGTGGTCCTGCAACTTTATCC
GCCTCCATCCAGTCTATTAATTGTTGCCGGGAAGCTAGAGTAAGTAGTTCGCCAGTTAATAGTTTGCGCAA
CGTTGTTGCCATTGCTGCAGGCATCGTGGTGTCACGCTCGTCGTTTGGTATGGCTTCATTCAGCTCCGGTT
CCCAACGATCAAGGCGAGTTACATGATCCCCATGTTGTGCAAAAAAGCGGTTAGCTCCTTCGGTCCTCCG
ATCGTTGTCAGAAGTAAGTTGGCCGCAGTGTTATCACTCATGGTTATGGCAGCACTGCATAATTCTCTTAC
TGTCATGCCATCCGTAAGATGCTTTTCTGTGACTGGTGAGTACTCAACCAAGTCATTCTGAGAATAGTGTA
```

Figure 6D

```
TGCGGCGACCGAGTTGCTCTTGCCCGGCGTCAACACGGGATAATACCGCGCCACATAGCAGAACTTTAAAA
GTGCTCATCATTGGAAAACGTTCTTCGGGGCGAAAACTCTCAAGGATCTTACCGCTGTTGAGATCCAGTTC
GATGTAACCCACTCGTGCACCCAACTGATCTTCAGCATCTTTTACTTTCACCAGCGTTTCTGGGTGAGCAA
AAACAGGAAGGCAAAATGCCGCAAAAAAGGGAATAAGGGCGACACGGAAATGTTGAATACTCATACTCTTC
CTTTTTCAATATTATTGAAGCATTTATCAGGGTTATTGTCTCATGAGCGGATACATATTTGAATGTATTTA
GAAAAATAAACAAATAGGGGTTCCGCGCACATTTCCCCGAAAAGTGCCACCTGACGTCTAAGAAACCATTA
TTATCATGACATTAACCTATAAAAATAGGCGTATCACGAGGCCCTTTCGTCTTCAA    9291
```

Features:
  1 - 148     LNC plasmid backbone
  149 - 737   Moloney Murine Sarcoma Virus 5' LTR
  807 - 1616  Moloney Murine Leukemia Virus extended packaging region
  1660 - 2454 Neomycin resistance gene coding sequence
  2804 - 3621 CMV immediate early promoter
  3629 - 3631 PSMA antibody heavy chain start codon
  5651 - 5653 PSMA antibody heavy chain stop codon
  5694 - 6297 WPRE (ClaI/ClaI)
  6337 - 6930 Moloney Murine Leukemia Virus 3' LTR
  6931 - 9291 LNC plasmid backbone

Figure 7A
Pro542 Antibody Construct

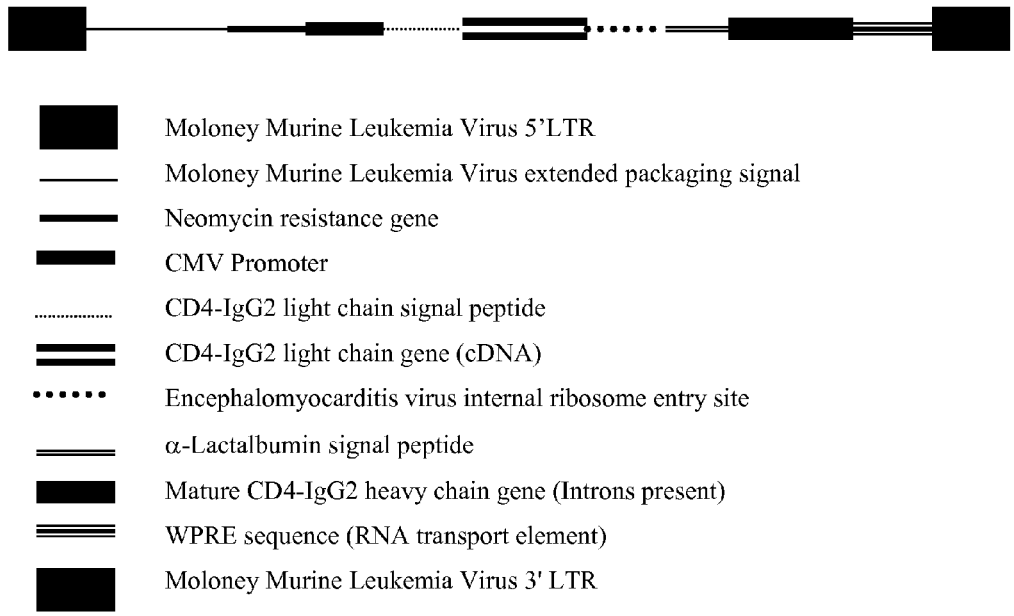

■ Moloney Murine Leukemia Virus 5'LTR

— Moloney Murine Leukemia Virus extended packaging signal

▬ Neomycin resistance gene

■ CMV Promoter

⋯⋯ CD4-IgG2 light chain signal peptide

≡ CD4-IgG2 light chain gene (cDNA)

••••• Encephalomyocarditis virus internal ribosome entry site

= α-Lactalbumin signal peptide

■ Mature CD4-IgG2 heavy chain gene (Introns present)

≡ WPRE sequence (RNA transport element)

■ Moloney Murine Leukemia Virus 3' LTR

SEQ ID NO:6:
1GAATT
AATTCATACCAGATCACCGAAAACTGTCCTCCAAATGTGTCCCCCTCACACTCCCAAATTCGCGGGCTTCT
GCCTCTTAGACCACTCTACCCTATTCCCCACACTCACCGGAGCCAAAGCCGCGGCCCTTCCGTTTCTTTGC
TTTTGAAAGACCCCACCCGTAGGTGGCAAGCTAGCTTAAGTAACGCCACTTTGCAAGGCATGGAAAAATAC
ATAACTGAGAATAGAAAAGTTCAGATCAAGGTCAGGAACAAAGAAACAGCTGAATACCAAACAGGATATCT
GTGGTAAGCGGTTCCTGCCCCGGCTCAGGGCCAAGAACAGATGAGACAGCTGAGTGATGGGCCAAACAGGA
TATCTGTGGTAAGCAGTTCCTGCCCCGGCTCGGGGCCAAGAACAGATGGTCCCCAGATGCGGTCCAGCCCT
CAGCAGTTTCTAGTGAATCATCAGATGTTTCCAGGGTGCCCCAAGGACCTGAAAATGACCCTGTACCTTAT
TTGAACTAACCAATCAGTTCGCTTCTCGCTTCTGTTCGCGCGCTTCCGCTCTCCGAGCTCAATAAAAGAGC
CCACAACCCCTCACTCGGCGCGCCAGTCTTCCGATAGACTGCGTCGCCCGGGTACCCGTATTCCCAATAAA
GCCTCTTGCTGTTTGCATCCGAATCGTGGTCTCGCTGTTCCTTGGGAGGGTCTCCTCTGAGTGATTGACTA
CCCACGACGGGGGTCTTTCATTTGGGGGCTCGTCCGGGATTTGGAGACCCCTGCCCAGGGACCACCGACCC
ACCACCGGGAGGTAAGCTGGCCAGCAACTTATCTGTGTCTGTCCGATTGTCTAGTGTCTATGTTTGATGTT
ATGCGCCTGCGTCTGTACTAGTTAGCTAACTAGCTCTGTATCGGCGGACCCGTGGTGGAACTGACGAGTT
CTGAACACCCGGCCGCAACCCTGGGAGACGTCCCAGGGACTTGGGGGCCGTTTTTGTGGCCCGACCTGAG
GAAGGGAGTCGATGTGGAATCCGACCCCGTCAGGATATGTGGTTCTGGTAGGAGACGAGAACCTAAAACAG
TTCCCGCCTCCGTCTGAATTTTTGCTTTCGGTTTGGAACCGAAGCCGCCGTCTTGTCTGCTGCAGCGCTG
CAGCATCGTTCTGTGTTGTCTCTGTCTGACTGTGTTTCTGTATTTGTCTGAAAATTAGGGCCAGACTGTTA
CCACTCCCTTAAGTTTGACCTTAGGTCACTGGAAAGATGTCGAGCGGATCGCTCACAACCAGTCGGTAGAT
GTCAAGAAGAGACGTTGGGTTACCTTCTGCTCTGCAGAATGGCCAACCTTTAACGTCGGATGGCCGCGAGA
CGGCACCTTTAACCGAGACCTCATCACCCAGGTTAAGATCAAGGTCTTTTCACCTGGCCCGCATGGACACC

Figure 7B

```
CAGACCAGGTCCCCTACATCGTGACCTGGGAAGCCTTGGCTTTTGACCCCCCTCCCTGGGTCAAGCCCTTT
GTACACCCTAAGCCTCCGCCTCCTCTTCCTCCATCCGCCCCGTCTCTCCCCCTTGAACCTCCTCGTTCGAC
CCCGCCTCGATCCTCCCTTTATCCAGCCCTCACTCCTTCTCTAGGCGCCGGAATTCCGATCTGATCAAGAG
ACAGGATGAGGATCGTTTCGCATGATTGAACAAGATGGATTGCACGCAGGTTCTCCGGCCGCTTGGGTGGA
GAGGCTATTCGGCTATGACTGGGCACAACAGACAATCGGCTGCTCTGATGCCGCCGTGTTCCGGCTGTCAG
CGCAGGGGCGCCCGGTTCTTTTTGTCAAGACCGACCTGTCCGGTGCCCTGAATGAACTGCAGGACGAGGCA
GCGCGGCTATCGTGGCTGGCCACGACGGGCGTTCCTTGCGCAGCTGTGCTCGACGTTGTCACTGAAGCGGG
AAGGGACTGGCTGCTATTGGGCGAAGTGCCGGGGCAGGATCTCCTGTCATCTCACCTTGCTCCTGCCGAGA
AAGTATCCATCATGGCTGATGCAATGCGGCGGCTGCATACGCTTGATCCGGCTACCTGCCCATTCGACCAC
CAAGCGAAACATCGCATCGAGCGAGCACGTACTCGGATGGAAGCCGGTCTTGTCGATCAGGATGATCTGGA
CGAAGAGCATCAGGGGCTCGCGCCAGCCGAACTGTTCGCCAGGCTCAAGGCGCGCATGCCCGACGGCGAGG
ATCTCGTCGTGACCCATGGCGATGCCTGCTTGCCGAATATCATGGTGGAAAATGGCCGCTTTTCTGGATTC
ATCGACTGTGGCCGGCTGGGTGTGGCGGACCGCTATCAGGACATAGCGTTGGCTACCCGTGATATTGCTGA
AGAGCTTGGCGGCGAATGGGCTGACCGCTTCCTCGTGCTTTACGGTATCGCCGCTCCCGATTCGCAGCGCA
TCGCCTTCTATCGCCTTCTTGACGAGTTCTTCTGAGCGGGACTCTGGGGTTCGAAATGACCGACCAAGCGA
CGCCCAACCTGCCATCACGAGATTTCGATTCCACCGCCGCCTTCTATGAAAGGTTGGGCTTCGGAATCGTT
TTCCGGGACGCCGGCTGGATGATCCTCCAGCGCGGGGATCTCATGCTGGAGTTCTTCGCCCACCCCGGGCT
CGATCCCCTCGCGAGTTGGTTCAGCTGCTGCCTGAGGCTGGACGACCTCGCGGAGTTCTACCGGCAGTGCA
AATCCGTCGGCATCCAGGAAACCAGCAGCGGCTATCCGCGCATCCATGCCCCCGAACTGCAGGAGTGGGGA
GGCACGATGGCCGCTTTGGTCGAGGCGGATCCGGCCATTAGCCATATTATTCATTGGTTATATAGCATAAA
TCAATATTGGCTATTGGCCATTGCATACGTTGTATCCATATCATAATATGTACATTTATATTGGCTCATGT
CCAACATTACCGCCATGTTGACATTGATTATTGACTAGTTATTAATAGTAATCAATTACGGGGTCATTAGT
TCATAGCCCATATATGGAGTTCCGCGTTACATAACTTACGGTAAATGGCCCGCCTGGCTGACCGCCCAACG
ACCCCCGCCCATTGACGTCAATAATGACGTATGTTCCCATAGTAACGCCAATAGGGACTTTCCATTGACGT
CAATGGGTGGAGTATTTACGGTAAACTGCCCACTTGGCAGTACATCAAGTGTATCATATGCCAAGTACGCC
CCCTATTGACGTCAATGACGGTAAATGGCCCGCCTGGCATTATGCCCAGTACATGACCTTATGGGACTTTC
CTACTTGGCAGTACATCTACGTATTAGTCATCGCTATTACCATGGTGATGCGGTTTTGGCAGTACATCAAT
GGGCGTGGATAGCGGTTTGACTCACGGGGATTTCCAAGTCTCCACCCCATTGACGTCAATGGGAGTTTGTT
TTGGCACCAAAATCAACGGGACTTTCCAAAATGTCGTAACAACTCCGCCCCATTGACGCAAATGGGCGGTA
GGCATGTACGGTGGGAGGTCTATATAAGCAGAGCTCGTTTAGTGAACCGTCAGATCGCCTGGAGACGCCAT
CCACGCTGTTTTGACCTCCATAGAAGACACCGGGACCGATCCAGCCTCCGCGGCCCCAAGCTTGAATTCGG
GAAAGACGCAAGCCCAGAGGCCCTGCCATTTCTGTGGGCTCAGGTCCCTACTGGCTCAGGCCCCTGCCTCC
CTCGGCAAGGCCACAATGAACCGGGAGTCCCTTTTAGGCACTTGCTTCTGGTGCTGCAACTGGCGCTCCT
CCCAGCAGCCACTCAGGGAAAGAAAGTGGTGCTGGGCAAAAAAGGGGATACAGTGGAACTGACCTGTACAG
CTTCCCAGAAGAAGAGCATACAATTCCACTGGAAAAACTCCAACCAGATAAAGATTCTGGGAAATCAGGGC
TCCTTCTTAACTAAAGGTCCATCCAAGCTGAATGATCGCGCTGACTCAAGAAGAAGCCTTTGGGACCAAGG
AAACTTCCCCCTGATCATCAAGAATCTTAAGATAGAAGACTCAGATACTTACATCTGTGAAGTGGAGGACC
AGAAGGAGGAGGTGCAATTGCTAGTGTTCGGATTGACTGCCAACTCTGACACCCACCTGCTTCAGGGGCAG
AGCCTGACCCTGACCTTGGAGAGCCCCCTGGTAGTAGCCCCTCAGTGCAATGTAGGAGTCCAAGGGGTAA
AAACATACAGGGGGGGAAGACCCTCTCCGTGTCTCAGCTGGAGCTCCAGGATAGTGGCACCTGGACATGCA
CTGTCTTGCAGAACCAGAAGAAGGTGGAGTTCAAAATAGACATCGTGGTGCTAGCTTTCACTGTGGCTGCA
CCATCTGTCTTCATCTTCCCGCCATCTGATGAGCAGTTGAAATCTGGAACTGCCTCTGTTGTGTGCCTGCT
GAATAACTTCTATCCCAGAGAGGCCAAAGTACAGTGGAAGGTGGATAACGCCCTCCAATCGGGTAACTCCC
AGGAGAGTGTCACAGAGCAGGACAGCAAGGACACTACAGCCTCAGCAGCACCCTGACGCTGAGCAAA
GCAGACTACGAGAAACACAAAGTCTACGCCTGCGAAGTCACCCATCAGGCCTGAGCTCGCCCGTCACAAA
GAGCTTCAACAGGGGAGAGTGTTAGAGGGAGAAGTGCCCCACCTGCTCCTCAGTTCCAGCCTGACCCCCT
CCCATCCTTTGGCCTCTGACCCTTTTCCACAGGGGACCTACCCCTATTGCGGTCCTCCAGCTCATCTTTC
ACCTCACCCCCTCCTCCTCCTTGGCTTTAGACCTGCAGGCATGCAAGCTTCTCGACGGATCCCCGGGAAT
TCGCCCCTCTCCCTCCCCCCCCCTAACGTTACTGGCCGAAGCCGCTTGGAATAAGGCCGGTGTGCGTTTGT
CTATATGTTATTTTCCACCATATTGCCGTCTTTTGGCAATGTGAGGGCCCGGAAACCTGGCCCTGTCTTCT
TGACGAGCATTCCTAGGGGTCTTTCCCCTCTCGCCAAAGGAATGCAAGGTCTGTTGAATGTCGTGAAGGAA
GCAGTTCCTCTGGAAGCTTCTTGAAGACAAACAACGTCTGTAGCGACCCTTTGCAGGCAGCGGAACCCCCC
ACCTGGCGACAGGTGCCTCTGCGGCCAAAAGCCACGTGTATAAGATACACCTGCAAAGGCGGCACAACCCC
AGTGCCACGTTGTGAGTTGGATAGTTGTGGAAAGAGTCAAATGGCTCTCCTCAAGCGTATTCAACAAGGGG
CTGAAGGATGCCCAGAAGGTACCCCATTGTATGGGATCTGATCTGGGGCCTCGGTGCACATGCTTTACATG
```

Figure 7C

```
TGTTTAGTCGAGGTTAAAAAAACGTCTAGGCCCCCCGAACCACGGGGACGTGGTTTTCCTTTGAAAAACAC
GATGATAATATGGCCTCCTTTGTCTCTCTGCTCCTGGTAGGCATCCTATTCCATGCCACCCAGGCCAAAAA
AGTGGTGCTGGGCAAAAAAGGGGATACAGTGGAACTGACCTGTACAGCTTCCCAGAAGAAGAGCATACAAT
TCCACTGGAAAAACTCCAACCAGATAAGATTCTGGGAAATCAGGGCTCCTTCTTAACTAAAGGTCCATCC
AAGCTGAATGATCGCGCTGACTCAAGAAGAAGCCTTTGGGACCAAGGAAACTTCCCCCTGATCATCAAGAA
TCTTAAGATAGAAGACTCAGATACTTACATCTGTGAAGTGGAGGACCAGAAGGAGGAGGTGCAATTGCTAG
TGTTCGGATTGACTGCCAACTCTGACACCCACCTGCTTCAGGGGCAGAGCCTGACCCTGACCTTGGAGAGC
CCCCCTGGTAGTAGCCCCTCAGTGCAATGTAGGAGTCCAAGGGGTAAAAACATACAGGGGGGGAAGACCCT
CTCCGTGTCTCAGCTGGAGCTCCAGGATAGTGGCACCTGGACATGCACTGTCTTGCAGAACCAGAAGAAGG
TGGAGTTCAAAATAGACATCGTGGTGCTAGCTTTCGCCTCCACCAAGGGCCCATCGGTCTTCCCCCTGGCG
CCCTGCTCCAGGAGCACCTCCGAGAGCACAGCGGCCCTGGGCTGCCTGGTCAAGGACTACTTCCCCGAACC
GGTGACGGTGTCGTGGAACTCAGGCGCTCTGACCAGCGGCGTGCACACCTTCCCAGCTGTCCTACAGTCCT
CAGGACTCTACTCCCTCAGCAGCGTGGTGACCGTGCCCTCCAGCAACTTCGGCACCCAGACCTACACCTGC
AACGTAGATCACAAGCCCAGCAACACCAAGGTGGACAAGACAGTTGGTGAGAGGCCAGCTCAGGGAGGGAG
GGTGTCTGCTGGAAGCCAGGCTCAGCCCTCCTGCCTGGACGCACCCCGGCTGTGCAGCCCCAGCCCAGGGC
AGCAAGGCAGGCCCCATCTGTCTCCTCACCCGGAGGCCTCTGCCCGCCCCACTCATGCTCAGGGAGAGGGT
CTTCTGGCTTTTTCCACCAGGCTCCAGGCAGGCACAGGCTGGGTGCCCCTACCCCAGGCCCTTCACACACA
GGGGCAGGTGCTTGGCTCAGACCTGCCAAAAGCCATATCCGGGAGGACCCTGCCCCTGACCTAAGCCGACC
CCAAAGGCCAAACTGTCCACTCCCTCAGCTCGGACACCTTCTCTCCTCCCAGATCCGAGTAACTCCCAATC
TTCTCTCTGCAGAGCGCAAATGTTGTGTCGAGTGCCCACCGTGCCCAGGTAAGCCAGCCCAGGCCTCGCCC
TCCAGCTCAAGGCGGGACAGGTGCCCTAGAGTAGCCTGCATCCAGGGACAGGCCCCAGCTGGGTGCTGACA
CGTCCACCTCCATCTCTTCCTCAGCACCACCTGTGGCAGGACCGTCAGTCTTCCTCTTCCCCCCAAAACCC
AAGGACACCCTCATGATCTCCCGGACCCCTGAGGTCACGTGCGTGGTGGTGGACGTGAGCCACGAAGACCC
CGAGGTCCAGTTCAACTGGTACGTGGACGGCGTGGAGGTGCATAATGCCAAGACAAAGCCACGGGAGGAGC
AGTTCAACAGCACGTTCCGTGTGGTCAGCGTCCTCACCGTTGTGCACCAGGACTGGCTGAACGGCAAGGAG
TACAAGTGCAAGGTCTCCAACAAAGGCCTCCCAGCCCCCATCGAGAAAACCATCTCCAAAACCAAAGGTGG
GACCCGCGGGGTATGAGGGCCACATGGACAGAGGCCGGCTCGGCCCCACCCTCTGCCCTGGGAGTGACCGCT
GTGCCAACCTCTGTCCCTACAGGGCAGCCCCGAGAACCACAGGTGTACACCCTGCCCCCATCCCGGGAGGA
GATGACCAAGAACCAGGTCAGCCTGACCTGCCTGGTCAAAGGCTTCTACCCCAGCGACATCGCCGTGGAGT
GGGAGAGCAATGGGCAGCCGGAGAACAACTACAAGACCACACCTCCCATGCTGGACTCCGACGGCTCCTTC
TTCCTCTACAGCAAGCTCACCGTGGACAAGAGCAGGTGGCAGCAGGGGAACGTCTTCTCATGCTCCGTGAT
GCATGAGGCTCTGCACAACCACTACACGCAGAAGAGCCTCTCCCTGTCTCCGGGTAAATGAGTGCCACGGC
CGGCAAGCCCCCGCTCGCCTCCTAGGTCGACATCGATAATCAACCTCTGGATTACAAAATTTGTGAAAGAT
TGACTGGTATTCTTAACTATGTTGCTCCTTTTACGCTATGTGGATACGCTGCTTTAATGCCTTTGTATCAT
GCTATTGCTTCCCGTATGGCTTTCATTTTCTCCTCCTTGTATAAATCCTGGTTGCTGTCTCTTTATGAGGA
GTTGTGGCCCGTTGTCAGGCAACGTGGCGTGGTGTGCACTGTGTTTGCTGACGCAACCCCCACTGGTTGGG
GCATTGCCACCACCTGTCAGCTCCTTTCCGGGACTTTCGCTTTCCCCCTCCCTATTGCCACGGCGGAACTC
ATCGCCGCCTGCCTTGCCCGCTGCTGGACAGGGGCTCGGCTGTTGGGCACTGACAATTCCGTGGTGTTGTC
GGGGAAATCATCGTCCTTTCCTTGGCTGCTCGCCTGTGTTGCCACCTGGATTCTGCGCGGGACGTCCTTCT
GCTACGTCCCTTCGGCCCTCAATCCAGCGGACCTTCCTTCCCGCGGCCTGCTGCCGGCTCTGCGGCCTCTT
CCGCGTCTTCGCCTTCGCCCTCAGACGAGTCGGATCTCCCTTTGGGCCGCCTCCCCGCATCGATAAAATAA
AAGATTTTATTTAGTCTCCAGAAAAGGGGGGAATGAAAGACCCCACCTGTAGGTTTGGCAAGCTAGCTTA
AGTAACGCCATTTTGCAAGGCATGGAAAAATACATAACTGAGAATAGAGAAGTTCAGATCAAGGTCAGGAA
CAGATGGAACAGCTGAATATGGGCCAAACAGGATATCTGTGGTAAGCAGTTCCTGCCCCGGCTCAGGGCCA
AGAACAGATGGAACAGCTGAATATGGGCCAAACAGGATATCTGTGGTAAGCAGTTCCTGCCCCGGCTCAGG
GCCAAGAACAGATGGTCCCCAGATGCGGTCCAGCCCTCAGCAGTTTCTAGAGAACCATCAGATGTTTCCAG
GGTGCCCCAAGGACCTGAAATGACCCTGTGCCTTATTTGAACTAACCAATCAGTTCGCTTCTCGCTTCTGT
TCGCGCGCTTCTGCTCCCCGAGCTCAATAAAAGAGCCCACAACCCCTCACTCGGGGCGCCAGTCCTCCGAT
TGACTGAGTCGCCCGGGTACCCGTGTATCCAATAAACCCTCTTGCAGTTGCATCCGACTTGTGGTCTCGCT
GTTCCTTGGGAGGGTCTCCTCTGAGTGATTGACTACCCGTCAGCGGGGGTCTTTCATTTGGGGGCTCGTCC
GGGATCGGGAGACCCCTGCCCAGGGACCACCGACCCACCACCGGGAGGTAAGCTGGCTGCCTCGCGCGTTT
CGGTGATGACGGTGAAAACCTCTGACACATGCAGCTCCCGGAGACGGTCACAGCTTGTCTGTAAGCGGATG
CCGGGAGCAGACAAGCCCGTCAGGGCGCGTCAGCGGGTGTTGGCGGGTGTCGGGGCGCAGCCATGACCCAG
TCACGTAGCGATAGCGGAGTGTATACTGGCTTAACTATGCGGCATCAGAGCAGATTGTACTGAGAGTGCAC
CATATGCGGTGTGAAATACCGCACAGATGCGTAAGGAGAAAATACCGCATCAGGCGCTCTTCCGCTTCCTC
```

Figure 7D

```
GCTCACTGACTCGCTGCGCTCGGTCGTTCGGCTGCGGCGAGCGGTATCAGCTCACTCAAAGGCGGTAATAC
GGTTATCCACAGAATCAGGGGATAACGCAGGAAAGAACATGTGAGCAAAAGGCCAGCAAAAGGCCAGGAAC
CGTAAAAAGGCCGCGTTGCTGGCGTTTTTCCATAGGCTCCGCCCCCTGACGAGCATCACAAAAATCGACG
CTCAAGTCAGAGGTGGCGAAACCCGACAGGACTATAAAGATACCAGGCGTTTCCCCCTGGAAGCTCCCTCG
TGCGCTCTCCTGTTCCGACCCTGCCGCTTACCGGATACCTGTCCGCCTTTCTCCCTTCGGGAAGCGTGGCG
CTTTCTCATAGCTCACGCTGTAGGTATCTCAGTTCGGTGTAGGTCGTTCGCTCCAAGCTGGGCTGTGTGCA
CGAACCCCCCGTTCAGCCCGACCGCTGCGCCTTATCCGGTAACTATCGTCTTGAGTCCAACCCGGTAAGAC
ACGACTTATCGCCACTGGCAGCAGCCACTGGTAACAGGATTAGCAGAGCGAGGTATGTAGGCGGTGCTACA
GAGTTCTTGAAGTGGTGGCCTAACTACGGCTACACTAGAAGGACAGTATTTGGTATCTGCGCTCTGCTGAA
GCCAGTTACCTTCGGAAAAAGAGTTGGTAGCTCTTGATCCGGCAAACAAACCACCGCTGGTAGCGGTGGTT
TTTTTGTTTGCAAGCAGCAGATTACGCGCAGAAAAAAAGGATCTCAAGAAGATCCTTTGATCTTTTCTACG
GGGTCTGACGCTCAGTGGAACGAAAACTCACGTTAAGGGATTTTGGTCATGAGATTATCAAAAGGATCTT
CACCTAGATCCTTTTAAATTAAAAATGAAGTTTTAAATCAATCTAAAGTATATATGAGTAAACTTGGTCTG
ACAGTTACCAATGCTTAATCAGTGAGGCACCTATCTCAGCGATCTGTCTATTTCGTTCATCCATAGTTGCC
TGACTCCCCGTCGTGTAGATAACTACGATACGGGAGGGCTTACCATCTGGCCCCAGTGCTGCAATGATACC
GCGAGACCCACGCTCACCGGCTCCAGATTTATCAGCAATAAACCAGCCAGCCGGAAGGGCCGAGCGCAGAA
GTGGTCCTGCAACTTTATCCGCCTCCATCCAGTCTATTAATTGTTGCCGGGAAGCTAGAGTAAGTAGTTCG
CCAGTTAATAGTTTGCGCAACGTTGTTGCCATTGCTGCAGGCATCGTGGTGTCACGCTCGTCGTTTGGTAT
GGCTTCATTCAGCTCCGGTTCCCAACGATCAAGGCGAGTTACATGATCCCCCATGTTGTGCAAAAAAGCGG
TTAGCTCCTTCGGTCCTCCGATCGTTGTCAGAAGTAAGTTGGCCGCAGTGTTATCACTCATGGTTATGGCA
GCACTGCATAATTCTCTTACTGTCATGCCATCCGTAAGATGCTTTTCTGTGACTGGTGAGTACTCAACCAA
GTCATTCTGAGAATAGTGTATGCGGCGACCGAGTTGCTCTTGCCCGGCGTCAACACGGGATAATACCGCGC
CACATAGCAGAACTTTAAAAGTGCTCATCATTGGAAAACGTTCTTCGGGGCGAAAACTCTCAAGGATCTTA
CCGCTGTTGAGATCCAGTTCGATGTAACCCACTCGTGCACCCAACTGATCTTCAGCATCTTTTACTTTCAC
CAGCGTTTCTGGGTGAGCAAAAACAGGAAGGCAAAATGCCGCAAAAAAGGGAATAAGGGCGACACGGAAAT
GTTGAATACTCATACTCTTCCTTTTTCAATATTATTGAAGCATTTATCAGGGTTATTGTCTCATGAGCGGA
TACATATTTGAATGTATTTAGAAAAATAAACAAATAGGGGTTCCGCGCACATTTCCCCGAAAAGTGCCACC
TGACGTCTAAGAAACCATTATTATCATGACATTAACCTATAAAAATAGGCGTATCACGAGGCCCTTTCGTC
TTCAA  11228
```

Features:
1-144         LNC plasmid backbone
145-733       Moloney Murine Sarcoma Virus 5' LTR
803-1612      Moloney Murine Leukemia Virus Extended packaging signal
1656-2450     Neomycin resistance gene coding sequence
2800-3612     CMV immediate early promoter
3713-3787     Pro542 light chain signal peptide
3788-4645     Pro542 light chain
4643-4645     Stop codon for Pro542 light chain
4830-5410     EMCV internal ribosome entry site
5411-5413     α-LA signal peptide start codon
5465-5467     α-LA signal peptide ending codon
5468-5470     First codon encoding mature Pro542 heavy chain
6299          End of Pro542 exon 1
6300-6691     Pro542 Intron 1
6692-6727     Pro542 Exon 2
6728-6845     Pro542 Intron 2
6846-7172     Pro542 Exon 3
7173-7269     Pro542 Intron 3

Figure 7E

| | |
|---|---|
| 7270-7589 | Pro542 Exon 4 |
| 7590-7592 | Pro542 heavy chain stop codon |
| 7636-8230 | WPRE sequence |
| 8274-8867 | Moloney Murine Leukemia Virus 3' LTR |
| 8868-11228 | LNC plasmid backbone |

Figure 8A
SEQ ID NO:7

```
1    ATGAACCGGGGAGTCCCTTTTAGGCACTTGCTTCTGGTGCTGCAACTGGCGCTCCTCCCAGCAGCCA
     CTCAGGGAAAGAAAGTGGTGCTGGGCAAAAAAGGGGATACAGTGGAACTGACCTGTACAGCTTCCCAGAAG
     AAGAGCATACAATTCCACTGGAAAAACTCCAACCAGATAAAGATTCTGGGAAATCAGGGCTCCTTCTTAAC
     TAAAGGTCCATCCAAGCTGAATGATCGCGCTGACTCAAGAAGAAGCCTTTGGGACCAAGGAAACTTCCCCC
     TGATCATCAAGAATCTTAAGATAGAAGACTCAGATACTTACATCTGTGAAGTGGAGGACCAGAAGGAGGAG
     GTGCAATTGCTAGTGTTCGGATTGACTGCCAACTCTGACACCCACCTGCTTCAGGGGCAGAGCCTGACCCT
     GACCTTGGAGAGCCCCCCTGGTAGTAGCCCCTCAGTGCAATGTAGGAGTCCAAGGGGTAAAAACATACAGG
     GGGGGAAGACCCTCTCCGTGTCTCAGCTGGAGCTCCAGGATAGTGGCACCTGGACATGCACTGTCTTGCAG
     AACCAGAAGAAGGTGGAGTTCAAAATAGACATCGTGGTGCTAGCTTTCACTGTGGCTGCACCATCTGTCTT
     CATCTTCCCGCCATCTGATGAGCAGTTGAAATCTGGAACTGCCTCTGTTGTGCCTGCTGAATAACTTCT
     ATCCCAGAGAGGCCAAAGTACAGTGGAAGGTGGATAACGCCCTCCAATCGGGTAACTCCCAGGAGAGTGTC
     ACAGAGCAGGACAGCAAGGACAGCACCTACAGCCTCAGCAGCACCCTGACGCTGAGCAAAGCAGACTACGA
     GAAACACAAAGTCTACGCCTGCGAAGTCACCCATCAGGGCCTGAGCTCGCCCGTCACAAAGAGCTTCAACA
     GGGGAGAGTGTTAGAGGGAGAAGTGCCCCCACCTGCTCCTCAGTTCCAGCCTGACCCCCTCCCATCCTTTG
     GCCTCTGACCCTTTTTCCACAGGGGACCTACCCCTATTGCGGTCCTCCAGCTCATCTTTCACCTCACCCCC
     CTCCTCCTCCTTGGCTTTAGACCTGCAGGCATGCAAGCTTCTCGACGGATCCCCGGGAATTCGCCCCTCTC
     CCTCCCCCCCCCTAACGTTACTGGCCGAAGCCGCTTGGAATAAGGCCGGTGTGCGTTTGTCTATATGTTAT
     TTTCCACCATATTGCCGTCTTTTGGCAATGTGAGGGCCCGGAAACCTGGCCCTGTCTTCTTGACGAGCATT
     CCTAGGGGTCTTTCCCCTCTCGCCAAAGGAATGCAAGGTCTGTTGAATGTCGTGAAGGAAGCAGTTCCTCT
     GGAAGCTTCTTGAAGACAAACAACGTCTGTAGCGACCCTTTGCAGGCAGCGGAACCCCCCACCTGGCGACA
     GGTGCCTCTGCGGCCAAAAGCCACGTGTATAAGATACACCTGCAAAGGCGGCACAACCCCAGTGCCACGTT
     GTGAGTTGGATAGTTGTGGAAAGAGTCAAATGGCTCTCCTCAAGCGTATTCAACAAGGGGCTGAAGGATGC
     CCAGAAGGTACCCCATTGTATGGGATCTGATCTGGGGCCTCGGTGCACATGCTTTACATGTGTTTAGTCGA
     GGTTAAAAAAACGTCTAGGCCCCCCGAACCACGGGGACGTGGTTTTCCTTTGAAAAACACGATGATAATAT
     GGCCTCCTTTGTCTCTCTGCTCCTGGTAGGCATCCTATTCCATGCCACCCAGGCCAAAAAAGTGGTGCTGG
     GCAAAAAAGGGGATACAGTGGAACTGACCTGTACAGCTTCCCAGAAGAAGAGCATACAATTCCACTGGAAA
     AACTCCAACCAGATAAAGATTCTGGGAAATCAGGGCTCCTTCTTAACTAAAGGTCCATCCAAGCTGAATGA
     TCGCGCTGACTCAAGAAGAAGCCTTTGGGACCAAGGAAACTTCCCCCTGATCATCAAGAATCTTAAGATAG
     AAGACTCAGATACTTACATCTGTGAAGTGGAGGACCAGAAGGAGGAGGTGCAATTGCTAGTGTTCGGATTG
     ACTGCCAACTCTGACACCCACCTGCTTCAGGGGCAGAGCCTGACCCTGACCTTGGAGAGCCCCCCTGGTAG
     TAGCCCCTCAGTGCAATGTAGGAGTCCAAGGGGTAAAAACATACAGGGGGGGAAGACCCTCTCCGTGTCTC
     AGCTGGAGCTCCAGGATAGTGGCACCTGGACATGCACTGTCTTGCAGAACCAGAAGAAGGTGGAGTTCAAA
     ATAGACATCGTGGTGCTAGCTTTCGCCTCCACCAAGGGCCCATCGGTCTTCCCCCTGGCGCCCTGCTCCAG
     GAGCACCTCCGAGAGCACAGCGGCCCTGGGCTGCCTGGTCAAGGACTACTTCCCCGAACCGGTGACGGTGT
     CGTGGAACTCAGGCGCTCTGACCAGCGGCGTGCACACCTTCCCAGCTGTCCTACAGTCCTCAGGACTCTAC
     TCCCTCAGCAGCGTGGTGACCGTGCCCTCCAGCAACTTCGGCACCCAGACCTACACCTGCAACGTAGATCA
     CAAGCCCAGCAACACCAAGGTGGACAAGACAGTTGAGCGCAAATGTTGTGTCGAGTGCCCACCGTGCCCAG
     CACCACCTGTGGCAGGACCGTCAGTCTTCCTCTTCCCCCCAAAACCCAAGGACACCCTCATGATCTCCCGG
     ACCCCTGAGGTCACGTGCGTGGTGGTGGACGTGAGCCACGAAGACCCCGAGGTCCAGTTCAACTGGTACGT
     GGACGGCGTGGAGGTGCATAATGCCAAGACAAAGCCACGGGAGGAGCAGTTCAACAGCACGTTCCGTGTGG
     TCAGCGTCCTCACCGTTGTGCACCAGGACTGGCTGAACGGCAAGGAGTACAAGTGCAAGGTCTCCAACAAA
     GGCCTCCCAGCCCCCATCGAGAAAACCATCTCCAAAACCAAAGGGCAGCCCCGAGAACCACAGGTGTACAC
     CCTGCCCCCATCCCGGGAGGAGATGACCAAGAACCAGGTCAGCCTGACCTGCCTGGTCAAAGGCTTCTACC
     CCAGCGACATCGCCGTGGAGTGGGAGAGCAATGGGCAGCCGGAGAACAACTACAAGACCACACCTCCCATG
     CTGGACTCCGACGGCTCCTTCTTCCTCTACAGCAAGCTCACCGTGGACAAGAGCAGGTGGCAGCAGGGGAA
     CGTCTTCTCATGCTCCGTGATGCATGAGGCTCTGCACAACCACTACACGCAGAAGAGCCTCTCCCTGTCTC
     CGGGTAAATGA  3273
```

Figure 8B

| | |
|---|---|
| 1 - 75 | Pro542 light chain signal peptide |
| 76 - 933 | Pro542 light chain |
| 931 - 933 | Stop codon for Pro542 light chain |
| 1118 - 1698 | EMCV internal ribosome entry site |
| 1699 - 1701 | α-LA signal peptide start codon |
| 1753 - 1755 | α-LA signal peptide ending codon |
| 1756 - 1758 | First codon encoding mature Pro542 heavy chain (cDNA) |
| 3271 - 3273 | Pro542 heavy chain stop codon (cDNA) |

RETROVIRUS-BASED GENOMIC SCREENING

This application claims priority to provisional patent application Ser. No. 60/368,396, filed Mar. 28, 2002.

FIELD OF THE INVENTION

The present invention relates to the expression and screening of genomic DNA sequences encoding uncharacterized genes and proteins.

BACKGROUND OF THE INVENTION

The sequencing of the human and other genomes has ushered in the age of functional genomics. A huge amount of resources are being devoted to analysis of these genomes. The drug discovery process is currently undergoing a fundamental revolution as it embraces functional genomics, that is, high throughput genome- or gene-based biology. This approach is rapidly superseding earlier approaches based on positional cloning. A phenotype (e.g., a biological function or genetic disease) is identified and then tracked back to the responsible gene, based on its genetic map position.

Functional genomics relies heavily on the various tools of bioinformatics to identify gene sequences of potential interest from the many molecular biology databases now available. There is a continuing need to identify and characterize further genes and their related polypeptides/proteins, as targets for drug discovery.

Most of the current methods used to mine data from sequence information rely on computer algorithms. These algorithms are designed to identify a variety of features in DNA sequences, including open reading frames of putative gene coding sequences. Once an open reading frame is identified, algorithms are utilized to provide putative protein sequences based on the presence of start and stop codons. These algorithms also attempt to define splice signals and thus excise exons from the sequences.

However, these algorithms, no matter how powerful, cannot replicate the actual expression and processing of genes. The algorithms may fail to identify all expressed genes. In particular, splice variants and genes expressed from alternative start sites may be missed the algorithms. Accordingly, what is needed in the art are biologically based methods of screening large amounts of genomic sequence data in a high-throughput fashion.

SUMMARY OF THE INVENTION

The present invention relates to the expression and screening of genomic DNA sequences encoding uncharacterized proteins.

Accordingly, in some embodiment, the present invention provides a process for analyzing genomic DNA clones comprising providing at least one vector and at least one packaging cell, wherein the at least one vector comprises retroviral 5' and 3' long terminal repeats flanking a genomic DNA sequence; introducing the at least one vector into the at least one packaging cell under conditions such that a RNA molecule corresponding to the retroviral 5' and 3' long terminal repeats flanking a genomic DNA sequence is transcribed and packaged into a retroviral particle; transducing a cell line having a genome with the retroviral particle under conditions such that the RNA molecule corresponding to the retroviral 5' and 3' long terminal repeats flanking a genomic DNA sequence is reverse transcribed and inserted into the genome of the cell line as a provirus; and analyzing the provirus. In some embodiments, the at least one packaging cell is a 293GP cell. In some embodiments, the retroviral particle is a pseudotyped retroviral particle. In some embodiments, the cell line is selected from the group including, but not limited to, 293 cells, CHO cells, 3T3 cells, and 208F cells. In some embodiments, the at least one vector is selected from the group including, but not limited to, plasmid, cosmid, yeast artificial chromosome, and bacterial artificial chromosome vectors. In some embodiments, the genomic DNA sequence is from about 5 kilobases to about 200 kilobases in length. In other embodiments, the genomic DNA sequence is from about 10 kilobases to about 200 kilobases in length. In still further embodiments, the genomic DNA sequence is from about 50 kilobases to 100 kilobases in length. In some embodiments, the analyzing of the provirus further comprises sequencing the provirus to provide a sequenced provirus. In some embodiments, the sequenced provirus is compared to the genomic DNA sequence to determine exon and intron boundaries. In certain embodiments, multiple proviruses are sequenced and compared to identify splice variants. In other embodiments, the analyzing of the provirus comprises amplification with PCR primers.

The present invention further provides a process for analyzing polypeptides encoded by genomic DNA comprising providing at least one vector and at least one packaging cell, wherein the at least one vector comprises retroviral 5' and 3' long terminal repeats flanking a genomic DNA sequence; introducing the at least one vector into the at least one packaging cell under conditions such that a RNA molecule corresponding to the retroviral 5' and 3' long terminal repeats flanking a genomic DNA sequence is transcribed and packaged into a retroviral particle; transducing a cell line having a genome with the retroviral particle under conditions such that the RNA molecule corresponding to the retroviral 5' and 3' long terminal repeats flanking a genomic DNA sequence is reverse transcribed and inserted into the genome of the cell line as a provirus; and analyzing the expression of polypeptides from the provirus. In some embodiments, the at least one packaging cell is a 293GP cell line. In some embodiments, the retroviral particle is a pseudotyped retroviral particle. In some embodiments, the cell line is selected from the group including, but not limited to, 293 cells, CHO cells, 3T3 cells, and 208F cells. In some embodiments, the at least one vector is selected from the group including, but not limited to, plasmid, cosmid, yeast artificial chromosome, and bacterial artificial chromosome vectors. In some embodiments, the genomic DNA sequence is from about 5 kilobases to about 200 kilobases in length. In other embodiments, the genomic DNA sequence is from about 10 kilobases to about 200 kilobases in length. In still further embodiments, the genomic DNA sequence is from about 50 kilobases to 100 kilobases in length. In some embodiments, the analyzing further comprises electrophoretic comparison of transduced and non-transduced cells.

The present invention additionally provides a process for identifying genomic DNA sequences that encode genes comprising providing a vector and a packaging cell, wherein the vector comprises retroviral 5' and 3' long terminal repeats flanking a genomic DNA sequence; and introducing the vector into the cell under conditions such that a RNA molecule corresponding to the retroviral 5' and 3' long terminal repeats flanking a genomic DNA sequence is transcribed and packaged into a retroviral particle; wherein packaging is indicative of the presence of a coding sequence in the genomic DNA. In some embodiments, the packaging cell line is a 293GP cell line. In some embodiments, the retroviral particle is a pseudotyped retroviral particle. In some embodiments, the line is selected from the group including, but not limited to, of 293 cells, CHO cells, 3T3 cells, and 208F cells. In some embodiments, the vector is selected from the group consisting of plasmid, cosmid, yeast artificial chromosome, and bacterial artificial chromosome vectors. In some embodiments, the genomic DNA sequence is from about 5 kilobases to about 200 kilobases in length. In other embodiments, the genomic DNA sequence is from about 10 kilobases to about 200 kilobases in length. In still further embodiments, the genomic DNA sequence is from about 50 kilobases to 100 kilobases in length.

The present invention further provides a vector comprising a genomic DNA sequence flanked by retroviral 5' and 3' long terminal repeats. In some embodiments, the genomic DNA sequence is from about 10 to 200 kilobases in length. In other embodiments, the genomic DNA sequence is from about 20 to 150 kilobases in length. In still further embodiments, the genomic DNA sequence is from about 50 to 100 kilobases in length. In some embodiments, the vector is selected from the group including, but not limited to, plasmid, cosmid, yeast artificial chromosome, and bacterial artificial chromosome vectors. In some embodiments, the retroviral 5' and 3' long terminal repeats are selected from the group consisting of Moloney murine sarcoma virus and Moloney murine leukemia virus long terminal repeats.

In still further embodiments, the present invention provides a vector library comprising a plurality of genomic DNA sequences flanked by retroviral 5' and 3' long terminal repeats, wherein the plurality of genomic DNA sequences are from about 10 to 200 kilobases in length. In some embodiments, the plurality of genomic DNA sequences are from about 20 to 150 kilobases in length. In certain embodiments, the plurality of genomic DNA sequences are from about 50 to 100 kilobases in length. In some embodiments, the vectors are selected from the group including, but not limited to, plasmid, cosmid, yeast artificial chromosome, and bacterial artificial chromosome vectors. In some embodiments, the retroviral 5' and 3' long terminal repeats are selected from the group including, but not limited to, Moloney murine sarcoma virus and Moloney murine leukemia virus long terminal repeats. In some embodiments, the vector library comprises vectors encoding more than 100 independent genomic DNA sequences. In certain embodiments, the vector library comprises vectors encoding more than 1000 independent genomic DNA sequences. In other embodiments, the vector library comprises vectors encoding more than 10,000 independent genomic DNA sequences. In some embodiments, the present invention provides a packaging cell line comprising the vector described herein. In other embodiments, the present invention provides a packaging cell line comprising the vector library.

In yet other embodiments, the present invention provides a process for producing a retroviral particle comprising providing a vector and a packaging cell, wherein the vector comprises retroviral 5' and 3' long terminal repeats flanking a genomic DNA sequence; introducing the vector into the cell under conditions such that a RNA molecule corresponding to the retroviral 5' and 3' long terminal repeats flanking a genomic DNA sequence is transcribed and packaged into a retroviral particle. In some embodiments, the packaging cell line is a 293GP cell line. In some embodiments, the retroviral particle is a pseudotyped retroviral particle. In some embodiments, the line is selected from the group including, but not limited to, 293 cells, CHO cells, 3T3 cells, and 208F cells. In some embodiments, the vector is selected from the group including, but not limited to, plasmid, cosmid, yeast artificial chromosome, and bacterial artificial chromosome vectors. In some embodiments, the genomic DNA sequence is from about 5 kilobases to about 200 kilobases in length. In other embodiments, the genomic DNA sequence is from about 10 kilobases to about 200 kilobases in length. In still further embodiments, the genomic DNA sequence is from about 50 kilobases to 100 kilobases in length. In some embodiments, the present invention provides a retroviral particle produced by the process described herein. In other embodiments, the present invention provides a host cell transduced with the retroviral particle.

The present invention further provides a retroviral particle comprising a genome, the genome comprising 5' and 3' viral long terminal repeats flanking an exogenous RNA sequence, wherein the exogenous RNA sequence comprises an intron. In some embodiments, the intron is a naturally occurring intron. In some embodiments, the present invention provides a host cell transduced with the retroviral particle.

The present invention also provides a host cell comprising a provirus comprising 5' and 3' viral long terminal repeats flanking an exogenous DNA sequence, wherein the exogenous DNA sequence comprises an intron.

The present invention additionally provides a method of removing introns from genomic DNA, comprising providing a vector and a packaging cell, wherein the vector comprises retroviral 5' and 3' long terminal repeats flanking a genomic DNA sequence comprising one or more introns; introducing the vector into the cell under conditions such that a RNA molecule corresponding to said retroviral 5' and 3' long terminal repeats flanking a genomic DNA sequence is transcribed and packaged into a retroviral particle; wherein the RNA molecule lacks introns.

DESCRIPTION OF THE FIGURES

FIG. 1 provides a schematic diagram of the gene construct identified by SEQ ID NO:1.

FIG. 2 provides the sequence corresponding to SEQ ID NO:1.

FIG. 5 provides the sequence corresponding to SEQ ID NO:4.

FIG. 6 shows a map and sequence (SEQ ID NO:5) of the PSMA construct.

FIG. 7 shows a map and sequence (SEQ ID NO:6) of the Pro542 construct.

FIG. 8 shows the sequence of the spliced Pro542 construct (SEQ ID NO:7).

DEFINITIONS

Figure 3:
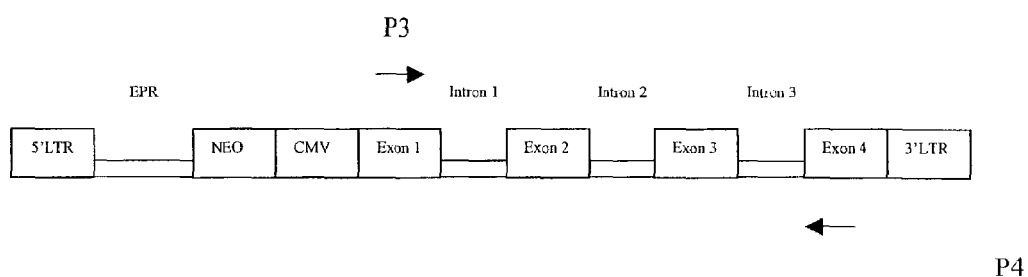
FIG. 3 provides a schematic diagram of the location of PCR primers for the gene construct identified by SEQ ID NO:1.

To facilitate understanding of the invention, a number of terms are defined below.

As used herein, the term "host cell" refers to any eukaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "vector" refers to any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

As used herein, the term "multiplicity of infection" or "MOI" refers to the ratio of integrating vectors:host cells used during transfection or transduction of host cells. For example, if 1,000,000 vectors are used to transduce 100,000 host cells, the multiplicity of infection is 10. The use of this term is not limited to events involving transduction, but instead encompasses introduction of a vector into a host by methods such as lipofection, microinjection, calcium phosphate precipitation, and electroporation.

As used herein, the term "genome" refers to the genetic material (e.g., chromosomes) of an organism.

The term "nucleotide sequence of interest" refers to any nucleotide sequence (e.g., RNA or DNA), the manipulation of which may be deemed desirable for any reason (e.g., genomic DNA segment or sequence, treat disease, confer improved qualities, expression of a protein of interest in a host cell, expression of a ribozyme, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

As used herein, the term "protein of interest" refers to a protein encoded by a nucleic acid of interest.

As used herein, the term "exogenous gene" refers to a gene that is not naturally present in a host organism or cell, or is artificially introduced into a host organism or cell.

The term "gene" refers to a nucleic acid (e.g., DNA or RNA) sequence that comprises coding sequences necessary for the production of a polypeptide or precursor (e.g., proinsulin). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and includes sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' untranslated sequences. The sequences that are located 3' or downstream of the coding region and which are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

As used herein, the terms "nucleic acid molecule encoding," "DNA sequence encoding," "DNA encoding," "RNA sequence encoding," and "RNA encoding" refer to the order or sequence of deoxyribonucleotides or ribonucleotides along a strand of deoxyribonucleic acid or ribonucleic acid. The order of these deoxyribonucleotides or ribonucleotides determines the order of amino acids along the polypeptide (protein) chain. The DNA or RNA sequence thus codes for the amino acid sequence.

As used herein, the term "variant," when used in reference to a protein, refers to proteins encoded by partially homologous nucleic acids so that the amino acid sequence of the proteins varies. As used herein, the term "variant" encompasses proteins encoded by homologous genes having both conservative and nonconservative amino acid substitutions that do not result in a change in protein function, as well as proteins encoded by homologous genes having amino acid substitutions that cause decreased (e.g., null mutations) protein function or increased protein function.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the term "selectable marker" refers to a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk⁻ cell lines, the CAD gene which is used in conjunction with CAD-deficient cells and the mammalian hypoxanthine-guanine phosphoribosyl transferase (hprt) gene which is used in conjunction with hprt⁻ cell lines. A review of the use of selectable markers in mammalian cell lines is provided in Sambrook, J. et al., *Molecular Cloning: A Laboratory Manual*, 2nd ed., Cold Spring Harbor Laboratory Press, New York (1989) pp. 16.9-16.15.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, RNA export elements, internal ribosome entry sites, etc. (defined infra).

Transcriptional control signals in eukaryotes comprise "promoter" and "enhancer" elements. Promoters and enhancers consist of short arrays of DNA sequences that interact specifically with cellular proteins involved in transcription (Maniatis et al., Science 236:1237 [1987]). Promoter and enhancer elements have been isolated from a variety of eukaryotic sources including genes in yeast, insect and mammalian cells, and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see, Voss et al., Trends Biochem. Sci., 11:287 [1986]; and Maniatis et al., supra). For example, the SV40 early gene enhancer is very active in a wide variety of cell types from many mammalian species and has been widely used for the expression of proteins in mammalian cells (Dijkema et al., EMBO J. 4:761 [1985]). Two other examples of promoter/enhancer elements active in a broad range of mammalian cell types are those from the human elongation factor gene (Uetsuki et al., J. Biol. Chem., 264:5791 [1989]; Kim et al., Gene 91:217 [1990]; and Mizushima and Nagata, Nuc. Acids. Res., 18:5322 [1990]) and the long terminal repeats of the Rous sarcoma virus (Gorman et al., Proc. Natl. Acad. Sci. USA 79:6777 [1982]) and the human cytomegalovirus (Boshart et al., Cell 41:521 [1985]).

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques such as cloning and recombination) such that transcription of that gene is directed by the linked enhancer/promoter.

Regulatory elements may be tissue specific or cell specific. The term "tissue specific" as it applies to a regulatory element refers to a regulatory element that is capable of directing selective expression of a nucleotide sequence of interest to a specific type of tissue (e.g., liver) in the relative absence of expression of the same nucleotide sequence of interest in a different type of tissue (e.g., lung).

Tissue specificity of a regulatory element may be evaluated by, for example, operably linking a reporter gene to a promoter sequence (which is not tissue-specific) and to the regulatory element to generate a reporter construct, introducing the reporter construct into the genome of an animal such that the reporter construct is integrated into every tissue of the resulting transgenic animal, and detecting the expression of the reporter gene (e.g., detecting mRNA, protein, or the activity of a protein encoded by the reporter gene) in different tissues of the transgenic animal. The detection of a greater level of expression of the reporter gene in one or more tissues relative to the level of expression of the reporter gene in other tissues shows that the regulatory element is "specific" for the tissues in which greater levels of expression are detected. Thus, the term "tissue-specific" (e.g., liver-specific) as used herein is a relative term that does not require absolute specificity of expression. In other words, the term "tissue-specific" does not require that one tissue have extremely high levels of expression and another tissue have no expression. It is sufficient that expression is greater in one tissue than another. By contrast, "strict" or "absolute" tissue-specific expression is meant to indicate expression in a single tissue type (e.g., liver) with no detectable expression in other tissues.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence that directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one that is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (Sambrook, supra, at 16.6-16.7).

Eukaryotic expression vectors may also contain "viral replicons" or "viral origins of replication." Viral replicons are viral DNA sequences that allow for the extrachromosomal replication of a vector in a host cell expressing the appropriate replication factors. Vectors that contain either the SV40 or polyoma virus origin of replication replicate to high "copy number" (up to $10^4$ copies/cell) in cells that express the appropriate viral T antigen. Vectors that contain the replicons from bovine papillomavirus or Epstein-Barr virus replicate extrachromosomally at "low copy number" (~100 copies/cell). However, it is not intended that expression vectors be limited to any particular viral origin of replication.

As used herein, the term "long terminal repeat" of "LTR" refers to transcriptional control elements located in or isolated from the U3 region 5' and 3' of a retroviral genome. As is known in the art, long terminal repeats may be used as control elements in retroviral vectors, or isolated from the retroviral genome and used to control expression from other types of vectors.

As used herein, the term "retrovirus" refers to a retroviral particle which is capable of entering a cell (i.e., the particle contains a membrane-associated protein such as an envelope protein or a viral G glycoprotein which can bind to the host cell surface and facilitate entry of the viral particle into the cytoplasm of the host cell) and integrating the retroviral genome (as a double-stranded provirus) into the genome of the host cell. The term "retrovirus" encompasses Oncovirinae (e.g., Moloney murine leukemia virus (MoMLV), Moloney murine sarcoma virus (MoMSV), and Mouse mammary tumor virus (MMTV), Spumavirinae, and Lentivirinae (e.g., Human immunodeficiency virus, Simian immunodeficiency virus, Equine infection anemia virus, and Caprine arthritis-encephalitis virus; See, e.g., U.S. Pat. Nos. 5,994,136 and 6,013,516, both of which are incorporated herein by reference).

As used herein, the term "retroviral vector" refers to a retrovirus that has been modified to express a gene of interest. Retroviral vectors can be used to transfer genes efficiently into host cells by exploiting the viral infectious process. Foreign or heterologous genes cloned (i.e., inserted using molecular biological techniques) into the retroviral genome can be delivered efficiently to host cells that are susceptible to infection by the retrovirus. Through well-known genetic manipulations, the replicative capacity of the retroviral genome can be destroyed. The resulting replication-defective vectors can be used to introduce new genetic material to a cell but they are unable to replicate. A helper virus or packaging cell line can be used to permit vector particle assembly and egress from the cell. Such retroviral vectors comprise a replication-deficient retroviral genome containing a nucleic acid sequence encoding at least one gene of interest (i.e., a polycistronic nucleic acid sequence can encode more than one gene of interest), a 5' retroviral long terminal repeat (5' LTR); and a 3' retroviral long terminal repeat (3' LTR).

The term "pseudotyped retroviral vector" refers to a retroviral vector containing a heterologous membrane protein. The term "membrane-associated protein" refers to a protein (e.g., a viral envelope glycoprotein or the G proteins of viruses in the Rhabdoviridae family such as VSV, Piry, Chandipura and Mokola), which is associated with the membrane surrounding a viral particle; these membrane-associated proteins mediate the entry of the viral particle into the host cell. The membrane associated protein may bind to specific cell surface protein receptors, as is the case for retroviral envelope proteins or the membrane-associated protein may interact with a phospholipid component of the plasma membrane of the host cell, as is the case for the G proteins derived from members of the Rhabdoviridae family.

The term "heterologous membrane-associated protein" refers to a membrane-associated protein which is derived from a virus that is not a member of the same viral class or family as that from which the nucleocapsid protein of the vector particle is derived. "Viral class or family" refers to the taxonomic rank of class or family, as assigned by the International Committee on Taxonomy of Viruses.

The term "Rhabdoviridae" refers to a family of enveloped RNA viruses that infect animals, including humans, and plants. The Rhabdoviridae family encompasses the genus *Vesiculovirus*, which includes vesicular stomatitis virus (VSV), Cocal virus, Piry virus, Chandipura virus, and Spring viremia of carp virus (sequences encoding the Spring viremia of carp virus are available under GenBank accession number U18101). The G proteins of viruses in the *Vesiculovirus* genera are virally-encoded integral membrane proteins that form externally projecting homotrimeric spike glycoproteins complexes that are required for receptor binding and membrane fusion. The G proteins of viruses in the *Vesiculovirus* genera have a covalently bound palmititic acid ($C_{16}$) moiety. The amino acid sequences of the G proteins from the *Vesiculoviruses* are fairly well conserved. For example, the Piry virus G protein share about 38% identity and about 55% similarity with the VSV G proteins (several strains of VSV are known, e.g., Indiana, New Jersey, Orsay, San Juan, etc., and their G proteins are highly homologous). The Chandipura virus G protein and the VSV G proteins share about 37% identity and 52% similarity. Given the high degree of conservation (amino acid sequence) and the related functional characteristics (e.g., binding of the virus to the host cell and fusion of membranes, including syncytia formation) of the G proteins of the *Vesiculoviruses*, the G proteins from non-VSV *Vesiculoviruses* may be used in place of the VSV G protein for the pseudotyping of viral particles. The G proteins of the *Lyssa viruses* (another genera within the Rhabdoviridae family) also share a fair degree of conservation with the VSV G proteins and function in a similar manner (e.g., mediate fusion of membranes) and therefore may be used in place of the VSV G protein for the pseudotyping of viral particles. The *Lyssa viruses* include the Mokola virus and the Rabies viruses (several strains of Rabies virus are known and their G proteins have been cloned and sequenced). The Mokola virus G protein shares stretches of homology (particularly over the extracellular and transmembrane domains) with the VSV G proteins which show about 31% identity and 48% similarity with the VSV G proteins. Preferred G proteins share at least 25% identity, preferably at least 30% identity and most preferably at least 35% identity with the VSV G proteins. The VSV G protein from which New Jersey strain (the sequence of this G protein is provided in GenBank accession numbers M27165 and M21557) is employed as the reference VSV G protein.

As used herein, the term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

DETAILED DESCRIPTION OF THE INVENTION

The present invention relates to the expression and screening of genomic DNA sequences encoding uncharacterized genes and proteins. The present invention provides systems utilizing unique features of retroviral replication to analyze uncharacterized genes derived from genomic DNA samples. In preferred embodiments, a segment of genomic DNA is inserted between 5' and 3' viral long terminal repeats (LTRs) in a vector (e.g., a plasmid, cosmid, or artificial chromosome vector). The resulting vector (or library of vectors containing a plurality of independent genomic sequences) is then introduced into a retroviral packaging cell. Once inside the packaging cells, a RNA molecule is transcribed from the 5' LTR. If the RNA molecule encodes a gene having introns, the RNA molecule is processed by the intracellular machinery and introns are removed. In some instances, multiple splice variants are produced. In other instances, one or more introns may be retained in the RNA molecule. The resulting RNA molecule(s) is then packaged into a retroviral particle. The retroviral particles are then used to transduce a host cell. Transduction results in reverse transcription of the RNA molecule into DNA and insertion into the host cell genome as a provirus.

A useful embodiment of the present invention is that the "payload" of the retroviral particle is limited to about 10 kilobases. When relatively large genomic DNA segments (e.g., greater than 10 kilobases) are cloned between the 5' and 3' viral LTRs in the vector, they will not be packaged into retroviral particles unless the RNA is processed by intron removal and splicing. Thus, genomic segments which do not encode genes are not processed and do not contribute to the pool of retroviral particles. Therefore, the systems of the present invention provide a unique method for screening genomic DNA segments for gene encoding sequences.

Another useful embodiment of the present invention is the provision of host cells comprising a provirus that represents a spliced version of the gene encoded by the genomic DNA segment. The provirus can be analyzed by a variety of methods to provide useful information on previously uncharacterized genes. In some embodiments, the provirus (or segments of the provirus encoding the exogenous gene) can be cloned (e.g., by the polymerase chain reaction) and sequenced. The sequence of the gene from the provirus can then be compared to the genomic sequence to define intron and exon boundaries, thus revealing the true sequence of the protein encoded by the gene. Furthermore, multiple proviruses corresponding to the same genomic sequence can be analyzed to identify splice variants, thus identifying multiple forms of a protein. In other embodiments, a library of host cells comprising proviruses can be screened with primers (e.g., non-degenerate or degenerate) primers designed to amplify a specific gene or gene family. Thus, correctly spliced cDNAs encoding a gene or gene family can be isolated from the host cells.

Another useful embodiment of the present invention is that host cell expresses the polypeptide encoded by the exogenous DNA. Therefore, in some other embodiments, the proteins encoded by the exogenous DNA are analyzed directly by immunocytochemistry methods (e.g., Western blotting, immunoprecipitation, ELISA, etc.), mass spectrometry methods, electrophoretic methods, or other methods known in the art.

As can be seen, the present invention provides convenient methods and tools for the analysis of both genomic sequences and the polypeptides encoded by genomic sequences. The invention is described in more detail below in the following sections: I. Sources of Genomic DNA; II. Construction of Retroviral Vector Libraries; III. Transduction of Host Cells with Retroviral Vectors; IV. Analysis of Proviruses; and V. Analysis of Proteins.

I. Sources of Genomic DNA

The systems of the present invention are useful the analysis of genomic DNA segments from any source, including, but not limited to DNA from *Homo sapiens, Mus musculus, Drosophila melanoganster, Rattus rattus,* and *Xenopus laevis.* In general, the genomic DNA is isolated by methods known in the art such as cesium chloride gradient centrifugation or through the use of commercially available kits such as those available from Qiagen (Valencia, Calif.) and Promega (Madison, Wis.). Other methods of purifying genomic DNA are described in Current Protocols in Molecular Biology, 1988, Ed. Ausubel et al., Greene Publish. Assoc. & Wiley Interscience; Sambrook, J. et al., In: Molecular Cloning, A Laboratory Manual, 2nd Ed., Cold Spring Harbor Laboratory Press, Cold Spring Harbor, N.Y. (1989). Once purified genomic DNA is obtained, it is preferably restriction digested with a restriction enzyme that cuts on average of from about every 5,000 to 100,000 base pairs, most preferably from about every 10,000 to 50,000 base pairs. Suitable restriction enzymes include, but are not limited to, BamHI, BglII, EcoRI, HindIII, NotI, PmeI, SalI, and XHO1. In preferred embodiments, the selected restriction enzyme leaves overhangs that are compatible with a multiple cloning site.

II. Vectors and Methods for Transfection

According to the present invention, segments of genomic DNA are cloned between a retroviral 5' and 3' LTRs in a vector. The present invention is not limited to any particular vector. Indeed, the use of a variety of vectors is contemplated, including, but not limited to plasmid, cosmid, and artificial chromosome vectors. The design, production, and use of these vectors in the present invention is described below.

A. Production of Retroviral Vectors

Retroviruses (family Retroviridae) are divided into three groups: the spumaviruses (e.g., human foamy virus); the lentiviruses (e.g., human immunodeficiency virus and sheep visna virus) and the oncoviruses (e.g., MLV, Rous sarcoma virus).

Retroviruses are enveloped (i.e., surrounded by a host cell-derived lipid bilayer membrane) single-stranded RNA viruses that infect animal cells. When a retrovirus infects a cell, its RNA genome is converted into a double-stranded linear DNA form (i.e., it is reverse transcribed). The DNA form of the virus is then integrated into the host cell genome as a provirus. The provirus serves as a template for the production of additional viral genomes and viral mRNAs. Mature viral particles containing two copies of genomic RNA bud from the surface of the infected cell. The viral particle comprises the genomic RNA, reverse transcriptase and other pol gene products inside the viral capsid (which contains the viral gag gene products), which is surrounded by a lipid bilayer membrane derived from the host cell containing the viral envelope glycoproteins (also referred to as membrane-associated proteins).

The organization of the genomes of numerous retroviruses is well known to the art and this has allowed the adaptation of the retroviral genome to produce retroviral vectors. The production of a recombinant retroviral vector carrying a genomic DNA segment is typically achieved in two stages.

First, the genomic DNA segment of interest is inserted into a retroviral vector which contains the sequences necessary for the efficient expression of the genomic DNA segment of interest (including promoter and/or enhancer elements which may be provided by the viral long terminal repeats (LTRs) or by an internal promoter/enhancer and relevant splicing signals), sequences required for the efficient packaging of the viral RNA into infectious virions (e.g., the packaging signal (Psi), the tRNA primer binding site (−PBS), the 3' regulatory sequences required for reverse transcription (+PBS)) and the viral LTRs. The LTRs contain sequences required for the association of viral genomic RNA, reverse transcriptase and integrase functions, and sequences involved in directing the expression of the genomic RNA to be packaged in viral particles. For safety reasons, many recombinant retroviral vectors lack functional copies of the genes that are essential for viral replication (these essential genes are either deleted or disabled); therefore, the resulting virus is said to be replication defective.

Suitable plasmid vectors include, but are not limited to, pLN, pLNCX, pLXSN, and pLXIN. It will be recognized that the elements from the plasmids may also be used to construct cosmid and artificial chromosome vectors, such as yeast artificial chromosomes (YACs), and bacterial artificial chromosomes (BACs, Shizuya et al. 1992, Pro. Natl. Acad. Sci. 89: 8794-8797). In some embodiments of the present invention, these vectors are preferred because they allow cloning of larger segments of genomic DNA. Non-limiting examples of useful vectors are pWE15, SuperCos1 (Stratagene), pDblet (Brun et al. 1995, Gene, 164:173-177), pBluescript (Stratagene), CDM8, pJB8, pYAC3, pYAC4 (see Appendix 5 of Current Protocols in Molecular Biology, 1988, Ed. Ausubel et al., Greene Publish. Assoc. & Wiley Interscience; Sambrook, J. et al., In: Molecular Cloning, A Laboratory Manual, 2nd Ed., Cold Spring Harbor Laboratory Press, Cold Spring Harbor, N.Y. (1989); and U.S. Pat. Nos. 6,162,633 and 5,695,971; all of which are incorporated herein by reference).

In preferred embodiments, the vectors are constructed to include a multiple cloning site between the 5' and 3' LTRs. The multiple cloning site facilitates the cloning of the genomic DNA segments into the vector. In some embodiments, the genomic DNA segment is prepared by enzymatic digestion with a restriction enzyme that cuts on average of from about every 5,000 to 100,000 base pairs, most preferably from about every 10,000 to 50,000 base pairs. Preferably the multiple cloning site of the vector also contains a restriction site for the selected restriction enzyme. In preferred embodiments, the vector is also digested with the selected restriction enzyme and a ligation reaction is performed with the digested genomic DNA, resulting in a library of vectors containing genomic DNA inserts between the 5' and 3' LTRs. In other preferred embodiments, particular genomic DNA segments may be cloned (e.g., by PCR with specific primers) and inserted into the vector. Design of primers containing restriction sites matching restriction sites in the multiple cloning region facilitates cloning of the segments. In other preferred embodiments, families of DNA segments may be cloned (e.g., by PCR with degenerate primers) and inserted between the 3' and 5' LTRs to provide libraries enriched for a particular gene function (e.g., prolactin activity, kinase activity, phosphorylase activity, or protein binding activity).

Second, following construction of the recombinant vector, the vector DNA is introduced into a packaging cell line. Packaging cell lines provide proteins required in trans for the packaging of the viral genomic RNA into viral particles having the desired host range (i.e., the viral-encoded gag, pol and env proteins). The host range is controlled, in part, by the type of envelope gene product expressed on the surface of the viral particle. Packaging cell lines may express ecotrophic, amphotropic or xenotropic envelope gene products. Alternatively, the packaging cell line may lack sequences encoding a viral envelope (env) protein. In this case the packaging cell line will package the viral genome into particles that lack a membrane-associated protein (e.g., an env protein). In order to produce viral particles containing a membrane associated protein that will permit entry of the virus into a cell, the packaging cell line containing the retroviral sequences is transfected with sequences encoding a membrane-associated protein (e.g., the G protein of vesicular stomatitis virus (VSV)). The transfected packaging cell will then produce viral particles that contain the membrane-associated protein expressed by the transfected packaging cell line; these viral particles which contain viral genomic RNA derived from one virus encapsidated by the envelope proteins of another virus are said to be pseudotyped virus particles.

The retroviral vectors of the present invention can be further modified to include additional regulatory sequences. As described above, the retroviral vectors of the present invention include the following elements in operable association: a) a 5' LTR; b) a packaging signal; c) a 3' LTR and d) a genomic DNA segment of interest located between the 5' and 3' LTRs. In some embodiments of the present invention, the nucleic acid of interest may be arranged in opposite orientation to the 5' LTR when transcription from an internal promoter is desired. Suitable internal promoters include, but are not limited to, the alpha-lactalbumin promoter, the CMV promoter (human or ape), and the thymidine kinase promoter.

The retroviral vectors of the present invention may also further comprise a selectable marker allowing selection of transformed cells. A number of selectable markers find use in the present invention, including, but not limited to the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. In some embodiments, the selectable marker gene is provided as part of polycistronic sequence that also encodes the protein of interest.

Viral vectors, including recombinant retroviral vectors, provide a more efficient means of transferring genes into cells as compared to other techniques such as calcium phosphate-DNA co-precipitation or DEAE-dextran-mediated transfection, electroporation or microinjection of nucleic acids. It is believed that the efficiency of viral transfer is due in part to the fact that the transfer of nucleic acid is a receptor-mediated process (i.e., the virus binds to a specific receptor protein on the surface of the cell to be infected). In addition, the virally transferred nucleic acid once inside a cell integrates in controlled manner in contrast to the integration of nucleic acids which are not virally transferred; nucleic acids transferred by other means such as calcium phosphate-DNA co-precipitation are subject to rearrangement and degradation.

The most commonly used recombinant retroviral vectors are derived from the amphotropic Moloney murine leukemia virus (MoMLV) (See e.g., Miller and Baltimore Mol. Cell. Biol. 6:2895 [1986]). The MoMLV system has several advantages: 1) this specific retrovirus can infect many different cell types, 2) established packaging cell lines are available for the production of recombinant MoMLV viral particles and 3) the transferred genes are permanently integrated into the target cell chromosome. The established MoMLV vector systems comprise a DNA vector containing a small portion of the retroviral sequence (e.g., the viral long terminal repeat or "LTR" and the packaging or "psi" signal) and a packaging cell line. The gene to be transferred is inserted into the DNA vector. The viral sequences present on the DNA vector provide the signals necessary for the insertion or packaging of the vector RNA into the viral particle and for the expression of the inserted gene. The packaging cell line provides the proteins required for particle assembly (Markowitz et al., J. Virol. 62:1120 [1988]).

The low titer and inefficient infection of certain cell types by MoMLV-based vectors has been overcome by the use of pseudotyped retroviral vectors that contain the G protein of VSV as the membrane associated protein. Unlike retroviral envelope proteins, which bind to a specific cell surface protein receptor to gain entry into a cell, the VSV G protein interacts with a phospholipid component of the plasma membrane (Mastromarino et al., J. Gen. Virol. 68:2359 [1977]). Because entry of VSV into a cell is not dependent upon the presence of specific protein receptors, VSV has an extremely broad host range. Pseudotyped retroviral vectors bearing the VSV G protein have an altered host range characteristic of VSV (i.e., they can infect almost all species of vertebrate, invertebrate and insect cells). Importantly, VSV G-pseudotyped retroviral vectors can be concentrated 2000-fold or more by ultracentrifugation without significant loss of infectivity (Burns et al. Proc. Natl. Acad. Sci. USA 90:8033 [1993]).

The present invention is not limited to the use of the VSV G protein when a viral G protein is employed as the heterologous membrane-associated protein within a viral particle (See, e.g., U.S. Pat. No. 5,512,421, which is incorporated herein by reference). The G proteins of viruses in the *Vesiculovirus* genera other than VSV, such as the Piry and Chandipura viruses, that are highly homologous to the VSV G protein and, like the VSV G protein, contain covalently linked palmitic acid (Brun et al. Intervirol. 38:274 [1995] and Masters et al., Virol. 171:285 (1990]). Thus, the G protein of the Piry and Chandipura viruses can be used in place of the VSV G protein for the pseudotyping of viral particles. In addition, the VSV G proteins of viruses within the *Lyssa virus* genera such as Rabies and Mokola viruses show a high degree of conservation (amino acid sequence as well as functional conservation) with the VSV G proteins. For example, the Mokola virus G protein has been shown to function in a manner similar to the VSV G protein (i.e., to mediate membrane fusion) and therefore may be used in place of the VSV G protein for the pseudotyping of viral particles (Mebatsion et al., J. Virol. 69:1444 [1995]). Viral particles may be pseudotyped using either the Piry, Chandipura or Mokola G protein as described in Example 2, with the exception that a plasmid containing sequences encoding either the Piry, Chandipura or Mokola G protein under the transcriptional control of a suitable promoter element (e.g., the CMV intermediate-early promoter; numerous expression vectors containing the CMV IE promoter are available, such as the pcDNA3.1 vectors (Invitrogen)) is used in place of pHCMV-G. Sequences encoding other G proteins derived from other members of the Rhabdoviridae family may be used; sequences encoding numerous rhabdoviral G proteins are available from the GenBank database.

The majority of retroviruses can transfer or integrate a double-stranded linear form of the virus (the provirus) into the genome of the recipient cell only if the recipient cell is cycling (i.e., dividing) at the time of infection. Retroviruses that have been shown to infect dividing cells exclusively, or more efficiently, include MLV, spleen necrosis virus, Rous sarcoma virus and human immunodeficiency virus (HIV; while HIV infects dividing cells more efficiently, HIV can infect non-dividing cells).

It has been shown that the integration of MLV virus DNA depends upon the host cell's progression through mitosis and it has been postulated that the dependence upon mitosis reflects a requirement for the breakdown of the nuclear envelope in order for the viral integration complex to gain entry into the nucleus (Roe et al., EMBO J. 12:2099 [1993]). However, as integration does not occur in cells arrested in metaphase, the breakdown of the nuclear envelope alone may not be sufficient to permit viral integration; there may be additional requirements such as the state of condensation of the genomic DNA (Roe et al., supra).

The use of retroviral vectors in the present invention also includes the use of lentivirus based vectors. The lentiviruses (e.g., equine infectious anemia virus, caprine arthritis-encephalitis virus, human immunodeficiency virus) are a subfamily of retroviruses that are able to integrate into non-dividing cells. The lentiviral genome and the proviral DNA have the three genes found in all retroviruses: gag, pol, and env, which are flanked by two LTR sequences. The gag gene encodes the internal structural proteins (e.g., matrix, capsid, and nucleocapsid proteins); the pol gene encodes the reverse transcriptase, protease, and integrase proteins; and the pol gene encodes the viral envelope glycoproteins. The 5' and 3' LTRs control transcription and polyadenylation of the viral RNAs. Additional genes in the lentiviral genome include the vif, vpr, tat, rev, vpu, nef, and vpx genes.

A variety of lentiviral vectors and packaging cell lines are known in the art and find use in the present invention (See, e.g., U.S. Pat. Nos. 5,994,136 and 6,013,516, both of which are herein incorporated by reference). Furthermore, the VSV G protein has also been used to pseudotype retroviral vectors based upon the human immunodeficiency virus (HIV) (Naldini et al., Science 272:263 [1996]). Thus, the VSV G protein may be used to generate a variety of pseudotyped retroviral vectors and is not limited to vectors based on MoMLV. The lentiviral vectors may also be modified as described above to contain various regulatory sequences. After the lentiviral vectors are produced, they may be used to transfect host cells.

III. Transduction of Host Cells with Retroviral Vectors

Once vectors (e.g., retroviral vectors) containing the genomic DNA segments have been produced, they may be used to transduce host cells. Preferably, host cells are transduced with vectors at a multiplicity of infection sufficient to result in the integration of at least 1, and preferably at least 2 or more retroviral vectors. In some embodiments, multiplicities of infection of from 1 to 1,000,000 may be utilized, so that the genomes of the infected host cells contain from 1 to 100 copies of the integrated vectors, and preferably from 1 to 5 copies of the integrated vectors. In other embodiments, a multiplicity of infection of from 10 to 10,000 is utilized. When non-pseudotyped retroviral vectors are utilized for infection, the host cells are incubated with the culture medium from the retroviral producing cells containing the desired titer (i.e., colony forming units, CFUs) of infectious vectors. When pseudotyped retroviral vectors are utilized, the vectors are concentrated to the appropriate titer by ultracentrifugation and then added to the host cell culture. Alternatively, the concentrated vectors can be diluted in a culture medium appropriate for the cell type. Additionally, when expression of more than one genomic DNA segment of interest by the host cell is desired, the host cells can be transfected with multiple vectors each containing a nucleic acid encoding a different genomic DNA segment of interest.

In each case, the host cells are exposed to medium containing the infectious retroviral vectors for a sufficient period of time to allow infection and subsequent integration of the vectors. In general, the amount of medium used to overlay the cells should be kept to as small a volume as possible so as to encourage the maximum amount of integration events per cell. As a general guideline, the number of colony forming units (cfu) per milliliter should be about $10^5$ to $10^7$ cfu/ml, depending upon the number of integration events desired.

The present invention contemplates the transduction of a variety of host cells with the retroviral vectors described above. A number of mammalian host cell lines are known in the art. In general, these host cells are capable of growth and survival when placed in either monolayer culture or in suspension culture in a medium containing the appropriate nutrients and growth factors, as is described in more detail below. Typically, the cells are capable of expressing and secreting large quantities of a particular protein of interest into the culture medium. Examples of suitable mammalian host cells include, but are not limited to Chinese hamster ovary cells (CHO-K1, ATCC CC1-61); bovine mammary epithelial cells (ATCC CRL 10274; bovine mammary epithelial cells); monkey kidney CV1 line transformed by SV40 (COS-7, ATCC CRL 1651); human embryonic kidney line (293 or 293 cells subcloned for growth in suspension culture; see, e.g., Graham et al., J. Gen Virol., 36:59 [1977]); baby hamster kidney cells (BHK, ATCC CCL 10); mouse sertoli cells (TM4, Mather, Biol. Reprod. 23:243-251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 [1982]); MRC 5 cells; FS4 cells; rat fibroblasts (208F cells); MDBK cells (bovine kidney cells); and a human hepatoma line (Hep G2).

IV. Analysis of Vector Particles and Proviruses

The present invention contemplates the analysis of the vector particles produced as described above and proviral forms of the vectors in the host cell. In particularly preferred embodiments, the vector particles and proviruses are analyzed, e.g., to identify intron and exon splice junctions, to identify splice variants resulting from alternative splicing events, and to identify unknown coding sequences.

The methods of the present invention are also utilized to identify the effect of different cell lines on splicing. For example, in some embodiments, the frequency of splice variants in multiple cell lines is determined. In other embodiments, MLV/Gag/Pol constructs are assayed for the effect of different cell lines on splice variants. In preferred embodiments, at least 100 and preferably, at least 1000 different cell lines are analyzed for their effect on splice variants and frequency of splicing of the same construct.

In some embodiments of the present invention, coding sequences are identified by processing of the genomic DNA segments inserted between the 5' and 3' LTRs by cellular splicing machinery. In preferred embodiments, genomic DNA segments that contain coding sequences are transcribed from the packaging vector in the packaging cell. The RNA transcript is then processed by the cellular machinery to remove introns. The RNA transcript is then packaged into a retroviral particle. When the size of the genomic DNA segment is selected to be larger than the payload of the retroviral particle, only transcripts that are processed to remove exons will be packaged. Accordingly, in some embodiments of the invention, the packaging of the transcripts into retroviral particles serves as a screen for genomic DNA segments encoding proteins.

In some preferred embodiments, the retroviral particles are used to transduce host cells as described above. After transduction, a variety of methods can be used to analyze the resulting proviruses. In some preferred embodiments, the DNA of the host cells (either from pooled transduced host cells or clonally selected host cells) is purified and analyzed by sequencing. Because the genomic segments are located between 5' and 3' LTRs of known sequence, sequencing primers can be conveniently designed to sequence from either or both 5' and 3' directions. In preferred embodiments, sequencing is conducted from both the 5' and 3' ends of the processed coding sequence.

In some embodiments of the present invention, the provirus is sequenced by known methods. The sequence of a deoxyribonucleic acid molecule can be elucidated using chemical (Maxam and Gilbert, Proc. Natl. Acad. Sci. USA 74:560 [1977]) or enzymatic (Sanger et al., Proc. Natl. Acad. Sci. USA 74:5463 [1977]) methods. The enzymatic sequencing method is based on the ability of a DNA polymerase to extend a primer hybridized to the template that is to be sequenced until a chain-terminating nucleotide is incorporated (referred to as "chain terminating sequencing"). Each sequence determination is carried out as a set of four separate reactions, each of which contains all four deoxyribonucleoside triphosphates (dNTP) supplemented with a limiting amount of a different dideoxyribonucleoside triphosphate (ddNTP). Because ddNTPs lack the 3'—OH group necessary for chain elongation, the growing oligonucleotide is terminated selectively at G, A, T, or C, depending on the respective dideoxy analog in the reaction.

The relative concentrations of each of the dNTPs and ddNTPs can be adjusted to give a nested set of terminated chains over several hundred to a few thousand bases in length. The resulting fragments, each with a common origin but ending in a different nucleotide, are separated according to size by high-resolution denaturing gel electrophoresis.

Incorporation of a label (e.g., a radiolabel or a fluorescent label) into the oligonucleotide chain permits the visualization of the sequencing products by autoradiography or fluorescence detection. The end-labeled primer protocol, a modification of a described procedure (Heiner et al., Applied Biosystems, Inc. DNA Sequencer Model 370 User Bulletin-Taq Polymerase: Increased Enzyme Versatility in DNA Sequencing [1988]), uses $^{32}$P-ATP, $^{33}$P-ATP or $^{35}$S-ATP to label the sequencing primer. Alternatively, primers containing a fluorescent dye at the 5' terminus may be employed. The DNA template and labeled primer are repeatedly annealed and enzymatically extended/terminated in thermal cycle sequencing. The end-labeled primer protocol is the most versatile sequencing method and is useful when working with lambda DNA (Kaledin et al., Biokhimiya 45:494 [1980]), PCR templates, and any template where false priming may be a problem. This protocol generates sequence data very close to the primer and is recommended when this is needed. The reaction also contains deaza nucleotide mixes that substitute 7-deaza dGTP for dGTP. The deaza mixes resolve band compressions associated with GC-rich regions (Mizusawa et al., Nucl. Acids Res. 14:1319 [1986] and Barr et al., Biotechniques 4:428 [1986]). U.S. Pat. No. 4,707,235 (the disclosure of which is herein incorporated by reference) provides an automated system for the electrophoresis and analysis of radiolabelled products using a multichannel electrophoresis apparatus that is useful in sequencing.

The present invention also contemplates the use thermal cyle sequencing. Thermal cycle sequencing is an alternative method for enzymatic sequence analysis that takes advantage of the intrinsic properties of thermophilic DNA polymerases, such as the one isolated from *Thermus aquaticus* (Taq DNA polymerase). Because the protocol utilizes a thermocycling apparatus, several advantages are realized over conventional sequencing strategies. First, the protocol yields a linear amplification of the template DNA, reducing the amount of template required to achieve a detectable sequence ladder. Using a $^{32}$P end-labeled primer, greater than 500 bases of sequence can be obtained from as little as 4 fmol ($4 \times 10^{-15}$ moles) of template after an overnight exposure. Secondly, the high temperatures employed during each denaturation cycle eliminate the requirement for alkaline denaturation and ethanol precipitation of double-stranded DNA (dsDNA) templates. The denaturation cycles also help to circumvent problems associated with rapid reannealing of linear dsDNA templates such as PCR reaction products. Third, high annealing temperatures increase the stringency of primer hybridization. Fourth, the high polymerization temperature decreases the secondary structure of DNA templates and thus permits polymerization through highly structured regions (Innis et al., Proc. Natl. Acad. Sci USA 85:9436 [1988]). Thermal cycle sequencing is useful for sequencing a wide variety of templates such as recombinant DNA, amplified DNA, large double-stranded DNA templates such as lambda, GC-rich templates and palindrome-rich templates.

In other preferred embodiments, the sequencing is conducted by a shotgun sequencing method. In some embodiments, the shotgun sequencing method can be used either on the transduced host cells with primers designed to hybridize to the conserved portions of the provirus (e.g., the 5' and 3' LTRs). In other embodiments, the retroviral particles produced by the host cells are isolated, the RNA is isolated, and the isolated RNA is reverse transcribed. In the shotgun sequencing method, the genome is randomly fragmented and cloned into sequencing vectors. The resulting clones are sequenced and overlapping sequences are identified and ordered to generate a contiguous sequence. Using this approach, high quality sequence is assembled after very large amounts of sequence data, ranging from five to seven times the amount of raw data to be sequenced, are accumulated. Complete protocols for these and related sequencing steps have been described (Ausubel et al., ed., Current Protocols in Molecular Biology. New York, N.Y.: John Wiley and Sons, 1995; N. J. Dracopoli et al., ed., Current Protocols in Human Genetics. New York: John Wiley and Sons, 1995; Venter et al., Nature 381:364-65 (1996)).

It will readily apparent that the sequencing strategies described above may be combined with PCR amplification of the provirus. As used herein, the term "polymerase chain reaction" ("PCR") refers to the method described in U.S. Pat. Nos. 4,683,195, 4,889,818, and 4,683,202, all of which are hereby incorporated by reference. These patents describe methods for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase (e.g., Taq). The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

In some embodiments, primers specific to the provirus (e.g., directed to the 5' and 3' LTRs) are used to amplify proviral DNA from DNA isolated from transduced host cells. In other preferred embodiments, a RT-PCR protocol is utilized in which RNA is isolated directly from retroviral particles produced by packaging cells and reverse transcribed. The reverse transcribed RNA (i.e., cDNA) is then amplified and utilized for sequencing.

The sequences of the inserts may be analyzed by a variety of bioinformatics methods. In some embodiments, the raw sequence data is analyzed by Phred, Phrap and Consed programs. These programs read DNA sequencer traces, make base calls, assemble the shotgun DNA sequence data and analyze the sequence regions that are likely to contribute to errors. Phred is the initial program used to read the sequencer trace data, call the bases and assign quality values to the bases. Phred uses a Fourier-based method to examine the base traces generated by the sequencer. The output files from Phred are written in FASTA, phd or scf format. Phrap is used to assemble contiguous sequences from only the highest quality portion of the sequence data output by Phred. Phrap is amenable to high-throughput data collection. Finally, Consed is used as a finishing tool to assign error probabilities to the sequence data. Detailed description of the Phred, Phrap and Consed software and its use can be found in the following references: Ewing et al., Genome Res., 8:175 [1998]; Ewing and Green, Genome Res. 8:186 [1998]; Gordon et al., Genome Res. 8: 195 [1998].

In other embodiments, the sequences are compared to public databases and to one another according to BLAST protocols. The BLAST set of programs may be used to compare the large numbers of sequences and obtain homologies to known protein families. These homologies provide information regarding the function of newly sequenced genes. Detailed description of the BLAST software and its uses can be found in the following references: Altschul et al., J. Mol. Biol., 215:403 [1990]; Altschul, J. Mol. Biol. 219: 555 [1991].

Generally, BLAST performs sequence similarity searching and is divided into 5 basic subroutines: (1) BLASTP compares an amino acid sequence to a protein sequence database; (2) BLASTN compares a nucleotide sequence to a nucleic acid sequence database; (3) BLASTX compares translated protein sequences done in 6 frames to a protein sequence database; (4) TBLASTN compares a protein sequence to a nucleotide sequence database that is translated into all 6 reading frames; (5) TBLASTX compares the 6 frame translated protein sequence to the 6-frame translation of a nucleotide sequence database. Subroutines (3)-(5) may be used to identify weak similarities in nucleic acid sequence.

The BLAST program is based on the High Segment Pair (HSP), two sequence fragments of arbitrary but equal length whose alignment is locally maximized and whose alignment meets or exceeds a cutoff threshold. BLAST determines multiple HSP sets statistically using sum statistics. The score of the HSP is then related to its expected chance of frequency of occurrence, E. The value, E, is dependent on several factors such as the scoring system, residue composition of sequences, length of query sequence and total length of database. In the output file will be listed these E values, these are typically in a histogram format, and are useful in determining levels of statistical significance at the user s predefined expectation threshold. Finally, the Smallest Sum Probability, P(N) is the probability of observing the shown matched sequences by chance alone and is typically in the range of 0-1.

BLAST measures sequence similarity using a matrix of similarity scores for all possible pairs of residues and these specify scores for aligning pairs of amino acids. The matrix of choice for a specific use depends on several factors: the length of the query sequence and whether or not a close or distant relationship between sequences is suspected. Several matrices are available including PAM40, PAM120, PAM250, BLOSUM 62 and BLOSUM 50. Altschul et al. (1990) found PAM120 to be the most broadly sensitive matrix (for example point accepted mutation matrix per 100 residues). However, in some cases the PAM120 matrix may not find short but strong or long but weak similarities between sequences. In these cases, pairs of PAM matrices may be used, such as PAM40 and PAM 250, and the results compared. Typically, PAM 40 is used for database searching with a query of 9-21 residues long, while PAM 250 is used for lengths of 47-123.

The BLOSUM (Blocks Substitution Matrix) series of matrices are constructed based on percent identity between two sequence segments of interest. Thus, the BLOSUM62 matrix is based on a matrix of sequence segments in which the members are less than 62% identical. BLOSUM62 shows very good performance for BLAST searching. However, other BLOSUM matrices, like the PAM matrices, may be useful in other applications. For example, BLOSUM45 is particularly strong in profile searching.

In still other embodiments, the sequences are analyzed according to FASTA protocols. The FASTA suite of programs permits the evaluation of DNA and protein similarity based on local sequence alignment. The FASTA search algorithm utilizes Smith/Waterman- and Needleman/Wunsch-based optimization methods. These algorithms consider all of the alignment possibilities between the query sequence and the library in the highest-scoring sequence regions. Further detailed description of the FASTA software and its use can be found in the following reference: Pearson and Lipman, Proc. Natl. Acad. Sci., 85: 2444 [1988].

In still other embodiments, the sequences are analyzed by Pfam protocols. Pfam is a computational method that utilizes a collection of multiple alignments and profile hidden Markov models of protein domain families to classify existing and newly found protein sequences into structural families. Detailed description of the Pfam software and its uses can be found in the following references: Sonhammer et al., Proteins: Structure, Function and Genetics, 28:405 [1997]; Sonhammer et al., Nucleic Acids Res., 26:320 [1998]; Bateman et al., Nucleic Acids Res., 27: 260 [1999].

Pfam 3.1, the latest version, includes 54% of proteins in SWISS_PROT and SP-TrEMBL-5 as a match to the database and includes expectation values for matches. Pfam consists of parts A and B. Pfam-A contains a hidden Markov model and includes curated families. Pfam-B uses the Domainer program to cluster sequence segments not included in Pfam-A. Domainer uses pairwise homology data from Blastp to construct aligned families.

Alternative protein family databases that may be used include PRINTS and BLOCKS, that both are based on a set of ungapped blocks of aligned residues. However, these programs typically contain short conserved regions whereas Pfam represents a library of complete domains that facilitates automated annotation. Comparisons of Pfam profiles may also be performed using genomic and EST data with the programs, Genewise and ESTwise, respectively. Both of these programs allow for introns and frame shifting errors.

The determination of sequence relationships between unknown sequences and those that have been categorized can be problematic because background noise increases with the number of sequences, especially at a low level of similarity detection. One recent approach to this problem has been tested that efficiently detects and confirms weak or distant relationships among protein sequences based on a database of blocks. The BLOCKS database provides multiple alignments of sequences and contains blocks or protein motifs found in known families of proteins.

Other programs such as PRINTS and Prodom also provide alignments, however, the BLOCKS database differs in the manner in which the database was constructed. Construction of the BLOCKS database proceeds as follows: one starts with a group of sequences that presumably have one or motifs in common, such as those from the PROSITE database. The PROTOMAT program then uses a motif finding program to scan sequences for similarity looking for spaced triplets of amino acids. The located blocks are then entered into the MOTOMAT program for block assembly. Weights are computed for all sequences. Following construction of a BLOCKS database one can use BLIMPS to performs searches of the BLOCKS database. Detailed description of the construction and use of a BLOCKS database can be found in the following references: Henikoff, S. and Henikoff, J. G., Genomics, 19:97 [1994]; Henikoff, J. G. and Henikoff, S., Meth. Enz., 266:88 [1996].

The PRINTS database of protein family fingerprints can be used in addition to BLOCKS and PROSITE. These databases are considered to be secondary databases because they diagnose the relationship between sequences that yield function information. Presently, however, it is not recommended that these databases be used alone. Rather, it is strongly suggested that these pattern databases be used in conjunction with each other so that a direct comparison of results can be made to analyze their robustness.

Generally, these programs utilize pattern recognition to discover motifs within protein sequences. However, PRINTS goes one step further, it takes into account not simply single motifs but several motifs simultaneously that might characterize a family signature. Other programs, such as PROSITE, rely on pattern recognition but are limited by the fact that query sequences must match them exactly. Thus, sequences that vary slightly will be missed. In contrast, the PRINTS database fingerprinting approach is capable of identifying distant relatives due to its reliance on the fact that sequences do not have match the query exactly. Instead they are scored according to how well they fit each motif in the signature. Another advantage of PRINTS is that it allows the user to search both PRINTS and PROSITE simultaneously. A detailed description of the use of PRINTS can be found in the following reference: Attwood et al., Nucleic Acids Res. 25: 212 [1997].

V. Analysis of Proteins

In some embodiments of the present invention, the proteins encoded by the vectors described are analyzed. The present invention is not limited to any particular method of protein analysis. Indeed, the use of a number of methods of protein analysis are contemplated, including, but not limited to Western blotting, immunoprecipitation, ELISA, 2-D gel electrophoresis, SDS-PAGE, capillary electrophoresis, isoelectric focusing, gas chromatography (GC), gas mass-mass spectrometry (GC-MS), MALDI-TOF, and combinations thereof. In general, the production of proteins by cells transduced with the vectors described above is compared to the production of proteins by non-transduced cells.

In some particularly preferred embodiments, the production of a protein of interest by cells transfected with a retroviral vector is assayed by Western blotting, immunoprecipitation, or ELISA. In some embodiments, the antibody is directed to a particular protein. In other embodiments, the antibody binds to a class of proteins (e.g., protein kinases, protein phosphatases, transmembrane proteins, secreted proteins, G-protein coupled receptors). It is contemplated that Western blotting may be performed with either one dimensional or two dimensional gels.

In some particularly preferred embodiments, the protein profiles of transduced and non-transduced cells are analyzed by 2-D polyacrylamide gel electrophoresis (2-D PAGE; See e.g. Proteome Research: New Frontiers in Functional Genomics, Wilkins et al., eds., Springer-Verlag, Berlin, 1997). The first dimension of 2-D PAGE is isoelectric focusing (IEF). In this dimension, proteins are separated according to their isoelectric point. In preferred embodiments, this separation is performed using a commercially available immobilized pH gradient (IPG) gel. These gels are formed by co-polymerizing the pH gradient with the acrylamide gel matrix. It is contemplated that use of IPG gels results in greater reproducibility that the use of non-IPG IEF gels. The second dimension is sodium dodecyl sulfate—polyacrylamide gel electrophoresis (SDS-PAGE).

In some embodiments, once the 2-D PAGE is complete, the gels are stained, or transferred to a suitable substrate (e.g., PVDF) and stained. Suitable staining techniques include, but are not limited to, silver staining, detection of radiolabelled proteins (which requires culture of the transduced cells in a medium containing radioactive substrates), Coomassie Blue staining, and staining with fluorescent stains such as SYPRO orange and red. In other embodiments, proteins are labeled with fluorescent stains prior to IEF.

The stained gels are then compared to either control gels or gels in databases (e.g., SWISS-2DPAGE or HSC-2DPAGE databases) to identify novel proteins in the transduced cells. Comparison of protein profiles will identify proteins synthesized from the genomic DNA inserts in the vectors. In some instances only one protein will be synthesized. However, in other instances, multiple new proteins that are the result of alternative splicing or the use of internal start sites will be identified. Furthermore, expression of the protein encoded by the genomic DNA insert may cause the up-regulation, down-regulation, or de novo synthesis of proteins in related metabolic pathways. Identification of these proteins will lead to the identification of the pathway in which the protein of interest operates. Preferably, the comparison is performed by implementing a computer algorithm (e.g., those available from the SWISS-2DPAGE or HSC-2DPAGE databases).

In further preferred embodiments, novel or differently expressed proteins present on the gels are identified. It is contemplated that a variety of protein identification techniques find use in the present invention, including, but not limited to comparison to known protein profiles, known isoelectric points and/or apparent masses, N-terminal or C-terminal microsequencing, and mass spectrometry (e.g., Matrix-Assisted Laser Desorption/Ionization-Time of Flight Mass Spectrometry (MALDI-TOF MS) or peptide mass fingerprinting by MALDI or Electrospray-Ionization Mass Spectrometry (ESI-MS); these approaches are described in Proteome Research: New Frontiers in Functional Genomics, Wilkins et al., eds., Springer-Verlag, Beriln, 1997. In preferred embodiments, N-terminal or C-terminal protein tags are generated by Edman degradation techniques. Generally, tags of from 4-8 amino acids will be sufficient for identification of proteins. In some embodiments, the amino acid sequence data is compared to the nucleotide sequences of the genomic DNA inserts to determine whether the protein corresponds to the insert or has been synthesized as a result of expression of the protein encoded by the genomic DNA insert.

Experimental

The following examples serve to illustrate certain preferred embodiments and aspects of the present invention and are not to be construed as limiting the scope thereof.

In the experimental disclosure which follows, the following abbreviations apply: M (molar); mM (millimolar); µM (micromolar); nM (nanomolar); mol (moles); mmol (millimoles); µmol (micromoles); nmol (nanomoles); gm (grams); mg (milligrams); µg (micrograms); pg (picograms); L (liters); ml (milliliters); µl (microliters); cm (centimeters); mm (millimeters); µm (micrometers); nm (nanometers); ° C. (degrees Centigrade); AMP (adenosine 5'-monophosphate); BSA (bovine serum albumin); cDNA (copy or complimentary DNA); CS (calf serum); DNA (deoxyribonucleic acid); ssDNA (single stranded DNA); dsDNA (double stranded DNA); dNTP (deoxyribonucleotide triphosphate); LH (luteinizing hormone); NIH (National Institues of Health, Besthesda, Md.); RNA (ribonucleic acid); PBS (phosphate buffered saline); g (gravity); OD (optical density); HEPES (N-[2-Hydroxyethyl]piperazine-N-[2-ethanesulfonic acid]); HBS (HEPES buffered saline); PBS (phosphate buffered saline); SDS (sodium dodecylsulfate); Tris-HCl (tris[Hydroxymethyl]aminomethane-hydrochloride); Klenow (DNA polymerase I large (Klenow) fragment); rpm (revolutions per minute); EGTA (ethylene glycol-bis(β-aminoethyl ether) N,N,N',N'-tetraacetic acid); EDTA (ethylenediaminetetraacetic acid); bla (β-lactamase or ampicillin-resistance gene); ORI (plasmid origin of replication); lacI (lac repressor); X-gal (5-bromo-4-chloro-3-indolyl-D-galactoside); ATCC (American Type Culture Collection, Rockville, Md.); GIBCO/BRL (GIBCO/BRL, Grand Island, N.Y.); Perkin-Elmer (Perkin-Elmer, Norwalk, Conn.); and Sigma (Sigma Chemical Company, St. Louis, Mo.).

EXAMPLE 1

Vector Construction

A gene construct was developed to determine if genomic regions of DNA can be placed into retroviral vectors, undergo processing in the cell to splice out introns to create a "cDNA like sequence" and be expressed in a host cell. To create the test vector the genomic clone of the bovine α-lactalbumin was used. α-Lactalbumin is a milk protein that is expressed at high levels in the mammary gland of cattle. The α-lactalbumin gene was placed behind the CMV promoter in the LNC based retroviral backbone. This construct is designated pα-LA. The construct contains all four exons and three introns of the bovine α-lactalbumin gene in addition to a couple hundred bases of 3' flanking region. This region of the gene is approximately 2.3 kb in length. A diagram of the final gene construct is provided in FIG. 1. The sequence (SEQ ID NO:1) of the vector is provided in FIG. 2.

EXAMPLE 2

Generation of Cell Lines Stably Expressing the MoMLV gag and pol Proteins

Examples 2-5 describe the production of pseudotyped retroviral vectors. These methods are generally applicable to the production of the vectors described above and below. The expression of the fusogenic VSV G protein on the surface of cells results in syncytium formation and cell death. Therefore, in order to produce retroviral particles containing the VSV G protein as the membrane-associated protein a two-step approach was taken. First, stable cell lines expressing the gag and pol proteins from MoMLV at high levels were generated (e.g., 293GP$^{SD}$ cells). The stable cell line which expresses the gag and pol proteins produces noninfectious viral particles lacking a membrane-associated protein (e.g., an envelope protein). The stable cell line was then co-transfected, using the calcium phosphate precipitation, with VSV-G and gene of interest plasmid DNAs. The pseudotyped vector generated was used to infect 293GP$^{SD}$ cells to produce stably transformed cell lines. Stable cell lines can be transiently transfected with a plasmid capable of directing the high level expression of the VSV G protein (see below). The transiently transfected cells produce VSV G-pseudotyped retroviral vectors that can be collected from the cells over a period of 3 to 4 days before the producing cells die as a result of syncytium formation.

The first step in the production of VSV G-pseudotyped retroviral vectors, the generation of stable cell lines expressing the MoMLV gag and pol proteins is described below. The human adenovirus Ad-5-transformed embryonal kidney cell line 293 (ATCC CRL 1573) was cotransfected with the pCMVgag-pol and the gene encoding for phleomycin. pCMV gag-pol contains the MoMLV gag and pol genes under the control of the CMV promoter (pCMV gag-pol is available from the ATCC).

The plasmid DNA was introduced into the 293 cells using calcium phosphate co-precipitation (Graham and Van der Eb, Virol. 52:456 [1973]). Approximately 5×10$^5$ 293 cells were plated into a 100 mm tissue culture plate the day before the DNA co-precipitate was added. Stable transformants were selected by growth in DMEM-high glucose medium containing 10% FCS and 10 μg/ml phleomycin (selective medium). Colonies which grew in the selective medium were screened for extracellular reverse transcriptase activity (Goff et al., J. Virol. 38:239 [1981]) and intracellular p30gag expression. The presence of p30gag expression was determined by Western blotting using a goat-anti p30 antibody (NCI antiserum 77S000087). A clone which exhibited stable expression of the retroviral genes was selected. This clone was named 293GP$^{SD}$ (293 gag-pol-San Diego). The 293GP$^{SD}$ cell line, a derivative of the human Ad-5-transformed embryonal kidney cell line 293, was grown in DMEM-high glucose medium containing 10% FCS.

EXAMPLE 3

Preparation of Pseudotyped Retroviral Vectors Bearing the G Glycoprotein of VSV

In order to produce VSV G protein pseudotyped retrovirus the following steps were taken. The 293GP$^{SD}$ cell line was co-transfected with VSV-G plasmid and DNA plasmid of interest. This co-transfection generates the infectious particles used to infect 293GP$^{SD}$ cells to generate the packaging cell lines. This Example describes the production of pseudotyped LNBOTDC virus. This general method may be used to produce any of the vectors described herein.

a) Cell Lines and Plasmids

The packaging cell line, 293GP$^{SD}$ was grown in alpha-MEM-high glucose medium containing 10% FCS. The titer of the pseudo-typed virus may be determined using either 208F cells (Quade, Virol. 98:461 [1979]) or NIH/3T3 cells (ATCC CRL 1658); 208F and NIH/3T3 cells are grown in DMEM-high glucose medium containing 10% CS.

The plasmids utilized were pLBC-L2HCF, pLBC-M4HCF, pLNC-L2LC and pLNC-M4L (See Example 1). The plasmid pHCMV-G contains the VSV G gene under the transcriptional control of the human cytomegalovirus intermediate-early promoter (Yee et al., Meth. Cell Biol. 43:99 [1994]).

b) Production of Stable Packaging Cell Lines, Pseudotyped Vector and Titering of Pseudotyped Vector DNA (SEQ ID NOs: 1, 2, 3, or 4) was co-transfected with pHCMV-G DNA into the packaging line 293GP$^{SD}$ to produce virus. The resulting virus was then used to infect 293GP$^{SD}$ cells to transform the cells. The procedure for producing pseudotyped virus was carried out as described (Yee et al., Meth. Cell Biol. 43:99 [1994].

This is a retroviral gene construct that upon creation of infectious replication defective retroviral vector will cause the insertion of the sequence described above into the cells of interest. The 3' viral LTR provides the poly-adenylation sequence for the mRNA.

Briefly, on day 1, approximately 7×10$^7$ 293GP$^{SD}$ cells were placed in a 75 cm$^2$ tissue culture flask. The flasks were incubated overnight at 37° C., 5.0% CO$_2$.

On the following day (day 2), the media in the 293GP$^{SD}$ flasks were changed with harvest medium 2 hours prior to transfection. 293GP$^{SD}$ cells were then co-transfected with 25 μg of plasmid DNA and 25 μg of VSV-G plasmid DNA using the standard calcium phosphate co-precipitation procedure (Graham and Van der Eb, Virol. 52:456 [1973]). Briefly, pHCMV-G DNA, construct DNA, 1:10 TE, and 2M CaCl$_2$ were combined and mixed. A range of 10 to 40 μg of plasmid DNA was used. 2×HBS (37° C.) was placed into a separate tube. While bubbling air through the 2×HBS, the DNA/1:10 TE/2M CaCl$_2$ mixture was added drop wise. The transfection mixture was allowed to incubate at room temperature for 20 minutes. Following the incubation period, the correct amount of transfection mixture was added to each culture vessel. The plates or flasks were returned to 37° C., 5% CO$_2$ incubator for approximately six hours. Following the incubation period, the transfections were checked for the presence of crystals/precipitate by viewing under an inverted scope. The transfection media was then removed from culture vessels by aspiration with a sterile Pasteur pipet and vacuum pump and fresh harvest medium was added to each culture vessel. The culture vessels were incubated at 37° C., 5% $CO_2$ for 24-72 hr.

On day 3, approximately $7.5 \times 10^5$ 293GP$^{SD}$ cells were placed in a 25 cm$^2$ tissue culture flask 24 hours prior to the harvest of the pseudotyped virus from the transfected 293GP$^{SD}$ cells. On day 4, culture medium was harvested from the transfected 293GP$^{SD}$ cells 48 hours after the application of the plasmid DNA with the gene of interest and VSV-G DNA. The culture medium was filtered through a 0.45 μm filter. The culture medium containing LNBOTDC virus was used to infect the 293GP$^{SD}$ cells as follows. The culture medium was removed from the 293GP$^{SD}$ cells and was replaced with the virus-containing culture medium. Polybrene was added to the medium at a final concentration of 8 μg/ml. The virus-containing medium was allowed to remain on the 293GP$^{SD}$ cells for 24 hours. Following the 16 hour infection period (on day 5), the medium was removed from the 293GP$^{SD}$ cells and was replaced with fresh medium containing 400 μg/ml G418 (GIBCO/BRL). The medium was changed approximately every 3 days until only those colonies that are G418-resistant colonies remain.

The G418-resistant 293GP$^{SD}$ colonies were plated as single cells in 96 wells. Sixty to one hundred G418-resistant colonies were screened for the expression of the BOTDC antibody in order to identify high producing clones. The top 10 clones in 96-well plates were transferred 6-well plates and allowed to grow to confluency.

The top 10 clones were then expanded to screen for high titer production. Based on protein expression and titer production, 5 clonal cell lines were selected. One line was designated the master cell bank and the other 4 as backup cell lines. Pseudotyped vector was generated as follows. Approximately $7 \times 10^7$ 293GP$^{SD}$/cells were placed into a 75 cm$^2$ tissue culture flask. Twenty-four hours later, the cells were transfected with 25 μg of pHCMV-G plasmid DNA using calcium phosphate co-precipitation. Six to eight hours after the calcium-DNA precipitate was applied to the cells, the DNA solution was replaced with fresh culture medium (lacking G418). Longer transfection times (overnight) were found to result in the detachment of the majority of the 293GP$^{SD}$/cells from the plate and are therefore avoided. The transfected 293GP$^{SD}$/cells produce pseudotyped virus.

The pseudotyped virus generated from the transfected 293GP$^{SD}$ cells can be collected at least once a day between 24 and 96 hr after transfection. The highest virus titer was generated approximately 48 to 72 hr after initial pHCMV-G transfection. While syncytium formation became visible about 48 hr after transfection in the majority of the transfected cells, the cells continued to generate pseudotyped virus for at least an additional 48 hr as long as the cells remained attached to the tissue culture plate. The collected culture medium containing the VSV G-pseudotyped virus was pooled, filtered through a 0.45 μm filter and stored at −80° C. or concentrated immediately and then stored at −80° C.

The titer of the VSV G-pseudotyped virus was then determined as follows. Approximately $5 \times 10^5$ rat 208F fibroblasts cells were plated into 6 well plates. Twenty-fours hours after plating, the cells were infected with serial dilutions of the virus-containing culture medium in the presence of 8 μg/ml polybrene. Twenty four hours after infection with virus, the medium was replaced with fresh medium containing 400 μg/ml G418 and selection was continued for 14 days until only G418-resistant colonies remain. Viral titers were typically about 0.5 to $5.0 \times 10^6$ colony forming units (cfu)/ml. The titer of the virus stock could be concentrated to a titer of greater than $10^9$ cfu/ml as described below.

EXAMPLE 4

Concentration of Pseudotyped Retroviral Vectors

The VSV G-pseudotyped viruses were concentrated to a high titer by one cycle of ultracentrifugation. However, two cycles can be performed for further concentration. The culture medium collected and filtered as described in Example 2, which contained pseudotyped virus was transferred to Oakridge centrifuge tubes (50 ml Oakridge tubes with sealing caps, Nalge Nunc International) previously sterilized by autoclaving. The virus was sedimented in a JA20 rotor (Beckman) at 48,000×g (20,000 rpm) at 4° C. for 120 min. The culture medium was then removed from the tubes in a biosafety hood and the media remaining in the tubes was aspirated to remove the supernatant. The virus pellet was resuspended to 0.5 to 1% of the original volume in 0.1×HBSS. The resuspended virus pellet was incubated overnight at 4° C. without swirling. The virus pellet could be dispersed with gentle pipetting after the overnight incubation without significant loss of infectious virus. The titer of the virus stock was routinely increased 100- to 300-fold after one round of ultracentrifugation. The efficiency of recovery of infectious virus varied between 30 and 100%.

The virus stock was then subjected to low speed centrifugation in a microfuge for 5 min at 4° C. to remove any visible cell debris or aggregated virions that were not resuspended under the above conditions. It was noted that if the virus stock is not to be used for injection into oocytes or embryos, this centrifugation step may be omitted.

The virus stock can be subjected to another round of ultracentrifugation to further concentrate the virus stock. The resuspended virus from the first round of centrifugation is pooled and pelleted by a second round of ultracentrifugation that is performed as described above. Viral titers are increased approximately 2000-fold after the second round of ultracentrifugation (titers of the pseudotyped LNBOTDC virus are typically greater than or equal to $1 \times 10^9$ cfu/ml after the second round of ultracentrifugation).

The titers of the pre- and post-centrifugation fluids were determined by infection of 208F cells (NIH 3T3 or bovine mammary epithelial cells can also be employed) followed by selection of G418-resistant colonies as described above in Example 2.

Amplification of retroviral sequences in co-cultures may result in the generation of replication competent retroviruses thus, affecting the safety of the packaging cell line and vector production. Therefore, the cell lines were screened for production of replication competent vector. The 208F cells were expanded to about 30% confluency in a T25 flask (~$10^5$ cells). The cells are then infected with 5 ml of infectious vector at $10^5$ CFU/ml+8 ug/ml polybrene and grown to confluency (~24 h), followed by the addition of media supplemented with G418. The cells were then expand to confluency and the media collected. The media from the infected cells was used to infect new 208F cells. The cells were plated in 6-well at 30% confluency (~$10^5$ cells) using the following dilutions:undiluted, 1:2, 1:4, 1:6, 1:8, 1:10. Cells were expanded to confluency, followed by the addition of G418. The cells were then maintained under selection for 14 days to determine the growth of any neo resistant colonies, which would indicate the presence of replication competent virus.

EXAMPLE 5

Preparation of Pseudotyped Retrovirus for Infection of Host Cells

The concentrated pseudotyped retroviruses were resuspended in 0.1×HBS (2.5 mM HEPES, pH 7.12, 14 mM NaCl, 75 µM Na$_2$HPO$_4$—H$_2$O) and 18 µl aliquots were placed in 0.5 ml vials (Eppendorf) and stored at −80° C. until used. The titer of the concentrated vector was determined by diluting 1 µl of the concentrated virus $10^{-7}$- or $10^{-8}$-fold with 0.1×HBS. The diluted virus solution was then used to infect 208F and bovine mammary epithelial cells and viral titers were determined as described in Example 2. 8 µg/ml polybrene was added to each well. The plates were incubated for 24 hr. Media was removed from wells by aspiration with sterile Pasteur pipet and vacuum. The wells were replenished with appropriate selection medium. The media is replenished as necessary, noted by change (to yellow) in media color. In the beginning this was every two days, as fewer cells remain, the time decreased by virtue of the fact there are fewer cells. At day 10-14 (depending on selection used), the media was removed the cells were fixed with 100% methanol, 2.0 ml/well, minimum 10 minutes, washed, and stained with Giemsa stain, 2.0 ml/well, 15 minutes minimum. The number of stained colonies was counted and the titer was calculated by: average # colonies×dilution factor=# CFU/ml.

EXAMPLE 6

Processing of Retroviral Vectors Containing Genomic DNA Inserts

This example describes the processing of retroviral vectors containing genomic DNA inserts. Neomycin resistant packaging cell clones were selected and propagated. While growing in 96 well plates, 46 clonal cell lines were examined for bovine α-lactalbumin production. Forty-three of the 46 clones were producing detectable levels of bovine α-lactalbumin. The top seven α-lactalbumin producing clones were selected and passaged into 6 well plates. Cell lines were expanded, frozen to be banked and DNA was isolated from each of the seven clonal lines.

The DNA from the cell lines was examined to determine if the α-lactalbumin introns were spliced out correctly and what portion of the α-lactalbumin gene was inserted into the cells.

PCR primers were designed to amplify a portion of the α-lactalbumin gene that spans all three introns. By amplifying this region it is possible to determine if introns were spliced out of the DNA and how many of the introns were spliced out during the insertion of the gene (i.e., packaging cell line production). Two PCR primers (P3 and P4) were designed to amplify this region. A schematic of the gene construct and location of PCR primers is shown in FIG. 3.

```
Primer 3:
5' TGAAGGGCTACGGAGGTGTCAGTTT 3'    (SEQ ID NO.:2)

Primer 4:
5' CACAACTTCTCACAGAGCCACTGAT 3'    (SEQ ID NO.:3)
```

DNA from the top seven α-lactalbumin protein expressing clonal cell lines was screened using the P3/P4 set of PCR primers. As a control sample the bovine α-lactalbumin cDNA was used. This control sample will yield a fragment that is exactly the same as a correctly spliced α-lactalbumin gene fragment. The control sample and 7 clonal cell line PCR reactions were run on a gel. The results indicated that cell lines number 9, 10, 24, 46, and the control α-LA cDNA gave the same size signal. This signal was a band of approximately 350 bp in size. These results suggest that in these four cell lines all three introns were spliced out creating a DNA sequence that is identical to the control α-LA cDNA. Samples 6 and 30 gave PCR fragments of approximately 1650 bp in size, and sample 39 gave a signal of approximately 650 bp in size. The possible sizes of fragments resulting from all the potential splicing combinations are shown below. Different fragment sizes were calculated based on the various sizes that could be produced from the P3/P4 PCR reactions.

1. No introns spliced out:
   Exon 1-Intron 1-Exon 2-Intron 2-Exon 3-Intron 3-Exon 4=1626 bp fragment
2. Intron 3 spliced out:
   Exon 1-Intron 1-Exon 2-Intron 2-Exon 3-Exon 4=1122 bp fragment
3. Intron 2 spliced out:
   Exon 1-Inton 1-Exon 2-Exon 3-Intron 3-Exon 4=1157 bp fragment
4. Intron 1 spliced out:
   Exon 1-Exon 2-Intron 2-Exon 3-Intron 3-Exon 4=1306 bp fragment
5. Introns 2 and 3 spliced out:
   Exon 1-Intron 1-Exon 2-Exon 3-Exon 4=653 bp fragment
6. Introns 1 and 3 spliced out:
   Exon 1-Exon 2-Intron 2-Exon 3-Exon 4=802 bp fragment
7. Introns 1 and 2 spliced out:
   Exon 1-Exon 2-Exon 3-Intron 3-Exon 4=837 bp fragment
8. All introns spliced out:
   Exon 1-Exon 2-Exon 3-Exon 4=333 bp fragment From this information it was concluded that samples numbered 9,10,24,46 contain no introns as they compare exactly to the cDNA control sample and their PCR fragment size appears to be approximately 333 bp. Samples 6 and 30 gave a PCR fragment size of approximately 1650 bp. The only possibility of those described above that fits the data is option 1 in which none of the introns were spliced out. Sample 39 gave a PCR fragment of approximately 650 bp in size. The splicing combination that yields a fragment close to that size of fragment is option 5 (all introns except intron 1 are spliced out). To determine if this is was actually occurred, the PCR fragments were digested with AvrII and Dra I. This was performed to determine which introns may not have been spliced out in these cell lines. An Avr II site is found in the second intron of bovine α-lactalbumin and a Dra I site is found in the third intron of the gene.

An Avr II digest of option 1 samples should give DNA fragments that are approximately 850 and 750 bp in length. A Dra I digest of option 1 samples should give DNA fragments that are approximately 1400 and 250 bp in length. Both Avr II and Dra I digests of option 5 samples result in no cleavage and thus no change in fragment size. Both Avr II and Dra I digests of option 8 samples result also in no cleavage. Results from the digest are presented in the Table 1 below.

TABLE 1

| Sample | Enzyme | Results |
|---|---|---|
| 6 | Avr II | Signal at 750 bp and 850 bp |
| 6 | Dra I | Signal at 1400 bp and 250 bp |

TABLE 1-continued

| Sample | Enzyme | Results |
|---|---|---|
| 9 | Avr II | Signal at 350 bp |
| 9 | Dra I | Signal at 350 bp |
| 10 | Avr II | Signal at 350 bp |
| 10 | Dra I | Signal at 350 bp |
| 24 | Avr II | Signal at 350 bp |
| 24 | Dra I | Signal at 350 bp |
| 30 | Avr II | Signal at 750 bp and 850 bp |
| 30 | Dra I | Signal at 1400 bp and 250 bp |
| 39 | Avr II | Signal at 650 bp |
| 39 | Dra I | Signal at 650 bp |
| 46 | Avr II | Signal at 350 bp |
| 46 | Dra I | Signal at 350 bp |
| CDNA | Avr II | Signal at 350 bp |
| CDNA | Dra I | Signal at 350 bp |

From the Avr II and Dra I digest it was concluded that samples 6 and 30 contain every intron (option 1) based on the data showing the samples cutting with Avr II and Dra I and gave the correct size digestion products. Sample 39 did not digest with either Avr II or Dra I which would indicate that I2 and I3 were spliced out. The size of the E1-I1-E2-E3-E4 fragment would be 653, which matches the fragment size given by sample 39 when run with the P3/P4 primers. Samples 9, 10, 24 and 46 also did not cut with either enzyme, confirming that the samples did have all the introns removed (option 8).

In conclusion, samples 9, 10, 24 and 46 appear to contain no introns. Sample 6 and 30 contain all introns, and sample 39 contains only the first intron along with all of the exons. Since α-LA protein is produced from the cell lines, the splicing differences do not appear to effect protein expression. Thus, the rest of the introns must be spliced out during α-LA mRNA production within the packaging cell lines. It is interesting that in three of the cell lines not all of the introns were spliced out of the α-lactalbumin gene. This data shows that functional retroviral RNA that is capable of being reverse transcribe and inserted into a cells genome can contain introns. The RNA splicing machinery in the initial production of retroviral vector must be somewhat limiting allowing some unspliced or partially spliced RNAs to be packaged into replication defective retroviral particles.

EXAMPLE 7

Vector for Analysis of β-casein

Figure 4:
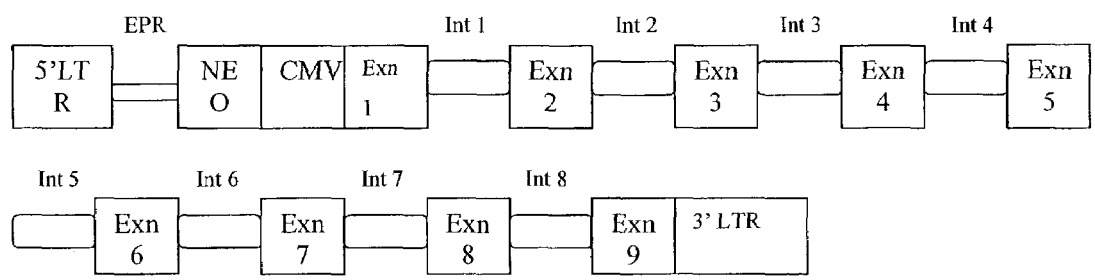
FIG. 4 provides a schematic diagram of a β-casein construct used in some embodiments of the present invention.

This Example describes the construction of a β-casein vector. β-casein is a milk protein that is expressed at high levels in the mammary gland of cattle. The β-casein gene was placed behind the CMV promoter. The construct (SEQ ID NO:4) contains all nine exons and eight introns of the bovine β-casein gene in addition to a couple hundred bases of 3' flanking region. This region of the gene is approximately 8.5 kb in length. The tests performed will be similar to those done with the α-lactalbumin gene construct. A diagram of the construct is provided in FIG. 4. The sequence of the construct is provided in FIG. 5.

EXAMPLE 8

Vector for Analysis of PSMA Antibody

This Example describes the construction of vector for the expression of the PSMA antibody. A gene construct was developed to use a retroviral expression system to remove the introns from the heavy chain gene encoding PSMA antibody and create a cDNA that encodes the heavy chain protein. The PSMA antibody heavy chain gene was placed behind the CMV promoter in the LNC based retroviral backbone. The construct contains all four exons and three introns of the heavy chain gene. A diagram of the final gene construct is shown in FIG. 6.

The sequence (SEQ ID NO:5) of the gene construct is shown in FIG. 6. Replication defective virus was produced using our normal virus production procedure and CHO-S cells were infected with the virus. Neomycin resistant cell clones were selected and propagated. Seven cell lines were selected. All seven cell lines had intron minus DNA, which have has been verified by PCR. The PSMA antibody heavy chain gene was PCR amplified from cell clone 4#. The introns for this PSMA antibody heavy chain genomic gene were spliced out. Sequencing results confirm this to be correct and a cDNA for the PSMA heavy chain gene was created.

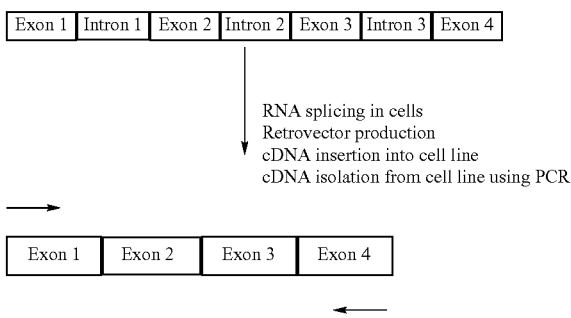

Cloning of PSMA Heavy Chain Antibody cDNA: PCR Amplification

EXAMPLE 9

Vector for Analysis of Pro542 Antibody Fusion

This Example describes the construction of a gene construct for the expression of a Pro542 antibody fusion. A gene construct was created to place the CD4 fused heavy and light chain genes of Pro 542 into a retroviral backbone. The gene construct is shown below. The sequence (SEQ ID NO:6) of the gene construct is shown in FIG. 7. The sequence of the spliced construct (SEQ ID NO:7) is shown in FIG. 8.

This gene construct was used to make vector and packaging cell lines were produced. Due to the presence of introns in the heavy chain gene, the packaging cell lines were screened to determine if the viral insertion step had removed the introns correctly from the above gene construct. PCR primers were designed to amplify through the region of the heavy chain sequence that contains introns. One primer was located at the 3' end of exon 1 (Int Pro 5) and the second primer was located on the 5' end of exon 4 (Int Pro 3). The results of the packaging cell line screening indicated that in most of the cell clones the introns were removed correctly. A 423 bp PCR fragment is generated if the introns are spliced out correctly. Twelve packaging cell lines that contained the correctly spliced fragment were selected and subsequently titered. The top three cell lines were selected based on titer. The 423 bp PCR fragment from each of these three samples was sequenced to further confirm that the intron splicing has occurred correctly. The sequencing results indicated that the heavy chain viral inserts were spliced correctly.

The were found to have undergone additional splicing that removed most of the light chain gene as well as most of the IRES. PCR amplification was done on six different cell lines to identify where splicing occurred in each cell line. Samples 3027 #'s 36, 75, 11, 152, 346, 445 and a pooled population of cells were all amplified with several different primers.

Primers were designed to amplify the whole construct, CMV, the Heavy chain, IRES, the Light chain, and WPRE. The results indicated that CMV, the Heavy chain, and WPRE were present in the cells, and that portions or all of the Light Chain and IRES were missing. The pooled populations did give a band indicating the whole gene is present in the some of the clones in the pooled unselected population.

Since these clones appear to be missing the light chain gene, they were also screened to determine if light chain protein was being produced. The cell lines do not produce light chain protein, but are produce correctly sized heavy chain protein as determine by western blotting. The pooled sample of packaging cell lines produced both heavy and light chain protein as determined by western blotting. The present invention is not limited to a particular mechanism. Indeed, an understanding of the mechanism is not necessary to practice the present invention. Nonetheless, it is contemplated that these data indicate that some of the packaging cell clones are producing both heavy and light chain protein.

Additional clonal packaging cell lines obtained from the pooled population of cells were isolated. Five of these cell lines (11, 20, 24, 0, and 35) were tested using PCR in an attempt to determine if the heavy chain gene, light chain gene and IRES sequence were present in the cell lines. The results are shown in Table 2 below.

TABLE 2

PCR Results

| Sample | Primers | Area of Amplification | Gel Result | Conclusion |
|---|---|---|---|---|
| 11 | IT1/IT2 | Ires | Faint band matching positive control DNA | no Ires |
| 11 | Int Pro 3/Int Pro 5 | Heavy Chain | Band matching positive control DNA containing introns | Contains HC with no introns spliced out |
| 11 | 3546/4475 | 5' Light Chain | No band | No Light Chain |
| 11 | 4325/4912 | 3' Light Chain | No band | No Light Chain |
| 20 | IT1/IT2 | Ires | Faint band matching positive control DNA | no Ires |
| 20 | Int Pro 3/Int Pro 5 | Heavy Chain | Band lower than positive control DNA containing introns, higher than calculated size if all introns spliced out. | Partial splicing of HC |
| 20 | 3546/4475 | 5' Light Chain | No band | No Light Chain |
| 20 | 4325/4912 | 3' Light Chain | No band | No Light Chain |
| 24 | IT1/IT2 | Ires | Faint band matching positive control DNA | no Ires |
| 24 | Int Pro 3/Int Pro 5 | Heavy Chain | Band matching positive control DNA containing introns | Contains HC with no introns spliced out |
| 24 | 3546/4475 | 5' Light Chain | Band matching positive control DNA | Contains 5' end of Light Chain |
| 24 | 4325/4912 | 3' Light Chain | No band | No Light Chain |
| 30 | IT1/IT2 | Ires | Strong band matching positive control DNA | Contains Ires |
| 30 | Int Pro 3/Int Pro 5 | Heavy Chain | Band matching calculated size of HC with introns removed | Contains HC with introns spliced out |
| 30 | 3546/4475 | 5' Light Chain | Band matching positive control DNA | Contains 5' end of Light Chain |
| 30 | 4325/4912 | 3' Light Chain | Band matching positive control DNA | Contains Light chain |
| 35 | IT1/IT2 | Ires | Strong band matching positive control DNA | Contains Ires |
| 35 | Int Pro 3/Int Pro 5 | Heavy Chain | Band matching calculated size of HC with introns removed | Contains HC with introns spliced out |
| 35 | 3546/4475 | 5' Light Chain | Band matching positive control DNA | Contains 5' end of Light Chain |
| 35 | 4325/4912 | 3' Light Chain | Band matching positive control DNA | Contains Light chain |

The results indicate that Cell Lines 30 and 35 contain spliced Heavy chain gene, correctly sized light chain gene, and the IRES sequence. In these two clones the splicing that occurred was what was desired. These two cell lines were able to be used to produce functional vector for generation of Pro 542 production cell lines. These results indicate that multiple types of splicing occurred in this original gene construct when it was put through the retroviral cell line production procedure. In these two clones the splicing that occurred was the desired splicing. This example demonstrates that the retroviral vectors of the present invention are capable of generating properly spliced antibody heavy and light chains in a single construct.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, virology, biochemistry, or related fields are intended to be within the scope of the following claims.

---

What is claimed is:

1. A method for analyzing genomic DNA clones comprising:
   a) providing at least one vector and at least one packaging cell, wherein said at least one vector comprises retroviral 5' and 3' long terminal repeats flanking a genomic DNA sequence, wherein said genomic DNA sequence is from 20 kilobases to 200 kilobases in length and includes introns;
   b) introducing said at least one vector into said at least one packaging cell under conditions such that a RNA molecule corresponding to said retroviral 5' and 3' long terminal repeats and said genomic DNA with said introns removed sequence is transcribed and said RNA molecule is packaged into said retroviral particle, wherein said introns are removed from said RNA prior to said packaging, and wherein after removal of said introns, said RNA is 11 kilobases or less in size;
   c) transducing a cell line having a genome with said retroviral particle under conditions such that said RNA molecule corresponding to said retroviral 5' and 3' long terminal repeats flanking a genomic DNA sequence with said introns removed is reverse transcribed and inserted into the genome of said cell line as a provirus; and
   d) analyzing said genomic clone in said provirus.

2. The method of claim 1, wherein said at least one packaging cell is a 293GP cell.

3. The method of claim 1, wherein said retroviral particle is a pseudotyped retroviral particle.

4. The method of claim 1, wherein said cell line is selected from the group consisting of 293 cells, CHO cells, 3T3 cells, and 208F cells.

5. The method of claim 1, wherein said at least one vector is selected from the group consisting of plasmid, cosmid, yeast artificial chromosome, and bacterial artificial chromosome vectors.

6. The method of claim 1, wherein said genomic DNA sequence is from 50 kilobases to 100 kilobases in length.

7. The method of claim 1, wherein said analyzing of said provirus further comprises sequencing said provirus to provide a sequenced provirus.

8. The method of claim 7, wherein said sequenced provirus is compared to said genomic DNA sequence to determine exon and intron boundaries.

9. The method of claim 7, wherein multiple proviruses are sequenced and compared to identify splice variants.

10. The method of claim 1, wherein said analyzing of said genomic clone comprises amplification of said genomic clone with PCR primers.

* * * * *

SEQUENCE LISTING

<160> NUMBER OF SEQ ID NOS: 7

<210> SEQ ID NO 1
<211> LENGTH: 9009
<212> TYPE: DNA
<213> ORGANISM: Artificial Sequence
<220> FEATURE:
<223> OTHER INFORMATION: Synthetic

<400> SEQUENCE: 1

```
gaattaattc ataccagatc accgaaaact gtcctccaaa tgtgtccccc tcacactccc        60
aaattcgcgg gcttctgcct cttagaccac tctaccctat tccccacact caccggagcc       120
aaagccgcgg cccttccgtt tctttgcttt tgaaagaccc cacccgtagg tggcaagcta       180
gcttaagtaa cgccactttg caaggcatgg aaaaatacat aactgagaat agaaaagttc       240
agatcaaggt caggaacaaa gaaacagctg aataccaaac aggatatctg tggtaagcgg       300
ttcctgcccc ggctcagggc caagaacaga tgagacagct gagtgatggg ccaaacagga       360
tatctgtggt aagcagttcc tgccccggct cggggccaag aacagatggt ccccagatgc       420
ggtccagccc tcagcagttt ctagtgaatc atcagatgtt tccagggtgc cccaaggacc       480
tgaaaatgac cctgtacctt atttgaacta accaatcagt tcgcttctcg cttctgttcg       540
cgcgcttccg ctctccgagc tcaataaaag agcccacaac ccctcactcg gcgcgccagt       600
cttccgatag actgcgtcgc ccgggtaccc gtattcccaa taaagcctct tgctgtttgc       660
atccgaatcg tggtctcgct gttccttggg agggtctcct ctgagtgatt gactacccac       720 gacggggggtc tttcatttgg gggctcgtcc gggatttgga gacccctgcc cagggaccac       780
cgacccacca ccgggaggta agctggccag caacttatct gtgtctgtcc gattgtctag       840
tgtctatgtt tgatgttatg cgcctgcgtc tgtactagtt agctaactag ctctgtatct       900
ggcggacccg tggtggaact gacgagttct gaacacccgg ccgcaaccct gggagacgtc       960
ccagggactt tgggggccgt ttttgtggcc cgacctgagg aagggagtcg atgtggaatc      1020
cgaccccgtc aggatatgtg gttctggtag gagacgagaa cctaaaacag ttcccgcctc      1080
cgtctgaatt tttgctttcg gtttggaacc gaagccgcgc gtcttgtctg ctgcagcgct      1140
gcagcatcgt tctgtgttgt ctctgtctga ctgtgtttct gtatttgtct gaaaattagg      1200
gccagactgt taccactccc ttaagtttga ccttaggtca ctggaaagat gtcgagcgga      1260
tcgctcacaa ccagtcggta gatgtcaaga agagacgttg ggttaccttc tgctctgcag      1320
aatggccaac ctttaacgtc ggatggccgc gagacggcac ctttaaccga gacctcatca      1380
cccaggttaa gatcaaggtc ttttcacctg gcccgcatgg acacccagac caggtcccct      1440
acatcgtgac ctgggaagcc ttggcttttg accccctcc ctgggtcaag ccctttgtac      1500
accctaagcc tccgcctcct cttcctccat ccgcccgtc tctccccctt gaacctcctc      1560
gttcgacccc gcctcgatcc tccctttatc cagccctcac tccttctcta ggcgccgaa      1620 ttccgatctg atcaagagac aggatgagga tcgtttcgca tgattgaaca agatggattg      1680
```

```
cacgcaggtt ctccggccgc ttgggtggag aggctattcg gctatgactg ggcacaacag   1740
acaatcggct gctctgatgc cgccgtgttc cggctgtcag cgcaggggcg cccggttctt   1800
tttgtcaaga ccgacctgtc cggtgccctg aatgaactgc aggacgaggc agcgcggcta   1860
tcgtggctgg ccacgacggg cgttccttgc gcagctgtgc tcgacgttgt cactgaagcg   1920
ggaagggact ggctgctatt gggcgaagtg ccggggcagg atctcctgtc atctcacctt   1980
gctcctgccg agaaagtatc catcatggct gatgcaatgc ggcggctgca tacgcttgat   2040
ccggctacct gcccattcga ccaccaagcg aaacatcgca tcgagcgagc acgtactcgg   2100
atggaagccg gtcttgtcga tcaggatgat ctggacgaag agcatcaggg gctcgcgcca   2160
gccgaactgt tcgccaggct caaggcgcgc atgcccgacg gcgaggatct cgtcgtgacc   2220
catggcgatg cctgcttgcc gaatatcatg gtggaaaatg gccgcttttc tggattcatc   2280
gactgtggcc ggctgggtgt ggcggaccgc tatcaggaca tagcgttggc tacccgtgat   2340
attgctgaag agcttggcgg cgaatgggct gaccgcttcc tcgtgcttta cggtatcgcc   2400
gctcccgatt cgcagcgcat cgccttctat cgccttcttg acgagttctt ctgagcggga   2460 ctctgggggtt cgaaatgacc gaccaagcga cgcccaacct gccatcacga gatttcgatt   2520
ccaccgccgc cttctatgaa aggttgggct tcggaatcgt tttccgggac gccggctgga   2580
tgatcctcca gcgcggggat ctcatgctgg agttcttcgc ccaccccggg ctcgatcccc   2640
tcgcgagttg gttcagctgc tgcctgaggc tggacgacct cgcggagttc taccggcagt   2700
gcaaatccgt cggcatccag gaaaccagca gcggctatcc gcgcatccat gcccccgaac   2760
tgcaggagtg gggaggcacg atggccgctt tggtcgaggc ggatccggcc attagccata   2820
ttattcattg gttatatagc ataaatcaat attggctatt ggccattgca tacgttgtat   2880
ccatatcata atatgtacat ttatattggc tcatgtccaa cattaccgcc atgttgacat   2940
tgattattga ctagttatta atagtaatca attacgggt cattagttca tagcccatat   3000
atggagttcc gcgttacata acttacggta aatggcccgc ctggctgacc gcccaacgac   3060
ccccgcccat tgacgtcaat aatgacgtat gttcccatag taacgccaat agggactttc   3120
cattgacgtc aatgggtgga gtatttacgg taaactgccc acttggcagt acatcaagtg   3180
tatcatatgc caagtacgcc ccctattgac gtcaatgacg gtaaatggcc cgcctggcat   3240
tatgcccagt acatgacctt atgggacttt cctacttggc agtacatcta cgtattagtc   3300
atcgctatta ccatggtgat gcggttttgg cagtacatca atgggcgtgg atagcggttt   3360
gactcacggg gatttccaag tctccacccc attgacgtca atgggagttt gttttggcac   3420
caaaatcaac gggactttcc aaaatgtcgt aacaactccg ccccattgac gcaaatgggc   3480
ggtaggcatg tacggtggga ggtctatata agcagagctc gtttagtgaa ccgtcagatc   3540
gcctggagac gccatccacg ctgttttgac ctccatagaa gacaccggga ccgatccagc   3600
ctccgcggcc ccaagcttct cgagttaaca gatctcgacc tgcaccccct aaccaaaatg   3660
atgtcctttg tctctctgct cctggtaggc atcctattcc atgccaccca ggctgaacag   3720
ttaacaaaat gtgaggtgtt ccgggagctg aaagacttga agggctacgg aggtgtcagt   3780
ttgcctgaat gtgagttccc tgctatttg ctttgtccca taattcatcc tcttcactct   3840
ttccctccat tctcttcatc ctcttttccc cctctacttt taattatcaa acaattctct   3900
tatttgttta ctcttttatt acatttattt atctgcctct cctttttccc attgtctgat   3960
cctttggaac tctttttcacc ttaacaagat actctgtggt ctgccatatt tggagattgg   4020
ttggagagcc ttttttcggtc tgggaataca ggtcctcatt tatgctatac atgaacatcc   4080
```

```
ttgtgaaatc tcttttcgt ctttctttca ggggtctgta ccgcgtttca taccagtggt    4140
tatgacacac aagccatagt acaaaacaat gacagcacag aatatggact cttccagata    4200
aataataaaa tttggtgcaa agacgaccag aaccctcact caagcaacat ctgtaacatc    4260
tcctgtgaca gtgagtaact tctttttact ctgttcctgt gtttttctga aacctactcc    4320
tgggataacc tccttttttt tggtgtgaag cacacctctg gcttcactgc cttggactcc    4380
aaattaactg tgggacttga taataccgag taagaggctc ttagaatttt tcattaacac    4440
taaatcccca gacagtttct taaagttcct gggtaggtga cctgagctgt ttggggatct    4500
tgatgtataa taccctgtat tttcagacta agttggttga tgaagttgat aattcctaag    4560
gagctgcccc agagaagaga agggagtcct tacctaggga taggcattac tgtattaaat    4620
ttctcaccca gaaggcaaca ggcataagcc tctagttcag agaaaccag agaagaggga    4680
aattcattat ccttctgggt aatacttagc tctctcattt tttccaccag aggctcctgc    4740
cagagttcct ggatgatgat cttactgatg acattatgtg tgtcaagaag attctggata    4800
aagtaggaat taactactgg tgagtcacct ctctattttt cacttaatct ttcctctctt    4860
tcttctcagt cctttcgtcc cagcactata ctcctttctc tctatttctt ggtcttttaa    4920
gctagaatgt aatcttaaaa acaaaaatca tcaagcagac tccggtttcc aattttgaag    4980
cttcacttac ttcactcccg ttagcaattt tcctacctaa gggtccctaa tagagggctg    5040
agatccagga tttccttcac caggacttga acatctaatt ctacttgttc agtcctacat    5100
cctaaggcac gcccttgac cactgccccg cattttctt ggagttttaa aaaatggacc    5160
ttactccact aagtggctca gtgtctctag ccatgtggct aggaaagtct gtctgtaatt    5220
ttaacccaca gtcttccacc tcagccttcc tggggataaa gctagatgta aatctaacca    5280
agatcctgtc agtaatttgc cttgtctcct tcttcatgat caggttggcc cataaagcac    5340
tctgttctga gaagctggat cagtggctct gtgagaagtt gtgaacacct gctgtctttg    5400
ctgcttctgt cctctttctg ttcctggaac tcctctgccc cgtggctacc tcgttttgct    5460
tctttgtacc cccttgaagc taactcgtct ctgagccctg ggccctgtag tgacaatgga    5520
catgtaagga ctaatctcca ggtgtgcatg aatggcgctc tggactttg acccttgctc    5580
gatgtccctg atggcgcttt taatgcaaca gtacatattc cactttgtc ccgaataaaa    5640
agcctgattt tgagtggctg ctgtattttt cttcctggtg ggagagggag gaaataggt    5700
gagtaggtag acctggccat gggtcacaga ccccttcatc tctactaaag aggatagaga    5760
ggctgaactt ataacaactc aaagatggag attactttct gtattaattc aattcaacag    5820
agttttattg atcacctagc ataatttaaa gagctatgga ggggatctaa agttgactaa    5880
aagcatctct tacctaaact gctgctaagt cacttcagtt gtgtccgact ctgtgtgacc    5940
ccatagacgg tagcccacaa ggctcccatg tccctggaat tcgatatcaa gcttatcgat    6000
accgtcgaca tcgataaaat aaaagatttt atttagtctc cagaaaaagg ggggaatgaa    6060
agaccccacc tgtaggtttg gcaagctagc ttaagtaacg ccattttgca aggcatggaa    6120
aaatacataa ctgagaatag agaagttcag atcaaggtca ggaacagatg gaacagctga    6180
atatgggcca acaggatat ctgtggtaag cagttcctgc cccggctcag ggccaagaac    6240
agatggaaca gctgaatatg ggccaaacag gatatctgtg gtaagcagtt cctgccccgg    6300
ctcagggcca agaacagatg gtccccagat gcggtccagc cctcagcagt ttctagagaa    6360
ccatcagatg tttccagggt gccccaagga cctgaaatga ccctgtgcct tatttgaact    6420
```

```
aaccaatcag ttcgcttctc gcttctgttc gcgcgcttct gctccccgag ctcaataaaa   6480
gagcccacaa cccctcactc ggggcgccag tcctccgatt gactgagtcg cccgggtacc   6540
cgtgtatcca ataaaccctc ttgcagttgc atccgacttg tggtctcgct gttccttggg   6600
agggtctcct ctgagtgatt gactacccgt cagcggggt ctttcatttg ggggctcgtc    6660
cgggatcggg agaccctgc ccagggacca ccgacccacc accggggagg aagctggctg    6720
cctcgcgcgt ttcggtgatg acggtgaaaa cctctgacac atgcagctcc cggagacggt   6780
cacagcttgt ctgtaagcgg atgccgggag cagacaagcc cgtcagggcg cgtcagcggg   6840
tgttggcggg tgtcggggcg cagccatgac ccagtcacgt agcgatagcg gagtgtatac   6900
tggcttaact atgcggcatc agagcagatt gtactgagag tgcaccatat gcggtgtgaa   6960
ataccgcaca gatgcgtaag gagaaaatac cgcatcaggc gctcttccgc ttcctcgctc   7020
actgactcgc tgcgctcggt cgttcggctg cggcgagcgg tatcagctca ctcaaaggcg   7080
gtaatacggt tatccacaga atcagggat aacgcaggaa agaacatgtg agcaaaaggc     7140
cagcaaaagg ccaggaaccg taaaaaggcc gcgttgctgg cgttttttcca taggctccgc   7200 cccctgacg agcatcacaa aaatcgacgc tcaagtcaga ggtggcgaaa cccgacagga    7260
ctataaagat accaggcgtt tccccctgga agctccctcg tgcgctctcc tgttccgacc   7320
ctgccgctta ccggatacct gtccgccttt ctcccttcgg gaagcgtggc gctttctcat   7380
agctcacgct gtaggtatct cagttcggtg taggtcgttc gctccaagct gggctgtgtg   7440 cacgaaccc cgttcagcc cgaccgctgc gccttatccg gtaactatcg tcttgagtcc      7500
aacccggtaa gacacgactt atcgccactg gcagcagcca ctggtaacag gattagcaga   7560
gcgaggtatg taggcggtgc tacagagttc ttgaagtggt ggcctaacta cggctacact   7620
agaaggacag tatttggtat ctgcgctctg ctgaagccag ttaccttcgg aaaaagagtt   7680
ggtagctctt gatccggcaa acaaaccacc gctggtagcg gtggtttttt tgtttgcaag   7740
cagcagatta cgcgcagaaa aaaggatct caagaagatc ctttgatctt ttctacgggg    7800
tctgacgctc agtggaacga aaactcacgt taagggattt tggtcatgag attatcaaaa   7860
aggatcttca cctagatcct tttaaattaa aaatgaagtt ttaaatcaat ctaaagtata   7920
tatgagtaaa cttggtctga cagttaccaa tgcttaatca gtgaggcacc tatctcagcg   7980
atctgtctat ttcgttcatc catagttgcc tgactccccg tcgtgtagat aactacgata   8040
cgggagggct taccatctgg ccccagtgct gcaatgatac cgcgagaccc acgctcaccg   8100
gctccagatt tatcagcaat aaaccagcca gccggaaggg ccgagcgcag aagtggtcct   8160
gcaactttat ccgcctccat ccagtctatt aattgttgcc gggaagctag agtaagtagt   8220
tcgccagtta atagtttgcg caacgttgtt gccattgctg caggcatcgt ggtgtcacgc   8280
tcgtcgtttg gtatggcttc attcagctcc ggttcccaac gatcaaggcg agttacatga   8340
tcccccatgt tgtgcaaaaa agcggttagc tccttcggtc ctccgatcgt tgtcagaagt   8400
aagttggccg cagtgttatc actcatggtt atggcagcac tgcataattc tcttactgtc   8460
atgccatccg taagatgctt ttctgtgact ggtgagtact caaccaagtc attctgagaa   8520
tagtgtatgc ggcgaccgag ttgctcttgc ccggcgtcaa cacgggataa taccgcgcca   8580
catagcagaa ctttaaaagt gctcatcatt ggaaaacgtt cttcggggcg aaaactctca   8640
aggatcttac cgctgttgag atccagttcg atgtaaccca ctcgtgcacc caactgatct   8700
tcagcatctt ttactttcac cagcgtttct gggtgagcaa aaacaggaag gcaaaatgcc   8760
gcaaaaaagg gaataagggc gacacggaaa tgttgaatac tcatactctt cctttttcaa   8820
```

-continued

```
tattattgaa gcatttatca gggttattgt ctcatgagcg gatacatatt tgaatgtatt    8880
tagaaaaata aacaaatagg ggttccgcgc acatttcccc gaaaagtgcc acctgacgtc    8940
taagaaacca ttattatcat gacattaacc tataaaaata ggcgtatcac gaggcccttt    9000
cgtcttcaa                                                            9009

<210> SEQ ID NO 2
<211> LENGTH: 25
<212> TYPE: DNA
<213> ORGANISM: Artificial Sequence
<220> FEATURE:
<223> OTHER INFORMATION: Synthetic

<400> SEQUENCE: 2
tgaagggcta cggaggtgtc agttt                                            25

<210> SEQ ID NO 3
<211> LENGTH: 25
<212> TYPE: DNA
<213> ORGANISM: Artificial Sequence
<220> FEATURE:
<223> OTHER INFORMATION: Synthetic

<400> SEQUENCE: 3
cacaacttct cacagagcca ctgat                                            25

<210> SEQ ID NO 4
<211> LENGTH: 12770
<212> TYPE: DNA
<213> ORGANISM: Artificial Sequence
<220> FEATURE:
<223> OTHER INFORMATION: Synthetic

<400> SEQUENCE: 4
tttgaaagac cccacccgta ggtggcaagc tagcttaagt aacgccactt tgcaaggcat      60
ggaaaaatac ataactgaga atagaaaagt tcagatcaag gtcaggaaca agaaacagc     120 tgaataccaa acaggatatc tgtggtaagc ggttcctgcc ccggctcagg gccaagaaca    180
gatgagacag ctgagtgatg ggccaaacag gatatctgtg gtaagcagtt cctgccccgg    240
ctcggggcca agaacagatg gtccccagat gcggtccagc cctcagcagt ttctagtgaa    300
tcatcagatg tttccagggt gccccaagga cctgaaaatg accctgtacc ttatttgaac    360
taaccaatca gttcgcttct cgcttctgtt cgcgcgcttc cgctctccga gctcaataaa    420
agagcccaca cccctcact cggcgcgcca gtcttccgat agactgcgtc gcccgggtac     480
ccgtattccc aataaagcct cttgctgttt gcatccgaat cgtggtctcg ctgttccttg    540
ggagggtctc ctctgagtga ttgactaccc acgacggggg tctttcattt ggggggctcgt   600 ccgggatttg gagacccctg cccagggacc accgacccac caccgggagg taagctggcc    660
agcaacttat ctgtgtctgt ccgattgtct agtgtctatg tttgatgtta tgcgcctgcg    720
tctgtactag ttagctaact agctctgtat ctggcggacc cgtggtggaa ctgacgagtt    780
ctgaacaccc ggccgcaacc ctgggagacg tcccagggac tttggggggcc gttttttgtgg  840 cccgacctga ggaagggagt cgatgtgaa tccgaccccg tcaggatatg tggttctggt     900
aggagacgag aacctaaaac agttcccgcc tccgtctgaa ttttgcttt cggtttggaa     960 ccgaagccgc gcgtcttgtc tgctgcagcg ctgcagcatc gttctgtgtt gtctctgtct   1020
gactgtgttt ctgtattgt ctgaaaatta gggccagact gttaccactc ccttaagttt    1080
```

```
gaccttaggt cactggaaag atgtcgagcg gatcgctcac aaccagtcgg tagatgtcaa    1140
gaagagacgt tgggttacct tctgctctgc agaatggcca acctttaacg tcggatggcc    1200
gcgagacggc acctttaacc gagacctcat cacccaggtt aagatcaagg tcttttcacc    1260
tggcccgcat ggacacccag accaggtccc ctacatcgtg acctgggaag ccttggcttt    1320
tgacccccct ccctgggtca agcccttttgt acaccctaag cctccgcctc ctcttcctcc    1380
atccgccccg tctctccccc ttgaacctcc tcgttcgacc ccgcctcgat cctccctttta    1440 tccagccctc actccttctc taggcgccgg aattccgatc tgatcaagag acaggatgag    1500
gatcgtttcg catgattgaa caagatggat tgcacgcagg ttctccggcc gcttgggtgg    1560
agaggctatt cggctatgac tgggcacaac agacaatcgg ctgctctgat gccgccgtgt    1620
tccggctgtc agcgcagggg cgcccggttc tttttgtcaa gaccgacctg tccggtgccc    1680
tgaatgaact gcaggacgag gcagcgcggc tatcgtggct ggccacgacg gcgttccttt    1740
gcgcagctgt gctcgacgtt gtcactgaag cggaaggga ctggctgcta ttgggcgaag    1800
tgccggggca ggatctcctg tcatctcacc ttgctcctgc cgagaaagta tccatcatgg    1860
ctgatgcaat gcggcggctg catacgcttg atccggctac ctgcccattc gaccaccaag    1920
cgaaacatcg catcgagcga gcacgtactc ggatggaagc cggtcttgtc gatcaggatg    1980
atctggacga agagcatcag gggctcgcgc cagccgaact gttcgccagg ctcaaggcgc    2040
gcatgcccga cggcgaggat ctcgtcgtga cccatggcga tgcctgcttg ccgaatatca    2100
tggtggaaaa tggccgcttt tctggattca tcgactgtgg ccggctgggt gtggcggacc    2160
gctatcagga catagcgttg gctacccgtg atattgctga agagcttggc ggcgaatggg    2220
ctgaccgctt cctcgtgctt tacggtatcg ccgctcccga ttcgcagcgc atcgccttct    2280
atcgccttct tgacgagttc ttctgagcgg gactctgggg ttcgaaatga ccgaccaagc    2340
gacgcccaac ctgccatcac gagatttcga ttccaccgcc gccttctatg aaaggttggg    2400
cttcggaatc gttttccggg acgccggctg gatgatcctc cagcgcgggg atctcatgct    2460
ggagttcttc gcccaccccg ggctcgatcc cctcgcgagt tggttcagct gctgcctgag    2520
gctggacgac ctcgcggagt tctaccggca gtgcaaatcc gtcggcatcc aggaaaccag    2580
cagcggctat ccgcgcatcc atgccccga actgcaggag tggggaggca cgatggccgc    2640
tttggtcgag gcggatccgg ccattagcca tattattcat tggttatata gcataaatca    2700
atattggcta ttggccattg catacgttgt atccatatca taatatgtac atttatattg    2760
gctcatgtcc aacattaccg ccatgttgac attgattatt gactagttat taatagtaat    2820
caattacggg gtcattagtt catagcccat atatggagtt ccgcgttaca aacttacgg    2880 taaatggccc gcctggctga ccgcccaacg acccccgccc attgacgtca ataatgacgt    2940
atgttcccat agtaacgcca atagggactt tccattgacg tcaatgggtg gagtatttac    3000
ggtaaactgc ccacttggca gtacatcaag tgtatcatat gccaagtacg ccccctattg    3060
acgtcaatga cggtaaatgg cccgcctggc attatgccca gtacatgacc ttatgggact    3120
ttcctacttg gcagtacatc tacgtattag tcatcgctat taccatggtg atgcggtttt    3180
ggcagtacat caatgggcgt ggatagcggt ttgactcacg gggatttcca agtctccacc    3240
ccattgacgt caatgggagt ttgttttggc accaaaatca acgggacttt ccaaaatgtc    3300
gtaacaactc cgccccattg acgcaaatgg gcggtaggca tgtacggtgg gaggtctata    3360
taagcagagc tcgtttagtg aaccgtcaga tcgcctggag acgccatcca cgctgttttg    3420
acctccatag aagacaccgg gaccgatcca gcctccgcgg ccccaagctt ctcgagttaa    3480
```

```
cagatcccg atcacattca gctcctcctt cacttcttgt cctctacttt ggaaaaaagg    3540
taagaatctc agatataatt tcattgtatc tgctactcat ctttatttca gactaggtta    3600
aaatgtagaa agaacataat tgcttaaaat agatcttaaa aataaggatg tttaagataa    3660
agtttacagt attttcagca aatttgttaa aaaatagaag caactataaa gatttgtaac    3720
agtggttgct attttctta ccacgagact agttaacagg ctgtattaaa agatctttc    3780 ttgaattaaa tattttcaat ttgattaaac atacctcagc cataaaggca agcacattta    3840
atttatacta tgggaatttg ataattgtt actgaagaag ctctaccaac aaaaagttta    3900
tagagctagc atatttagtc aagagataaa gagggttgtt aggatacatg tgctatttga    3960
aaggtattta taaagaaga gtatatttat taaaattgct cagaacatcc aaatttcaag    4020
tttatcattt atcttacaat atttcaaaaa tattaaaata gatacatgaa atacagaagt    4080
aaattaaaga gaaagtattt tattttgtaa aaaaaaattc taggttggac agggagtacc    4140
aggaaacaaa aacaatgaa aaatgtgatc tgacagaaat tatagctcaa agtatagtag    4200
tcagtaatga aatggcttaa aaattggcat ataaaatgct aattataaaa taaacaaaat    4260
gtaataatac cctccctaca tgtaatgaac tctgagtatt atactctttt ttgaagtctt    4320
gacaatgaaa atttatttag acttttatag acatcttgga taaagtaaaa caaattacga    4380
attagcatcc atgagaaaaa tatagaaaaa tttcttaatg tagtttgcaa atctgggat    4440 tgaagatgtg tgtcaagaga ttgtgatggc agacattttt tttcagacta taaaatgcac    4500
aaacaaccat ttaatacatt ttggtcaaaa atagtatgta ttttatttta tgctacagga    4560
gagtagtcta aagtaggact gggcagagat ctgacaccct ggtaatcacc gagagatagt    4620
acacagtctc tgtagagaaa ataagcatag tgtatgatct ctaaattat gtggacaaag    4680 gggagataac attaggcatg tggggatgaa gactgagtac agaagaacaa tctagtcagt    4740
ccaagaaaac atgtggatca atggaacaaa tagaagaaat gctaaaatga aacagaagtc    4800
ttactggaaa taaagatat gaggaagaca acattcatg aaaatcactt agtttagtag    4860
agaaaagata aaaataaagt attaccttct tcttcatata cattgtttga tcagatgccc    4920
ctcaataaaa ctgagtctcc aacagaactg aaactttaat attttgttca ctgctctaat    4980
cccagaatct aagacatatc tggcaataaa aattaataaa taaatatttt taataagtaa    5040
atcaatcact taattttct gtaagtatct gtaacttctc ttctgtctt ccaaaaaaca    5100 ctcataagta ctgtgaataa gatgaaaaga gtgaaataag atataggctg ttagctgaaa    5160
acatctggat ggctggcagt gaaacattaa cttgaaatgt aagattaatg agtaatagta    5220
aattttaacc ttggccgtat gataaaatgt ctattaatat ttttctaaaa tacagggctt    5280 tttgttttg ccatgaggtt tgcaggatct tggttccctg atgagggatc aaacctgggc    5340
tcccctggaa gcacggagtc ttagatattt gtattataca ctatctttgg tttcttttaa    5400
agggaagtaa ttctacttaa ataagaaaat agattgacaa gtaatacact atttcctcat    5460
cttcccattc ccaggaattg agagccatga aggtcctcat ccttgcctgc ctggtggctc    5520
tggcccttgc aagagaggta aatacagaaa aaatgttgaa ataaataaga ctagtactat    5580
ctgctatgtg tagaaaattc attaccaaca ttgtaaatgt ataaataatg cacaatctca    5640
gatttttttt gaatgctaag aaagtcattt acgttcatcc actatctcag tagtatccta    5700
tgggaccaca agtctgagtc tagtgctttc tatagtattg taccatctgt accatcaatc    5760
cctaaagaaa aagaaaata aaccaataag caacagacta acaagaagga acacagataa    5820
```

-continued

```
gaacaaaaag tgagtaatat tgcataaata caattgcatg catatacaat ctagataaat    5880
atatcttatt ccagtgatga aatatttgta tcccttactg tagagtgcta ggtttagctg    5940
tgtctattca acacaggatg atactccaga ggatggtata tcagacaaca ataataaata    6000
tgttcataat tataataaaa agtgttcagt aaaaattaaa ataactcctt ttctgttacc    6060
cataaaaact cttcattaaa gtaaaacaaa aatatactaa tgaaagttac taaatttaaa    6120
agactctcaa aagacatata acatttttat ttttcagatt tgtgaaatag atagctctga    6180
ataaagcaag taaaaattag gtaggaaaat atttaataat gagttgactg tgggaactaa    6240
agtgtttttt tttctcttta gctggaagaa ctcaatgtac ctggtgaggt aagatatttt    6300
tatacaaaga aaaaaattaa tttaactgta aaatagtaac agtctctaat gatctggcag    6360
aagactcagc taattgtcaa tttttatttt tcctttatag attgtggaaa gcctttcaag    6420
cagtgaggta agatagtgtt cattcagagg caatttccca aatttagagc aataaaatgc    6480
tgtattatct ttttgtgtta cattaatggc aacccactcc agtattcttg cctggaaaat    6540
cccatagagg aggagcctgg taggctgcag tccacggggt cgctaagagt cggacaggac    6600
tgagcgactt cccttttcact tttcactttc atgccttgga gaggaaatg gcaacccact    6660
ccagttttct tgccgggaga atcccaggga cgggggagcc tggtgggctg ccgtctatgg    6720
gggtcgcaca gagttggaca cgactgaagc gacttagcag tagcagcagc aggacagtta    6780
aggtttctct aatagctcag ttggtaaaga atctgcctgc agtgcaggag gaccctgggt    6840
tcgattcctc aagatctgca ggagaaggga taggctaccc attccagtgt tctttaagcc    6900
aatgtggcta tgtactgacg ggtaactatt gtcaatttcc actctgtata tttaaaggaa    6960
taaatgtgta gaaggtttaa tattctagta atttctaaat gggtttgtta tttgaaattg    7020
tgtcattgtg ccctgctttt tttccttaat gaactgtaca gtcctctttt ctgtcttgaa    7080
ctttctatgt taacctcctt ccatgctttg gcatttattg agcactttct gtttcagact    7140
ttgactagga actgcagtac aaactagaaa gagggatgcc ctttgtaaag tgtgagcaga    7200
catgcaaatg gacatatttt attattatac aagcaatcca gtacacaaga ggcagtgaga    7260
atgagtgtag tcctaaatct gcctggtgga atgaggtaga taataaccct atgccactct    7320
ttttggctct gtcatcagct gttggttaaa tagtgcatca atatactttg tctcttcaca    7380
aaggtcaaaa gatgctgctg ctgctgctaa gtcgcttcag tcatgtccga ctctgtgcga    7440
cctcatagat ggcagcctgc caggctcccc catccctggg attctccagg caagaatact    7500
ggagtgggtt gccatttcct attccaatgc ataaaagtga aaagtgaaag tgaagtcgct    7560
cagtcgtgtc cgactcctag tgaccccgtg gactgcagcc taccaggctc ctccatccat    7620
gggattttcc aggcaagagt actggagtgg gttgccattg ccatctccaa agatccttat    7680
aggagggtat gtatttctta taattcatta gaagcctaaa cataaccagg gaactaagaa    7740
tgattaacaa gttcatgcgt ggttattatt atatattttc aatgactatt attctttttag   7800
aaccagatga aaatattaga gatcatttgt tgtcctaagg agagaacagg atgattgaga    7860
gacatgtatg catgcaaagt tacttcagcc ctttccaact ctgtatgacc ctatggactg    7920
taacctgcca ggttcctctg tctatgggat tctccaggca agaatacagg agtgggttgt    7980
catctcctcc agggcctagg aattgacctg catctcttac gtctcctgca ttggcaggca    8040
ggttctttac cactagcacc acctggaagc ccgattagta tctgttaaat gcctcttttga    8100
gtactatgct ctctaatcct ctttttcttg attgcatcat ctttctttttt atacaacagc    8160
cttattcaga agagtggaac ataaactttc agccataaaa taatgatatt atcaaatgag    8220
```

```
ctgtccatat taatctatta aatttcttca ttttctgatt tatgttgaca aataagaatt     8280
ttttttaaag ctagacctga ttttatttt attttccaa aggaatctat tacacgcatc      8340
aataaggtaa aaccctcat atttaaatgt acatttttt aaatttcatg tttgatttt       8400 ataaacagca tttctttatg tattttttt ttaaccagaa aattgagaag tttcagagtg     8460
aggaacagca gcaaacagag gtaatttgtt cactatgagt atattttgag aagtattatg    8520
aaacataaca cataaaaaga tttataataa ttatgttcag tctaagaatg gtaatataaa    8580
tgtcagtgca agaaataaaa actttgacaa aatgaaaata ttttaaaaat ataaacgcat    8640
tttaaaacac ataatcaaat ttcacagtat agaataaata gctaagaata attattgatg    8700 tattcattt  actaatggta tacctggttt taataactgc atattagtag gaacatttcc    8760
agactaggga ctgtgatccc cttattctaa tgatggatat gctgatgaaa gacagtaggg    8820
tgacagtgtg gcactaatcc tcatctgatc atttatcagc tgtataacct tggctccatg    8880
tttctctgta catcattttc ttcacctgta aattgagaat attcataatt acccagagtt    8940
gatgaactga cacacaatga atattcagtg gttttatatt atatttgata gcttttatac    9000
tcacatttat ggatgtgtgg agttctaaaa agtatttcca ttgcccagat gagagaagtg    9060
aggtacagga caattgagta tgcaaatgtg tgaccatacc acatagttat taaatagcag    9120
aacttgctta aaaacaagga tttgcggaca atgtaaaatt ctttcattat attactcttg    9180
tggtaacata tttatctaat tatgatattt aagctttcct cttttataat tgaagtttga    9240
ttgtttggca cttaggccaa attctaaatc aaaatgaatt tacaacttga tgcctttgaa    9300
gactcaagat taccaccttc taccaagaga agtagtgcta gaagttggcc attgttaagg    9360
aactccttga attaaaaaaa cacatattaa gacttagttt tcattaaaac aaacaaaaat    9420
aaacctcaga gtaacttta aagtcttttt aaaatggatc tttctttgtt atatgaaacc     9480
agtttggact attatccaaa gtatgtagct accactctgc aggaactcag gaagaggtgg    9540
aataagtgtt gaaatctcca aaccctgatt tcacttgact ctctgatttc acctgtgaag   9600
aaagtgggtt aatgagaaat ccttcagtga gcatttact cattagtctt catatgaccc     9660
caatttctta accaaaccaa atggaagatt ttctttctct ctcttcactg aattatgttt    9720 taaaagagg aggataattc atcatgaata acaattataa ctggattatg gactcaaaga    9780
tttgttttcc ttctttccag gatgaactcc aggataaaat ccaccccttt gcccagacac    9840
agtctctagt ctatcccttc cctggaccca tccataacag cctcccacaa aacatccctc    9900
ctcttactca aaccctgtg gtggtgccgc ctttccttca gcctgaagta atgggagtct     9960
ccaaagtgaa ggaggctatg gctcctaagc acaaagaaat gcccttccct aaatatccag    10020
ttgagccctt tactgaaagc cagagcctga ctctcactga tgttgaaaat ctgcaccttc    10080
ctctgcctct gctccagtct tggatgcacc agcctcacca gctcttcct ccaactgtca     10140 tgtttcctcc tcagtccgtg ctgtcccttt ctcagtccaa agtcctgcct gttccccaga    10200
aagcagtgcc ctatcccag agagatatgc ccattcaggc ctttctgctg taccaggagc     10260
ctgtactcgg tcctgtccgg ggacccttcc ctattattgt aagtctaaat ttactaactg    10320
tgcctgttta acttctgatg tttgtatgat attcgagtaa ttaagagtcc tataaaaaaa    10380
tgaataatga atggttccaa aataagcata gctgagatta atgattgtca gcattagtta    10440
taaatagaat aagctggaga accttcacct ccctccacc accagatctc aatgtctagg     10500
cttacccgtg gagattctga tgtaattgtt ctttctatgt agaagaaact tattgggaag    10560
```

```
aaataatata atggactatg atttaattgg tctgttgaga accaattaaa ttagatgaaa    10620
gcgattaagt acaataaagc caaaattgaa tttgataatc tcatttggct aagaataaca    10680
aacctaagaa ggtttgctat tttctacaat tttgaagttc tccttatgca caattatttc    10740
accacatgac tcatttcaca tcgtgttttt gatatatgag catatgaggg aaaaatactg    10800
agatgcttat ttcaatactc agggaaaatt tattgccaaa aggcaagaaa tgtataattc    10860
attcacttat tttattttat tatttttttt attttttaagg tctaagagga tttcaaagtg    10920
aatgccccct cctcactttt ggtaagcttt aggatattgg aggcagactg atcatttta     10980 tagttaatat cttttacatt tcattttcct ggataagccc caatagtagc aatttccatc    11040
agtgtaccag cttaaagatt aattataaat ttattttcaa tgattgactg ttatttactg    11100
gcctgaaatt atgtatctgt tatatttcaa ataatgcaaa actgtatata tatggtgttt    11160
acagatttga ttggttttct ttcaatagcc tatatcctta ttattgattg tcatcattta    11220
tagaaaaaac tgaaaataat ttcttatact tttatgtaaa cctgttagag cttattttaa    11280
agatcaactg cattcacatt tctaatctag tcattatgag cttcaatagt tttatctcac    11340
ttaaaatata tatattgtct tttaattcat gagtcaaaat acaatctcac agtccagata    11400
tgggacttaa aaggggata gaatatagtt ttgatattct taacaataca catccttttg     11460
tgatcatgat tcagcagaca tttaataaaa tgattccaag taagccgatg tttggtccta    11520
gaggaatttt tataaccttt aagagaaggc atagcatggt gtttttgtaa taagatttct    11580
tttatgaaaa agtcacacca aaattgcaaa tgggggtgag atgaagagtt ataacatata    11640
actaaatcta tgtttgttct ctattccaca gaattgactg cgactggaaa tatggcaact    11700
tttcaatcct tgcatcatgt tactaagata atttttaaat gagtatacat ggaacaaaaa    11760
atgaaacttt attcctttat ttattttatg ctttttcatc ttaatttgaa tttgagtcat    11820
aaactatata tttcaaaatt ttaattcaac attagcataa aagttcaatt ttaacttgga    11880
aatatcatga acatatcaaa atatgtataa aaataaattc tggaattgtg attattattt    11940
ctttaagaat ctatttccta accagtcatt tcaataaatt aatccttagg catatttaag    12000
ttttcttgtc tttattatat tttttttaat gaaattggtc tctttattgt taacttaaat    12060
ttatctttga tgttaaaaag agctgtggaa aattaaaatt ggatagaatt catcgatatc    12120
tagatctcga catcgataaa ataaaagatt ttatttagtc tccagaaaaa gggggaatg    12180 aaagacccca cctgtaggtt tggcaagcta gcttaagtaa cgccattttg caaggcatgg    12240
aaaaatacat aactgagaat agagaagttc agatcaaggt caggaacaga tggaacagct    12300
gaatatgggc caaacaggat atctgtggta agcagttcct gccccggctc agggccaaga    12360
acagatggaa cagctgaata tgggccaaac aggatatctg tggtaagcag ttcctgcccc    12420
ggctcagggc caagaacaga tggtccccag atgcggtcca gccctcagca gtttctagag    12480
aaccatcaga tgtttccagg gtgccccaag gacctgaaat gaccctgtgc cttatttgaa    12540
ctaaccaatc agttcgcttc tcgcttctgt tcgcgcgctt ctgctcccg agctcaataa     12600 aagagcccac aacccctcac tcggggcgcc agtcctccga ttgactgagt cgcccgggta    12660
cccgtgtatc caataaaccc tcttgcagtt gcatccgact tgtggtctcg ctgttccttg    12720
ggagggtctc ctctgagtga ttgactaccc gtcagcgggg gtctttcatt              12770
```

<210> SEQ ID NO 5
<211> LENGTH: 9291
<212> TYPE: DNA
<213> ORGANISM: Artificial Sequence
<220> FEATURE:
<223> OTHER INFORMATION: Synthetic

<400> SEQUENCE: 5

```
gaattaattc ataccagatc accgaaaact gtcctccaaa tgtgtccccc tcacactccc      60
aaattcgcgg gcttctgcct cttagaccac tctaccctat tccccacact caccggagcc     120
aaagccgcgg cccttccgtt tctttgcttt tgaaagaccc cacccgtagg tggcaagcta     180
gcttaagtaa cgccactttg caaggcatgg aaaaatacat aactgagaat agaaaagttc     240
agatcaaggt caggaacaaa gaaacagctg aataccaaac aggatatctg tggtaagcgg     300
ttcctgcccc ggctcagggc caagaacaga tgagacagct gagtgatggg ccaaacagga     360
tatctgtggt aagcagttcc tgccccggct cggggccaag aacagatggt ccccagatgc     420
ggtccagccc tcagcagttt ctagtgaatc atcagatgtt ccagggtgc cccaaggacc      480
tgaaaatgac cctgtacctt atttgaacta accaatcagt tcgcttctcg cttctgttcg     540
cgcgcttccg ctctccgagc tcaataaaag agcccacaac ccctcactcg gcgcgccagt     600
cttccgatag actgcgtcgc ccgggtaccc gtattcccaa taaagcctct tgctgtttgc     660
atccgaatcg tggtctcgct gttccttggg agggtctcct ctgagtgatt gactaccac      720
gacggggtc tttcatttgg gggctcgtcc gggatttgga gacccctgcc cagggaccac      780
cgacccacca ccgggaggta agctggccag caacttatct gtgtctgtcc gattgtctag     840
tgtctatgtt tgatgttatg cgcctgcgtc tgtactagtt agctaactag ctctgtatct     900
ggcggacccg tggtggaact gacgagttct gaacacccgg ccgcaaccct gggagacgtc     960
ccagggactt tgggggccgt ttttgtggcc cgacctgagg aagggagtcg atgtggaatc    1020
cgaccccgtc aggatatgtg gttctggtag agacgagaa cctaaaacag ttcccgcctc    1080
cgtctgaatt tttgctttcg gtttggaacc gaagccgcgc gtcttgtctg ctgcagcgct    1140
gcagcatcgt tctgtgttgt ctctgtctga ctgtgtttct gtatttgtct gaaaattagg    1200
gccagactgt taccactccc ttaagtttga ccttaggtca ctggaaagat gtcgagcgga    1260
tcgctcacaa ccagtcggta gatgtcaaga agagacgttg ggttaccttc tgctctgcag    1320
aatggccaac ctttaacgtc ggatggccgc gagacggcac ctttaaccga gacctcatca    1380
cccaggttaa gatcaaggtc ttttcacctg gcccgcatgg acacccagac caggtccccct   1440
acatcgtgac ctgggaagcc ttggcttttg acccccctcc ctgggtcaag ccctttgtac    1500
accctaagcc tccgcctcct cttcctccat ccgccccgtc tctccccctt gaacctcctc    1560
gttcgacccc gcctcgatcc tccctttatc cagccctcac tccttctcta ggcgccggaa    1620
ttccgatctg atcaagagac aggatgagga tcgtttcgca tgattgaaca agatggattg    1680
cacgcaggtt ctccggccgc ttgggtggag aggctattcg gctatgactg ggcacaacag    1740
acaatcggct gctctgatgc cgccgtgttc cggctgtcag cgcaggggcg cccggttctt    1800
tttgtcaaga ccgacctgtc cggtgccctg aatgaactgc aggacgaggc agcgcggcta    1860
tcgtggctgg ccacgacggg cgttccttgc gcagctgtgc tcgacgttgt cactgaagcg    1920
ggaagggact ggctgctatt gggcgaagtg ccggggcagg atctcctgtc atctcacctt    1980
gctcctgccg agaaagtatc catcatggct gatgcaatgc ggcggctgca tacgcttgat    2040
ccggctacct gcccattcga ccaccaagcg aaacatcgca tcgagcgagc acgtactcgg    2100
atggaagccg gtcttgtcga tcaggatgat ctggacgaag agcatcaggg gctcgcgcca    2160
gccgaactgt tcgccaggct caaggcgcgc atgcccgacg cgaggatct cgtcgtgacc    2220
```

```
catggcgatg cctgcttgcc gaatatcatg gtggaaaatg ccgcttttc tggattcatc    2280 gactgtggcc ggctgggtgt ggcggaccgc tatcaggaca tagcgttggc tacccgtgat    2340
attgctgaag agcttggcgg cgaatgggct gaccgcttcc tcgtgcttta cggtatcgcc    2400
gctcccgatt cgcagcgcat cgccttctat cgccttcttg acgagttctt ctgagcggga    2460
ctctggggtt cgaaatgacc gaccaagcga cgcccaacct gccatcacga gatttcgatt    2520
ccaccgccgc cttctatgaa aggttgggct tcggaatcgt tttccgggac gccggctgga    2580
tgatcctcca gcgcgggat ctcatgctgg agttcttcgc ccaccccggg ctcgatcccc    2640
tcgcgagttg gttcagctgc tgcctgaggc tggacgacct cgcggagttc taccggcagt    2700
gcaaatccgt cggcatccag gaaaccagca gcggctatcc gcgcatccat gcccccgaac    2760
tgcaggagtg gggaggcacg atggccgctt ggtcgaggc ggatccggcc attagccata    2820
ttattcattg gttatatagc ataaatcaat attggctatt ggccattgca tacgttgtat    2880
ccatatcata atatgtacat ttatattggc tcatgtccaa cattaccgcc atgttgacat    2940
tgattattga ctagttatta atagtaatca attacggggt cattagttca tagcccatat    3000
atggagttcc gcgttacata acttacggta aatggcccgc ctggctgacc gcccaacgac    3060
ccccgcccat tgacgtcaat aatgacgtat gttcccatag taacgccaat agggactttc    3120
cattgacgtc aatgggtgga gtatttacgg taaactgccc acttggcagt acatcaagtg    3180
tatcatatgc caagtacgcc ccctattgac gtcaatgacg gtaaatggcc cgcctggcat    3240
tatgcccagt acatgacctt atgggacttt cctacttggc agtacatcta cgtattagtc    3300
atcgctatta ccatggtgat gcggttttgg cagtacatca atgggcgtgg atagcggttt    3360
gactcacggg gatttccaag tctccacccc attgacgtca atgggagttt gttttggcac    3420
caaaatcaac gggactttcc aaaatgtcgt aacaactccg ccccattgac gcaaatgggc    3480
ggtaggcatg tacggtggga ggtctatata agcagagctc gtttagtgaa ccgtcagatc    3540
gcctggagac gccatccacg ctgttttgac ctccatagaa gacaccggga ccgatccagc    3600
ctccgcggcc ccaagcttgg atctcaccat ggagttggga ctgcgctggg cttcctcgt    3660 tgctctttta agaggtgtcc agtgtcaggt gcaattggtg gagtctgggg gaggcgtggt    3720
ccagcctggg aggtccctga gactctcctg tgcagcgtct ggattcgcct tcagtagata    3780
tggcatgcac tgggtccgcc aggctccagg caaggggctg gagtgggtgg cagttatatg    3840
gtatgatgga agtaataaat actatgcaga ctccgtgaag ggccgattca ccatctccag    3900
agacaattcc aagaacacgc agtatctgca aatgaacagc ctgagagccg aggacacggc    3960
tgtgtattac tgtgcgagag gcggtgactt cctctactac tactattacg gtatggacgt    4020
ctggggccaa gggaccacgg tcaccgtctc ctcagcctcc accaagggcc catcggtctt    4080
ccccctggca ccctctagca agagcacctc tgggggcaca gcggccctgg gctgcctggt    4140
caaggactac ttccccgaac cggtgacggt gtcgtggaac tcaggcgccc tgaccagcgg    4200
cgtgcacacc ttcccggctg tcctacagtc ctcaggactc tactccctca gcagcgtggt    4260
gaccgtgccc tccagcagct tgggcaccca gacctacatc tgcaacgtga atcacaagcc    4320
cagcaacacc aaggtggaca agagagttgg tgagaggcca gcacagggag ggagggtgtc    4380
tgctggaagc caggctcagc gctcctgcct ggacgcatcc cggctatgca gtcccagtcc    4440
agggcagcaa ggcaggcccc gtctgcctct tcacccggag gcctctgccc gccccactca    4500
tgctcaggga gagggtcttc tggctttttc cccaggctct gggcaggcac aggctaggtg    4560
cccctaaccc aggccctgca cacaaagggg caggtgctgg gctcagacct gccaagagcc    4620
```

```
atatccggga ggaccctgcc cctgacctaa gcccacccca aaggccaaac tctccactcc    4680
ctcagctcgg acaccttctc tcctcccaga ttccagtaac tcccaatctt ctctctgcag    4740
agcccaaatc ttgtgacaaa actcacacat gcccaccgtg cccaggtaag ccagcccagg    4800
cctcgccctc cagctcaagg cgggacaggt gccctagagt agcctgcatc cagggacagg    4860
ccccagccgg gtgctgacac gtccacctcc atctcttcct cagcacctga actcctgggg    4920
ggaccgtcag tcttcctctt ccccccaaaa cccaaggaca ccctcatgat ctcccggacc    4980
cctgaggtca catgcgtggt ggtggacgtg agccacgaag accctgaggt caagttcaac    5040
tggtacgtgg acggcgtgga ggtgcataat gccaagacaa agccgcggga ggagcagtac    5100
aacagcacgt accgtgtggt cagcgtcctc accgtcctgc accaggactg gctgaatggc    5160
aaggagtaca agtgcaaggt ctccaacaaa gccctcccag cccccatcga gaaaaccatc    5220
tccaaagcca aggtgggacc cgtggggtg cgagggccac atggacagag gccggctcgg    5280
cccaccctct gccctgagag tgaccgctgt accaacctct gtccctacag ggcagccccg    5340
agaaccacag gtgtacaccc tgcccccatc ccgggaggag atgaccaaga accaggtcag    5400
cctgacctgc ctggtcaaag gcttctatcc cagcgacatc gccgtggagt gggagagcaa    5460
tgggcagccg gagaacaact acaagaccac gcctcccgtg ctggactccg acggctcctt    5520
cttcctctat agcaagctca ccgtggacaa gagcaggtgg cagcagggga acgtcttctc    5580
atgctccgtg atgcatgagg ctctgcacaa ccactacacg cagaagagcc tctccctgtc    5640
tccgggtaaa tgagaattcc tcgagttaac agatctaggc ctcctaggtc gacatcgata    5700
atcaacctct ggattacaaa atttgtgaaa gattgactgg tattcttaac tatgttgctc    5760
cttttacgct atgtggatac gctgctttaa tgcctttgta tcatgctatt gcttcccgta    5820
tggctttcat tttctcctcc ttgtataaat cctggttgct gtctctttat gaggagttgt    5880
ggcccgttgt caggcaacgt ggcgtggtgt gcactgtgtt gctgacgca accccactg     5940 gttgggcat tgccaccacc tgtcagctcc tttccgggac tttcgctttc ccctccta      6000 ttgccacggc ggaactcatc gccgcctgcc ttgcccgctg ctggacaggg gctcggctgt    6060
tgggcactga caattccgtg gtgttgtcgg ggaaatcatc gtcctttcct ggctgctcg     6120 cctgtgttgc cacctggatt ctgcgcggga cgtccttctg ctacgtccct tcggccctca    6180
atccagcgga ccttccttcc cgcggcctgc tgccggctct gcggcctctt ccgcgtcttc    6240
gccttcgccc tcagacgagt cggatctccc tttgggccgc ctccccgcct gatcgataaa    6300
ataaaagatt ttatttagtc tccagaaaaa gggggaatg aaagacccca cctgtaggtt    6360
tggcaagcta gcttaagtaa cgccattttg caaggcatgg aaaatacat aactgagaat     6420 agagaagttc agatcaaggt caggaacaga tggaacagct gaatatgggc caaacaggat    6480
atctgtggta agcagttcct gccccggctc agggccaaga acagatgaa cagctgaata     6540 tgggccaaac aggatatctg tggtaagcag ttcctgcccc ggctcagggc caagaacaga    6600
tggtccccag atgcggtcca gccctcagca gtttctagag aaccatcaga tgtttccagg    6660
gtgccccaag gacctgaaat gaccctgtgc cttatttgaa ctaaccaatc agttcgcttc    6720
tcgcttctgt tcgcgcgctt ctgctccccg agctcaataa aagagcccac aacccctcac    6780
tcggggcgcc agtcctccga ttgactgagt cgcccgggta cccgtgtatc caataaaccc    6840
tcttgcagtt gcatccgact tgtggtctcg ctgttccttg ggagggtctc ctctgagtga    6900
ttgactaccc gtcagcgggg gtctttcatt tggggggctcg tccggatcg ggagacccct    6960
```

```
gcccagggac caccgaccca ccaccgggag gtaagctggc tgcctcgcgc gtttcggtga    7020
tgacggtgaa aacctctgac acatgcagct cccggagacg gtcacagctt gtctgtaagc    7080
ggatgccggg agcagacaag cccgtcaggg cgcgtcagcg ggtgttggcg ggtgtcgggg    7140
cgcagccatg acccagtcac gtagcgatag cggagtgtat actggcttaa ctatgcggca    7200
tcagagcaga ttgtactgag agtgcaccat atgcggtgtg aaataccgca cagatgcgta    7260
aggagaaaat accgcatcag gcgctcttcc gcttcctcgc tcactgactc gctgcgctcg    7320
gtcgttcggc tgcggcgagc ggtatcagct cactcaaagg cggtaatacg gttatccaca    7380
gaatcagggg ataacgcagg aaagaacatg tgagcaaaag gccagcaaaa ggccaggaac    7440
cgtaaaaagg ccgcgttgct ggcgtttttc cataggctcc gcccccctga cgagcatcac    7500
aaaaatcgac gctcaagtca gaggtggcga acccgacag gactataaag ataccaggcg    7560
tttccccctg gaagctccct cgtgcgctct cctgttccga ccctgccgct taccggatac    7620
ctgtccgcct ttctcccttc gggaagcgtg gcgctttctc atagctcacg ctgtaggtat    7680
ctcagttcgg tgtaggtcgt tcgctccaag ctgggctgtg tgcacgaacc ccccgttcag    7740
cccgaccgct gcgccttatc cggtaactat cgtcttgagt ccaacccggt aagacacgac    7800
ttatcgccac tggcagcagc cactggtaac aggattagca gagcgaggta tgtaggcggt    7860
gctacagagt tcttgaagtg gtggcctaac tacggctaca ctagaaggac agtatttggt    7920
atctgcgctc tgctgaagcc agttaccttc ggaaaaagag ttggtagctc ttgatccggc    7980
aaacaaacca ccgctggtag cggtggtttt tttgtttgca agcagcagat tacgcgcaga    8040
aaaaaaggat ctcaagaaga tcctttgatc ttttctacgg ggtctgacgc tcagtggaac    8100
gaaaactcac gttaagggat tttggtcatg agattatcaa aaaggatctt cacctagatc    8160
cttttaaatt aaaaatgaag ttttaaatca atctaaagta tatatgagta aacttggtct    8220
gacagttacc aatgcttaat cagtgaggca cctatctcag cgatctgtct atttcgttca    8280
tccatagttg cctgactccc cgtcgtgtag ataactacga tacgggaggg cttaccatct    8340
ggccccagtg ctgcaatgat accgcgagac ccacgctcac cggctccaga tttatcagca    8400
ataaaccagc cagccggaag ggccgagcgc agaagtggtc ctgcaacttt atccgcctcc    8460
atccagtcta ttaattgttg ccgggaagct agagtaagta gttcgccagt taatagtttg    8520
cgcaacgttg ttgccattgc tgcaggcatc gtggtgtcac gctcgtcgtt tggtatggct    8580
tcattcagct ccggttccca acgatcaagg cgagttacat gatcccccat gttgtgcaaa    8640
aaagcggtta gctccttcgg tcctccgatc gttgtcagaa gtaagttggc cgcagtgtta    8700
tcactcatgg ttatggcagc actgcataat tctcttactg tcatgccatc cgtaagatgc    8760
ttttctgtga ctggtgagta ctcaaccaag tcattctgag aatagtgtat gcggcgaccg    8820
agttgctctt gcccggcgtc aacacgggat aataccgcgc cacatagcag aactttaaaa    8880
gtgctcatca ttggaaaacg ttcttcgggg cgaaaactct caaggatctt accgctgttg    8940
agatccagtt cgatgtaacc cactcgtgca cccaactgat cttcagcatc ttttactttc    9000
accagcgttt ctgggtgagc aaaaacagga aggcaaaatg ccgcaaaaaa gggaataagg    9060
gcgacacgga aatgttgaat actcatactc ttcctttttc aatattattg aagcatttat    9120
cagggttatt gtctcatgag cggatacata tttgaatgta tttagaaaaa taaacaaata    9180
ggggttccgc gcacatttcc ccgaaaagtg ccacctgacg tctaagaaac cattattatc    9240
atgacattaa cctataaaaa taggcgtatc acgaggccct ttcgtcttca a    9291
```

<210> SEQ ID NO 6
<211> LENGTH: 11228
<212> TYPE: DNA
<213> ORGANISM: Artificial Sequence
<220> FEATURE:
<223> OTHER INFORMATION: Synthetic

<400> SEQUENCE: 6

```
gaattaattc ataccagatc accgaaaact gtcctccaaa tgtgtccccc tcacactccc        60
aaattcgcgg gcttctgcct cttagaccac tctaccctat tccccacact caccggagcc       120
aaagccgcgg cccttccgtt tctttgcttt tgaaagaccc cacccgtagg tggcaagcta       180
gcttaagtaa cgccactttg caaggcatgg aaaatacat aactgagaat agaaaagttc        240
agatcaaggt caggaacaaa gaaacagctg aataccaaac aggatatctg tggtaagcgg       300
ttcctgcccc ggctcagggc caagaacaga tgagacagct gagtgatggg ccaaacagga       360
tatctgtggt aagcagttcc tgccccggct cggggccaag aacagatggt ccccagatgc       420
ggtccagccc tcagcagttt ctagtgaatc atcagatgtt tccagggtgc cccaaggacc       480
tgaaaatgac cctgtacctt atttgaacta accaatcagt tcgcttctcg cttctgttcg       540
cgcgcttccg ctctccgagc tcaataaaag agcccacaac ccctcactcg gcgcgccagt       600
cttccgatag actgcgtcgc ccgggtaccc gtattcccaa taaagcctct tgctgtttgc       660
atccgaatcg tggtctcgct gttccttggg agggtctcct ctgagtgatt gactacccac       720
gacggggtc tttcatttgg gggctcgtcc gggatttgga daccctgcc cagggaccac        780
cgacccacca ccgggaggta agctggccag caacttatct gtgtctgtcc gattgtctag       840
tgtctatgtt tgatgttatg cgcctgcgtc tgtactagtt agctaactag ctctgtatct       900
ggcggacccg tggtggaact gacgagttct gaacacccgg ccgcaaccct gggagacgtc       960
ccagggactt tgggggccgt ttttgtggcc cgacctgagg aagggagtcg atgtggaatc      1020
cgaccccgtc aggatatgtg gttctggtag gagacgagaa cctaaaacag ttcccgcctc      1080
cgtctgaatt tttgctttcg gtttggaacc gaagccgcgc gtcttgtctg ctgcagcgct      1140
gcagcatcgt tctgtgttgt ctctgtctga ctgtgtttct gtatttgtct gaaaattagg      1200
gccagactgt taccactccc ttaagtttga ccttaggtca ctggaaagat gtcgagcgga      1260
tcgctcacaa ccagtcggta gatgtcaaga agagacgttg ggttaccttc tgctctgcag      1320
aatggccaac ctttaacgtc ggatggccgc gagacggcac ctttaaccga acctcatca       1380
cccaggttaa gatcaaggtc ttttcacctg gcccgcatgg acaccagac caggtccct        1440
acatcgtgac ctgggaagcc ttggcttttg accccctcc ctgggtcaag cccttttgtac      1500
accctaagcc tccgcctcct cttcctccat ccgccccgtc tctccccctt gaacctcctc      1560
gttcgacccc gcctcgatcc tccctttatc cagccctcac tccttctcta ggcgccggaa      1620
ttccgatctg atcaagagac aggatgagga tcgtttcgca tgattgaaca agatggattg      1680
cacgcaggtt ctccggccgc ttgggtggag aggctattcg gctatgactg ggcacaacag      1740
acaatcggct gctctgatgc cgccgtgttc cggctgtcag cgcaggggcg cccggttctt      1800
tttgtcaaga ccgacctgtc cggtgccctg aatgaactgc aggacgaggc agcgcggcta      1860
tcgtggctgg ccacgacggg cgttccttgc gcagctgtgc tcgacgttgt cactgaagcg      1920
ggaagggact ggctgctatt gggcgaagtg ccggggcagg atctcctgtc atctcacctt      1980
gctcctgccg agaaagtatc catcatggct gatgcaatgc ggcggctgca tacgcttgat      2040
ccggctacct gcccattcga ccaccaagcg aaacatcgca tcgagcgagc acgtactcgg      2100
```

```
atggaagccg gtcttgtcga tcaggatgat ctggacgaag agcatcaggg gctcgcgcca    2160
gccgaactgt tcgccaggct caaggcgcgc atgcccgacg gcgaggatct cgtcgtgacc    2220
catggcgatg cctgcttgcc gaatatcatg gtggaaaatg ccgcttttc tggattcatc     2280
gactgtggcc ggctgggtgt ggcggaccgc tatcaggaca tagcgttggc tacccgtgat    2340
attgctgaag agcttggcgg cgaatgggct gaccgcttcc tcgtgcttta cggtatcgcc    2400
gctcccgatt cgcagcgcat cgccttctat cgccttcttg acgagttctt ctgagcggga    2460
ctctggggtt cgaaatgacc gaccaagcga cgcccaacct gccatcacga gatttcgatt    2520
ccaccgccgc cttctatgaa aggttgggct tcggaatcgt tttccgggac gccggctgga    2580
tgatcctcca gcgcgggat ctcatgctgg agttcttcgc ccaccccggg ctcgatcccc      2640
tcgcgagttg gttcagctgc tgcctgaggc tggacgacct cgcggagttc taccggcagt    2700
gcaaatccgt cggcatccag gaaaccagca gcggctatcc gcgcatccat gcccccgaac    2760
tgcaggagtg gggaggcacg atggccgctt tggtcgaggc ggatccggcc attagccata    2820
ttattcattg gttatatagc ataaatcaat attggctatt ggccattgca tacgttgtat    2880
ccatatcata atatgtacat ttatattggc tcatgtccaa cattaccgcc atgttgacat    2940
tgattattga ctagttatta atagtaatca attacggggt cattagttca tagcccatat    3000
atggagttcc gcgttacata acttacggta aatggcccgc ctggctgacc gcccaacgac    3060
ccccgcccat tgacgtcaat aatgacgtat gttcccatag taacgccaat agggactttc    3120
cattgacgtc aatgggtgga gtatttacgg taaactgccc acttggcagt acatcaagtg    3180
tatcatatgc caagtacgcc ccctattgac gtcaatgacg gtaaatggcc cgcctggcat    3240
tatgcccagt acatgacctt atgggacttt cctacttggc agtacatcta cgtattagtc    3300
atcgctatta ccatggtgat gcggttttgg cagtacatca atgggcgtgg atagcggttt    3360
gactcacggg gatttccaag tctccacccc attgacgtca atgggagttt gttttggcac    3420
caaaatcaac gggactttcc aaaatgtcgt aacaactccg ccccattgac gcaaatgggc    3480
ggtaggcatg tacggtggga ggtctatata agcagagctc gtttagtgaa ccgtcagatc    3540
gcctggagac gccatccacg ctgttttgac ctccatagaa gaccgggga ccgatccagc     3600
ctccgcggcc ccaagcttga attcgggaaa gacgcaagcc cagaggccct gccatttctg    3660
tgggctcagg tccctactgg ctcaggcccc tgcctccctc ggcaaggcca caatgaaccg    3720
gggagtccct tttaggcact tgcttctggt gctgcaactg gcgctcctcc cagcagccac    3780
tcagggaaag aaagtggtgc tgggcaaaaa aggggataca gtggaactga cctgtacagc    3840
ttcccagaag aagagcatac aattccactg gaaaaactcc aaccagataa agattctggg    3900
aaatcagggc tccttcttaa ctaaaggtcc atccaagctg aatgatcgcg ctgactcaag    3960
aagaagcctt tgggaccaag gaaacttccc cctgatcatc aagaatctta agatagaaga    4020
ctcagatact tacatctgtg aagtggagga ccagaaggag gaggtgcaat tgctagtgtt    4080
cggattgact gccaactctg acacccacct gcttcagggg cagagcctga ccctgacctt    4140
ggagagcccc cctggtagta gcccctcagt gcaatgtagg agtccaaggg gtaaaaacat    4200
acagggggg aagaccctct ccgtgtctca gctggagctc caggatagtg gcacctggac     4260
atgcactgtc ttgcagaacc agaagaaggt ggagttcaaa atagacatcg tggtgctagc    4320
tttcactgtg gctgcaccat ctgtcttcat cttcccgcca tctgatgagc agttgaaatc    4380
tggaactgcc tctgttgtgt gcctgctgaa taacttctat cccagagagg ccaaagtaca    4440
gtggaaggtg gataacgccc tccaatcggg taactcccag gagagtgtca cagagcagga    4500
```

```
cagcaaggac agcacctaca gcctcagcag caccctgacg ctgagcaaag cagactacga   4560
gaaacacaaa gtctacgcct gcgaagtcac ccatcagggc ctgagctcgc ccgtcacaaa   4620
gagcttcaac aggggagagt gttagaggga gaagtgcccc cacctgctcc tcagttccag   4680 cctgacccc tcccatcctt tggcctctga cccttttttcc acaggggacc taccctatt    4740 gcggtcctcc agctcatctt tcacctcacc ccctcctcc tccttggctt tagacctgca    4800
ggcatgcaag cttctcgacg gatccccggg aattcgcccc tctccctccc cccccctaac   4860
gttactggcc gaagccgctt ggaataaggc cggtgtgcgt ttgtctatat gttattttcc   4920
accatattgc cgtcttttgg caatgtgagg gcccggaaac ctggccctgt cttcttgacg   4980
agcattccta ggggtctttc ccctctcgcc aaaggaatgc aaggtctgtt gaatgtcgtg   5040
aaggaagcag ttcctctgga agcttcttga agacaaacaa cgtctgtagc gacccttgc    5100 aggcagcgga accccccacc tggcgacagg tgcctctgcg gccaaaagcc acgtgtataa   5160
gatacacctg caaaggcggc acaaccccag tgccacgttg tgagttggat agttgtggaa   5220
agagtcaaat ggctctcctc aagcgtattc aacaaggggc tgaaggatgc ccagaaggta   5280
ccccattgta tgggatctga tctggggcct cggtgcacat gctttacatg tgtttagtcg   5340
aggttaaaaa aacgtctagg ccccccgaac cacggggacg tggttttcct ttgaaaaaca   5400
cgatgataat atggcctcct ttgtctctct gctcctggta ggcatcctat tccatgccac   5460
ccaggccaaa aaagtggtgc tgggcaaaaa aggggataca gtggaactga cctgtacagc   5520
ttcccagaag aagagcatac aattccactg gaaaaactcc aaccagataa agattctggg   5580
aaatcagggc tccttcttaa ctaaaggtcc atccaagctg aatgatcgcg ctgactcaag   5640
aagaagcctt tgggaccaag gaaacttccc cctgatcatc aagaatctta agatagaaga   5700
ctcagatact tacatctgtg aagtggagga ccagaaggag gaggtgcaat tgctagtgtt   5760
cggattgact gccaactctg acacccacct gcttcagggg cagagcctga ccctgacctt   5820
ggagagcccc cctggtagta gccctcagt gcaatgtagg agtccaaggg gtaaaaacat    5880
acaggggggg aagaccctct ccgtgtctca gctggagctc caggatagtg gcacctggac   5940
atgcactgtc ttgcagaacc agaagaaggt ggagttcaaa atagacatcg tggtgctagc   6000
tttcgcctcc accaagggcc catcggtctt cccctggcg ccctgctcca ggagcacctc    6060
cgagagcaca gcggccctgg gctgcctggt caaggactac ttccccgaac cggtgacggt   6120
gtcgtggaac tcaggcgctc tgaccagcgg cgtgcacacc ttcccagctg tcctacagtc   6180
ctcaggactc tactccctca gcagcgtggt gaccgtgccc tccagcaact tcggcaccca   6240
gacctacacc tgcaacgtag atcacaagcc cagcaacacc aaggtggaca agacagttgg   6300
tgagaggcca gctcagggag ggagggtgtc tgctggaagc caggctcagc cctcctgcct   6360
ggacgcaccc cggctgtgca gccccagccc agggcagcaa ggcaggcccc atctgtctcc   6420
tcacccggag gcctctgccc gccccactca tgctcaggga gagggtcttc tggcttttc    6480 caccaggctc caggcaggca caggctgggt gccctaccc caggcccttc acacacaggg    6540
gcaggtgctt ggctcagacc tgccaaaagc catatccggg aggaccctgc ccctgaccta   6600
agccgacccc aaaggccaaa ctgtccactc cctcagctcg acaccttct ctcctcccag    6660 atccgagtaa ctcccaatct tctctctgca gagcgcaaat gttgtgtcga gtgcccaccg   6720
tgcccaggta agccagccca ggcctcgccc tccagctcaa ggcgggacag gtgccctaga   6780
gtagcctgca tccagggaca ggccccagct gggtgctgac acgtccacct ccatctcttc   6840
```

```
ctcagcacca cctgtggcag gaccgtcagt cttcctcttc cccccaaaac ccaaggacac    6900
cctcatgatc tcccggaccc ctgaggtcac gtgcgtggtg gtggacgtga gccacgaaga    6960
ccccgaggtc cagttcaact ggtacgtgga cggcgtggag gtgcataatg ccaagacaaa    7020
gccacgggag gagcagttca acagcacgtt ccgtgtggtc agcgtcctca ccgttgtgca    7080
ccaggactgg ctgaacggca aggagtacaa gtgcaaggtc tccaacaaag gcctcccagc    7140
ccccatcgag aaaaccatct ccaaaaccaa aggtgggacc cgcggggtat gagggccaca    7200
tggacagagg ccggctcggc ccaccctctg ccctgggagt gaccgctgtg ccaacctctg    7260
tccctacagg gcagccccga gaaccacagg tgtacaccct gcccccatcc cgggaggaga    7320
tgaccaagaa ccaggtcagc ctgacctgcc tggtcaaagg cttctacccc agcgacatcg    7380
ccgtggagtg ggagagcaat gggcagccgg agaacaacta caagaccaca cctcccatgc    7440
tggactccga cggctccttc ttcctctaca gcaagctcac cgtggacaag agcaggtggc    7500 agcagggaa cgtcttctca tgctccgtga tgcatgaggc tctgcacaac cactacacgc    7560
agaagagcct ctccctgtct ccgggtaaat gagtgccacg gccggcaagc ccccgctcgc    7620
ctcctaggtc gacatcgata atcaacctct ggattacaaa atttgtgaaa gattgactgg    7680
tattcttaac tatgttgctc cttttacgct atgtggatac gctgctttaa tgcctttgta    7740
tcatgctatt gcttcccgta tggctttcat tttctcctcc ttgtataaat cctggttgct    7800
gtctctttat gaggagttgt ggcccgttgt caggcaacgt ggcgtggtgt gcactgtgtt    7860
tgctgacgca accccactg gttggggcat tgccaccacc tgtcagctcc tttccgggac    7920
tttcgctttc ccctcccta ttgccacggc ggaactcatc gccgcctgcc ttgcccgctg    7980
ctggacaggg gctcggctgt tgggcactga caattccgtg gtgttgtcgg ggaaatcatc    8040
gtcctttcct tggctgctcg cctgtgttgc cacctggatt ctgcgcggga cgtccttctg    8100
ctacgtccct tcggccctca atccagcgga ccttccttcc gcggcctgc tgccggctct    8160 gcggcctctt ccgcgtcttc gccttcgccc tcagacgagt cggatctccc tttgggccgc    8220
ctccccgcat cgataaaata aaagatttta tttagtctcc agaaaaaggg gggaatgaaa    8280 gacccccacct gtaggtttgg caagctagct taagtaacgc cattttgcaa ggcatggaaa    8340
aatacataac tgagaataga gaagttcaga tcaaggtcag gaacagatgg aacagctgaa    8400
tatgggccaa acaggatatc tgtggtaagc agttcctgcc ccggctcagg gccaagaaca    8460
gatggaacag ctgaatatgg gccaaacagg atatctgtgg taagcagttc ctgccccggc    8520
tcagggccaa gaacagatgg tccccagatg cggtccagcc ctcagcagtt tctagagaac    8580
catcagatgt ttccagggtg ccccaaggac ctgaaatgac cctgtgcctt atttgaacta    8640
accaatcagt tcgcttctcg cttctgttcg cgcgcttctg ctccccgagc tcaataaaag    8700
agcccacaac ccctcactcg gggcgccagt cctccgattg actgagtcgc ccgggtaccc    8760
gtgtatccaa taaaccctct tgcagttgca tccgacttgt ggtctcgctg ttccttggga    8820
gggtctcctc tgagtgattg actacccgtc agcgggggtc tttcatttgg ggctcgtcc    8880 gggatcggga gacccctgcc cagggaccac cgacccacca ccgggaggta agctggctgc    8940
ctcgcgcgtt tcggtgatga cggtgaaaac ctctgacaca tgcagctccc ggagacggtc    9000
acagcttgtc tgtaagcgga tgccgggagc agacaagccc gtcagggcgc gtcagcgggt    9060
gttggcgggt gtcggggcgc agccatgacc cagtcacgta gcgatagcgg agtgtatact    9120
ggcttaacta tgcggcatca gagcagattg tactgagagt gcaccatatg cggtgtgaaa    9180
taccgcacag atgcgtaagg agaaaatacc gcatcaggcg ctcttccgct tcctcgctca    9240
```

```
ctgactcgct gcgctcggtc gttcggctgc ggcgagcggt atcagctcac tcaaaggcgg   9300
taatacggtt atccacagaa tcaggggata acgcaggaaa gaacatgtga gcaaaaggcc   9360
agcaaaaggc caggaaccgt aaaaaggccg cgttgctggc gttttttccat aggctccgcc   9420 ccccctgacga gcatcacaaa aatcgacgct caagtcagag gtggcgaaac ccgacaggac   9480
tataaagata ccaggcgttt ccccctggaa gctccctcgt gcgctctcct gttccgaccc   9540
tgccgcttac cggatacctg tccgcctttc tcccttcggg aagcgtggcg ctttctcata   9600
gctcacgctg taggtatctc agttcggtgt aggtcgttcg ctccaagctg gctgtgtgc    9660 acgaaccccc cgttcagccc gaccgctgcg ccttatccgg taactatcgt cttgagtcca   9720
acccggtaag acacgactta tcgccactgg cagcagccac tggtaacagg attagcagag   9780
cgaggtatgt aggcggtgct acagagttct tgaagtggtg gcctaactac ggctacacta   9840
gaaggacagt atttggtatc tgcgctctgc tgaagccagt taccttcgga aaaagagttg   9900
gtagctcttg atccggcaaa caaaccaccg ctggtagcgg tggtttttttt gtttgcaagc   9960 agcagattac gcgcagaaaa aaaggatctc aagaagatcc tttgatcttt tctacggggt   10020
ctgacgctca gtggaacgaa aactcacgtt aagggatttt ggtcatgaga ttatcaaaaa   10080
ggatcttcac ctagatcctt ttaaattaaa aatgaagttt taaatcaatc taaagtatat   10140
atgagtaaac ttggtctgac agttaccaat gcttaatcag tgaggcacct atctcagcga   10200
tctgtctatt tcgttcatcc atagttgcct gactccccgt cgtgtagata actacgatac   10260
gggagggctt accatctggc cccagtgctg caatgatacc gcgagaccca cgctcaccgg   10320
ctccagattt atcagcaata aaccagccag ccggaagggc cgagcgcaga agtggtcctg   10380
caactttatc cgcctccatc cagtctatta attgttgccg ggaagctaga gtaagtagtt   10440
cgccagttaa tagtttgcgc aacgttgttg ccattgctgc aggcatcgtg gtgtcacgct   10500
cgtcgtttgg tatggcttca ttcagctccg gttcccaacg atcaaggcga gttacatgat   10560
cccccatgtt gtgcaaaaaa gcggttagct ccttcggtcc tccgatcgtt gtcagaagta   10620
agttggccgc agtgttatca ctcatggtta tggcagcact gcataattct cttactgtca   10680
tgccatccgt aagatgcttt tctgtgactg gtgagtactc aaccaagtca ttctgagaat   10740
agtgtatgcg gcgaccgagt tgctcttgcc cggcgtcaac acgggataat accgcgccac   10800
atagcagaac tttaaaagtg ctcatcattg gaaaacgttc ttcggggcga aaactctcaa   10860
ggatcttacc gctgttgaga tccagttcga tgtaacccac tcgtgcaccc aactgatctt   10920
cagcatcttt tactttcacc agcgtttctg ggtgagcaaa aacaggaagg caaaatgccg   10980
caaaaaaggg aataagggcg acacggaaat gttgaatact catactcttc cttttttcaat  11040 attattgaag catttatcag ggttattgtc tcatgagcgg atacatattt gaatgtattt   11100
agaaaaataa acaaataggg gttccgcgca catttccccg aaaagtgcca cctgacgtct   11160
aagaaaccat tattatcatg acattaacct ataaaaatag gcgtatcacg aggcccttc    11220 gtcttcaa                                                             11228
```

<210> SEQ ID NO 7
<211> LENGTH: 3273
<212> TYPE: DNA
<213> ORGANISM: Artificial Sequence
<220> FEATURE:
<223> OTHER INFORMATION: Synthetic

<400> SEQUENCE: 7

```
atgaaccggg gagtcccttt taggcacttg cttctggtgc tgcaactggc gctcctccca      60
gcagccactc agggaaagaa agtggtgctg ggcaaaaaag gggatacagt ggaactgacc     120
tgtacagctt cccagaagaa gagcatacaa ttccactgga aaaactccaa ccagataaag     180
attctgggaa atcagggctc cttcttaact aaaggtccat ccaagctgaa tgatcgcgct     240
gactcaagaa gaagcctttg ggaccaagga aacttccccc tgatcatcaa gaatcttaag     300
atagaagact cagatactta catctgtgaa gtggaggacc agaaggagga ggtgcaattg     360
ctagtgttcg gattgactgc caactctgac acccacctgc ttcagggca gagcctgacc      420
ctgaccttgg agaccccccc tggtagtagc ccctcagtgc aatgtaggag tccaaggggt     480
aaaaacatac agggggggaa gaccctctcc gtgtctcagc tggagctcca ggatagtggc     540
acctggacat gcactgtctt gcagaaccag aagaaggtgg agttcaaaat agacatcgtg     600
gtgctagctt tcactgtggc tgcaccatct gtcttcatct cccgccatc tgatgagcag      660
ttgaaatctg gaactgcctc tgttgtgtgc ctgctgaata acttctatcc cagagaggcc     720
aaagtacagt ggaaggtgga taacgccctc caatcgggta actcccagga gagtgtcaca     780
gagcaggaca gcaaggacag cacctacagc ctcagcagca ccctgacgct gagcaaagca     840
gactacgaga aacacaaagt ctacgcctgc gaagtcaccc atcagggcct gagctcgccc     900
gtcacaaaga gcttcaacag gggagagtgt tagagggaga agtgccccca cctgctcctc     960
agttccagcc tgacccccctc ccatcctttg gcctctgacc cttttccac aggggaccta     1020
cccctattgc ggtcctccag ctcatctttc acctcacccc cctcctcctc cttggcttta     1080
gacctgcagg catgcaagct tctcgacgga tccccgggaa ttcgcccctc tcctcccccc    1140
cccctaacgt tactggccga agccgcttgg aataaggccg gtgtgcgttt gtctatatgt    1200
tattttccac catattgccg tcttttggca atgtgagggc ccggaaacct ggccctgtct    1260
tcttgacgag cattcctagg ggtctttccc ctctcgccaa aggaatgcaa ggtctgttga    1320
atgtcgtgaa ggaagcagtt cctctggaag cttcttgaag acaaacaacg tctgtagcga    1380
cccttttgcag gcagcggaac cccccacctg gcgacaggtg cctctgcggc caaaagccac    1440
gtgtataaga tacacctgca aaggcggcac aaccccagtg ccacgttgtg agttggatag    1500
ttgtggaaag agtcaaatgg ctctcctcaa gcgtattcaa caaggggctg aaggatgccc    1560
agaaggtacc ccattgtatg ggatctgatc tggggcctcg gtgcacatgc tttacatgtg    1620
tttagtcgag gttaaaaaaa cgtctaggcc ccccgaacca cggggacgtg gttttccttt    1680
gaaaaacacg atgataatat ggcctccttt gtctctctgc tcctggtagg catcctattc    1740
catgccaccc aggccaaaaa agtggtgctg ggcaaaaaag gggatacagt ggaactgacc    1800
tgtacagctt cccagaagaa gagcatacaa ttccactgga aaaactccaa ccagataaag    1860
attctgggaa atcagggctc cttcttaact aaaggtccat ccaagctgaa tgatcgcgct    1920
gactcaagaa gaagcctttg ggaccaagga aacttccccc tgatcatcaa gaatcttaag    1980
atagaagact cagatactta catctgtgaa gtggaggacc agaaggagga ggtgcaattg    2040
ctagtgttcg gattgactgc caactctgac acccacctgc ttcagggca gagcctgacc     2100
ctgaccttgg agaccccccc tggtagtagc ccctcagtgc aatgtaggag tccaaggggt    2160
aaaaacatac agggggggaa gaccctctcc gtgtctcagc tggagctcca ggatagtggc    2220
acctggacat gcactgtctt gcagaaccag aagaaggtgg agttcaaaat agacatcgtg    2280
gtgctagctt tcgcctccac caagggccca tcggtcttcc ccctggcgcc ctgctccagg    2340
agcacctccg agagcacagc ggccctgggc tgcctggtca aggactactt ccccgaaccg    2400
```

```
gtgacggtgt cgtggaactc aggcgctctg accagcggcg tgcacacctt cccagctgtc     2460
ctacagtcct caggactcta ctccctcagc agcgtggtga ccgtgccctc cagcaacttc     2520
ggcacccaga cctacacctg caacgtagat cacaagccca gcaacaccaa ggtggacaag     2580
acagttgagc gcaaatgttg tgtcgagtgc ccaccgtgcc cagcaccacc tgtggcagga     2640
ccgtcagtct tcctcttccc cccaaaaccc aaggacaccc tcatgatctc ccggacccct     2700
gaggtcacgt gcgtggtggt ggacgtgagc cacgaagacc ccgaggtcca gttcaactgg     2760
tacgtggacg gcgtggaggt gcataatgcc aagacaaagc cacgggagga gcagttcaac     2820
agcacgttcc gtgtggtcag cgtcctcacc gttgtgcacc aggactggct gaacggcaag     2880
gagtacaagt gcaaggtctc caacaaaggc ctcccagccc ccatcgagaa aaccatctcc     2940
aaaaccaaag ggcagccccg agaaccacag gtgtacaccc tgcccccatc ccgggaggag     3000
atgaccaaga accaggtcag cctgacctgc ctggtcaaag gcttctaccc cagcgacatc     3060
gccgtggagt gggagagcaa tgggcagccg gagaacaact acaagaccac acctcccatg     3120
ctggactccg acggctcctt cttcctctac agcaagctca ccgtggacaa gagcaggtgg     3180
cagcagggga acgtcttctc atgctccgtg atgcatgagg ctctgcacaa ccactacacg     3240
cagaagagcc tctccctgtc tccgggtaaa tga                                 3273
```